US012692485B2

(12) United States Patent
Nolan et al.

(10) Patent No.: US 12,692,485 B2
(45) **Date of Patent: *Jul. 28, 2026**

(54) PEGYLATED KYNURENINASE ENZYMES AND USES THEREOF FOR THE TREATMENT OF CANCER

(71) Applicant: THE BOARD OF REGENTS OF THE UNIVERSITY OF TEXAS SYSTEM, Austin, TX (US)

(72) Inventors: James Nolan, Boston, MA (US); Michelle Zhang, Lexington, MA (US); George Georgiou, Austin, TX (US); Everett Stone, Austin, TX (US); John Blazeck, Austin, TX (US); Christos Karamitros, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 98 days.

This patent is subject to a terminal disclaimer.

(21) Appl. No.: 17/073,030

(22) Filed: Oct. 16, 2020

(65) Prior Publication Data

US 2021/0115416 A1 Apr. 22, 2021

Related U.S. Application Data

(60) Provisional application No. 62/916,493, filed on Oct. 17, 2019.

(51) Int. Cl.

*C12N 9/14* (2006.01)
*A61K 35/17* (2025.01)

(Continued)

(52) U.S. Cl.

CPC ................ *C12N 9/14* (2013.01); *A61K 35/17* (2013.01); *A61K 47/10* (2013.01); *C07K 1/16* (2013.01);

(Continued)

(58) Field of Classification Search

CPC .......... C12N 9/14; A61K 35/17; A61K 47/10; A61K 47/6803; A61K 9/0019;

(Continued)

(56) References Cited

U.S. PATENT DOCUMENTS

| | | | |
|---|---|---|---|
| 9,808,486 | B2 | 11/2017 | Georgiou et al. |
| 9,975,959 | B2 | 5/2018 | Georgiou et al. |

(Continued)

FOREIGN PATENT DOCUMENTS

| | | | |
|---|---|---|---|
| CN | 1442487 | A | 9/2003 |
| JP | 2008-237022 | A | 10/2008 |

(Continued)

OTHER PUBLICATIONS

Xiaojiao Shang, Deqiang Yu, and Raja Ghosh Biomacromolecules 2011 12 (7), 2772-2779 DOI: 10.1021/bm200541r (Year: 2011).*

(Continued)

*Primary Examiner* — Louise W Humphrey
*Assistant Examiner* — Candice Lee Swift
(74) *Attorney, Agent, or Firm* — pH IP Law

(57) ABSTRACT

Kynureninase enzymes covalently bound to polyethylene glycol are described. Aspects of the disclosure provide compositions and methods for improving the effective treatment of cancer by way of kynurenine depletion using such molecules.

10 Claims, 9 Drawing Sheets

Specification includes a Sequence Listing.

(51) Int. Cl.
*A61K 47/10* (2017.01)
*C07K 1/16* (2006.01)
*C07K 16/28* (2006.01)

(52) U.S. Cl.
CPC ...... *C07K 16/2818* (2013.01); *C07K 16/2827* (2013.01); *C12Y 307/01003* (2013.01)

(58) Field of Classification Search
CPC ........ A61K 38/46; A61K 47/60; A61K 45/06; A61K 47/02; A61K 47/12; C07K 1/16; C07K 16/2818; C07K 16/2827; C12Y 307/01003; A61P 35/00
See application file for complete search history.

(56) References Cited

U.S. PATENT DOCUMENTS

| | | | |
|---|---|---|---|
| 10,772,913 B2 | 9/2020 | Georgiou et al. | |
| 11,648,272 B2 * | 5/2023 | Georgiou | A61K 47/60 424/94.6 |
| 2007/0048855 A1 | 3/2007 | Gamez et al. | |
| 2015/0064154 A1 | 3/2015 | Georgiou et al. | |
| 2016/0058845 A1 | 3/2016 | Georgiou et al. | |
| 2019/0002579 A1 | 1/2019 | Georgiou et al. | |
| 2019/0350975 A1 | 11/2019 | Georgiou et al. | |

FOREIGN PATENT DOCUMENTS

| | | |
|---|---|---|
| WO | WO-2004/093871 A1 | 11/2004 |
| WO | WO-2008/036642 A2 | 3/2008 |
| WO | WO-2013/034685 A1 | 3/2013 |
| WO | WO-2015/031771 A2 | 3/2015 |
| WO | WO-2016/033488 A1 | 3/2016 |
| WO | WO-2017/151860 A1 | 9/2017 |
| WO | WO-2019/204269 A1 | 10/2019 |

OTHER PUBLICATIONS

Morpurgo, Margherita, Edward A. Bayer, and Meir Wilchek. "N-hydroxysuccinimide carbonates and carbamates are useful reactive reagents for coupling ligands to lysines on proteins." Journal of biochemical and biophysical methods 38.1 (1999): 17-28. (Year: 1999).*

Veronese, Francesco M. "Peptide and protein PEGylation: a review of problems and solutions." Biomaterials 22.5 (2001): 405-417. (Year: 2001).*

Phillips, Robert S. "Structure and mechanism of kynureninase." Archives of biochemistry and biophysics 544 (2014): 69-74. (Year: 2014).*

Triplett, Todd A., et al. "Reversal of indoleamine 2, 3-dioxygenase-mediated cancer immune suppression by systemic kynurenine depletion with a therapeutic enzyme." Nature biotechnology 36.8 (2018): 758-764. (Year: 2018).*

Supplementary Information for Triplett, Todd A., et al. "Reversal of indoleamine 2, 3-dioxygenase-mediated cancer immune suppression by systemic kynurenine depletion with a therapeutic enzyme." Nature biotechnology 36.8 (2018): 758-764. (Year: 2018).*

NOF America Corporation; https://www.nofamerica.com/store/index.php?dispatch=products.view&product_id=14; accessed Jan. 13, 2023 (Year: 2023).*

NOF American Corporation 2; https://www.nofamerica.com/store/index.php?dispatch=categories.view&category_id=7; accessed Jan. 13, 2023 (Year: 2023).*

Tsui, Sam-Mui, et al. Cancer Cell International 9 (2009): 1-13. (Year: 2009).*

Li, Qing, et al. "Tumor uptake of pegylated diabodies: Balancing systemic clearance and vascular transport." Journal of Controlled Release 279 (2018): 126-135. (Year: 2018).*

Hamidi, Mehrdad, Amir Azadi, and Pedram Rafiei. "Pharmacokinetic consequences of pegylation." Drug delivery 13.6 (2006): 399-409. (Year: 2006).*

Caliceti, Paolo, and Francesco M. Veronese. "Pharmacokinetic and biodistribution properties of poly (ethylene glycol)-protein conjugates." Advanced drug delivery reviews 55.10 (2003): 1261-1277. (Year: 2003).*

Zhu, Saijie, et al. "Partly PEGylated polyamidoamine dendrimer for tumor-selective targeting of doxorubicin: the effects of PEGylation degree and drug conjugation style." Biomaterials 31.6 (2010): 1360-1371. (Year: 2010).*

Pasut, Gianfranco, Mauro Sergi, and Francesco M. Veronese. "Anticancer PEG-enzymes: 30 years old, but still a current approach." Advanced drug delivery reviews 60.1 (2008): 69-78. (Year: 2008).*

International Search Report and Written Opinion for International Application No. PCT/US19/27623, mailed Aug. 22, 2019 (15 pages).

U.S. Appl. No. 16/996,806, filed Aug. 18, 2020 (87 pages).

International Search Report and Written Opinion for International Patent Application No. PCT/US2020/056082, mailed Feb. 9, 2021 (15 pages).

Momany et al., "Three-dimensional structure of kynureninase from pseudomonas flurescens," Biochemistry. 43(5):1193-1203 (2004).

Gailani et al., "Studies on tryptophan metabolism in patients with bladder cancer," Cancer Res. 33(5):1071-7 (1973).

Alberati-Giani et al., "Isolation and expression of a cDNA clone encoding human kynureninase," Eur J Biochem. 239(2):460-8 (1996).

Opitz et al., "An endogenous tumour-promoting ligand of the human aryl hydrocarbon receptor," Nature 478(7368):197-203 (2011).

Lima et al., "Crystal structure of *Homo sapiens* kynureninase," available in PMC Sep. 8, 2008, published in final edited form as: Biochemistry 46(10):2735-44 (2007) (23 pages).

Toma et al., "Cloning and recombinant expression of rat and human kynureninase," FEBS Lett. 12;408(1):5-10 (May 1997).

Walsh et al., "Purification and biochemical characterization of some of the properties of recombinant human kynureninase," Eur J Biochem. 269(8):2069-74 (Apr. 2002).

Machine Translation of CN 1442487 A, downloaded from https://patents.google.com/patent/CN1442487A/en?oq=CN1442487A+ on Mar. 25, 2025.

Search Report issued in corresponding Chinese Patent Application No. 202080081803.8, dated Dec. 27, 2024.

* cited by examiner

PEGYLATED KYNURENINASE ENZYMES AND USES THEREOF FOR THE TREATMENT OF CANCER

FIELD OF THE INVENTION

The disclosure relates to compositions and methods of synthesis of PEGylated kynureninase enzymes and their uses for the treatment of cancer.

Sequence Listing

The instant application contains a Sequence Listing which has been submitted electronically in ASCII format and is hereby incorporated by reference in its entirety. Said ASCII copy, created on Oct. 16, 2020, is named 51175-014002_Sequence_Listing_10_16_20_ST25 and is 12,461 bytes in size.

BACKGROUND OF THE INVENTION

Kynurenine is a metabolite of the amino acid tryptophan generated via the action of either indolamine 2,3 dioxygenase (IDO) or tryptophan 2,3 dioxygenase (TDO). Many tumor cells regulate the expression of IDO and/or TDO to elevate the local concentrations of kynurenine which in turn inhibits the function of tumor infiltrating T-cells that would otherwise attack the tumor. Kynurenine concentrations can be depleted by way of the kynureninase enzyme, which carries out the degradation of kynurenine into anthranilic acid. There remains a need for the development of therapeutic compounds with high catalytic activity for kynurenine degradation and enhanced stability to deactivation in serum in order to achieve prolonged depletion of kynurenine such that T-cells can effectively identify and attack tumor cells.

SUMMARY OF THE INVENTION

The present disclosure provides kynureninase enzymes covalently attached to polyethylene glycol (PEG) molecules. The PEG molecules covalently attached to kynureninase can be used to achieve, for example, greater serum stability and increased catalytic efficiency of kynurenine degradation. A wide array of mutant kynureninase enzymes having increased catalytic efficiency along with an assortment of PEG molecules having various linking groups can be used in conjunction with the compositions and methods described herein. The molecules described herein can be administered to a patient for the treatment of cancers that express indolamine 2,3 dioxygenase (IDO) and/or tryptophan 2,3 dioxygenase (TDO) where localized kynurenine concentrations are elevated, thus preventing targeting and attack by T-cells.

In a first aspect, the disclosure provides a kynureninase homodimer covalently bound to one or more polyethylene glycol (PEG) molecules, wherein the ratio of PEG molecules to homodimer is from about 10:1 to about 40:1, such as about 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1 or 40:1.

In some embodiments, the ratio of PEG molecules to homodimer is from about 11:1 to about 39:1, such as about 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1 or 39:1. In some embodiments, the ratio of PEG molecules to homodimer is from about 12:1 to about 38:1, such as about 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1 or 38:1. In some embodiments, the ratio of PEG molecules to homodimer is from about 13:1 to 37:1, such as about 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1 or 37:1. In some embodiments, the ratio of PEG molecules to homodimer is from about 14:1 to 36:1, such as about 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1 or 36:1. In some embodiments, the ratio of PEG molecules to homodimer is from about 15:1 to 35:1, such as about 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1 or 35:1. In some embodiments, the ratio of PEG molecules to homodimer is from about 16:1 to 34:1, such as about 16:1, 17:1, 18:1, 19:1, 20:1, 21:1, 22:1, 23:1, 24:1, 25:1, 26:1, 27:1, 28:1, 29:1, 30:1, 31:1, 32:1, 33:1 or 34:1. In some embodiments, the ratio of PEG molecules to homodimer is from about 17:1 to 33:1, such as about 17:1, 18:1, 19:1, 20:1, 21:1, 22:1, 23:1, 24:1, 25:1, 26:1, 27:1, 28:1, 29:1, 30:1, 31:1, 32:1 or 33:1. In some embodiments, the ratio of PEG molecules to homodimer is from about 18:1 to 32:1, such as about 18:1, 19:1, 20:1, 21:1, 22:1, 23:1, 24:1, 25:1, 26:1, 27:1, 28:1, 29:1, 30:1, 31:1 or 32:1. In some embodiments, the ratio of PEG molecules to homodimer is from about 19:1 to 31:1, such as about 19:1, 20:1, 21:1, 22:1, 23:1, 24:1, 25:1, 26:1, 27:1, 28:1, 29:1, 30:1 or 31:1. In some embodiments, the ratio of PEG molecules to homodimer is from about 20:1 to 30:1, such as about 20:1, 21:1, 22:1, 23:1, 24:1, 25:1, 26:1, 27:1, 28:1, 29:1 or 30:1. In some embodiments, the ratio of PEG molecules to homodimer is about 21:1 to 29:1, such as about 21:1, 22:1, 23:1, 24:1, 25:1, 26:1, 27:1, 28:1 or 29:1. In some embodiments, the ratio of PEG molecules to homodimer is from about 22:1 to 28:1, such as about 22:1, 23:1, 24:1, 25:1, 26:1, 27:1 or 28:1. In some embodiments, the ratio of PEG molecules to homodimer is from about 23:1 to 27:1, such as about 23:1, 24:1, 25:1, 26:1 or 27:1. In some embodiments, the ratio of PEG molecules to homodimer is from about 24:1 to 26:1, such as about 24:1, 25:1 or 26:1. In some embodiments, the ratio of PEG molecules to homodimer is about 25:1.

In some embodiments, the ratio of PEG molecules to homodimer is about 10:1. In some embodiments, the ratio of PEG molecules to homodimer is about 11:1. In some embodiments, the ratio of PEG molecules to homodimer is about 12:1. In some embodiments, the ratio of PEG molecules to homodimer is about 13:1. In some embodiments, the ratio of PEG molecules to homodimer is about 14:1. In some embodiments, the ratio of PEG molecules to homodimer is about 15:1. In some embodiments, the ratio of PEG molecules to homodimer is about 16:1. In some embodiments, the ratio of PEG molecules to homodimer is about 17:1. In some embodiments, the ratio of PEG molecules to homodimer is about 18:1. In some embodiments, the ratio of PEG molecules to homodimer is about 19:1. In some embodiments, the ratio of PEG molecules to homodimer is about 20:1. In some embodiments, the ratio of PEG molecules to homodimer is about 21:1. In some embodiments, the ratio of PEG molecules to homodimer is about 22:1. In some embodiments, the ratio of PEG molecules to homodimer is about 23:1. In some embodiments, the ratio of PEG molecules to homodimer is about 24:1. In some embodiments, the ratio of PEG molecules to homodimer is about 25:1. In some embodiments, the ratio of PEG molecules to homodimer is about 26:1. In some embodiments, the ratio of PEG molecules to homodimer is about 27:1. In some embodiments, the ratio of PEG molecules to homodimer is about 28:1. In some embodiments, the ratio of PEG molecules to homodimer is about 29:1. In some embodiments, the ratio of PEG molecules to homodimer is about 30:1. In some embodiments, the ratio of PEG molecules to homodimer is about 31:1. In some embodiments, the ratio of PEG molecules to homodimer is about 32:1. In some embodiments, the ratio of PEG molecules to homodimer is about 33:1. In some embodiments, the ratio of PEG molecules to homodimer is about 34:1. In some embodiments, the ratio of PEG molecules to homodimer is about 35:1. In some embodiments, the ratio of PEG molecules to homodimer is about 36:1. In some embodiments, the ratio of PEG molecules to homodimer is about 37:1. In some embodiments, the ratio of PEG molecules to homodimer is about 38:1. In some embodiments, the ratio of PEG molecules to homodimer is about 39:1. In some embodiments, the ratio of PEG molecules to homodimer is about 40:1.

In some embodiments, the ratio of PEG molecules to homodimer is from about 13:1 to about 33:1, such as about 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, or 33:1.

In some embodiments, the ratio of PEG molecules to homodimer is from about 18:1 to about 33:1, such as about 18:1, 19:1, 20:1, 21:1, 22:1, 23:1, 24:1, 25:1, 26:1, 27:1, 28:1, 29:1, 30:1, 31:1, 32:1, or 33:1.

In some embodiments, the ratio of PEG molecules to homodimer is from about 18:1 to about 28:1, such as about 18:1, 19:1, 20:1, 21:1, 22:1, 23:1, 24:1, 25:1, 26:1, 27:1, or 28:1.

In some embodiments, the ratio of PEG molecules to homodimer is from about 18:1 to about 23:1, such as about 18:1, 19:1, 20:1, 21:1, 22:1, or 23:1.

In some embodiments, the ratio of PEG molecules to homodimer is from about 23:1 to about 33:1, such as about 23:1, 24:1, 25:1, 26:1, 27:1, 28:1, 29:1, 30:1, 31:1, 32:1, or 33:1.

In some embodiments, the ratio of PEG molecules to homodimer is from about 23:1 to about 28:1, such as about 23:1, 24:1, 25:1, 26:1, 27:1, or 28:1.

In some embodiments, the PEG molecule has a molecular weight of from about 1 kDa to about 10 kDa, such as a molecular weight of about 1, 2, 3, 4, 5, 6, 7, 8, 9 or 10 kDa. In some embodiments, the PEG molecule has a molecular weight from about 2 kDa to about 9 kDa, such as about 2, 3, 4, 5, 6, 7, 8 or 9 kDa. In some embodiments, the PEG molecule has a molecular weight from about 3 kDa to about 8 kDa, such as about 3, 4, 5, 6, 7 or 8 kDa. In some embodiments, the PEG molecule has a molecular weight from about 4 kDa to about 7 kDa, such as about 4, 5, 6 or 7 kDa. In some embodiments, the PEG molecule has a molecular weight from about 5 kDa to about 6 kDa, such as about 5 or 6 kDa. In some embodiments, the PEG molecular has a molecular weight of about 5 kDa. In some embodiments, the PEG molecule is linear. In some embodiments, the PEG molecule is branched.

In some embodiments, the homodimer is covalently bound to the PEG molecule by way of one or more lysine or cysteine residues, such as by one or more lysine residues by way of a linking group, such as a linking group formed from reaction of a lysine amine with a succinimide group, an aldehyde group, an amide group, a carbamate group, an ester group, an epoxy group, a carboxyl group, a hydroxyl group, or a combination thereof. In some embodiments, the linking group is a succinimide group, such as a succinimidyl succinate, succinimidyl propionate, succinimidyl carboxymethylate, succinimidyl carbonate, succinimidyl succinamide, N-hydroxy succinimide or a combination thereof, such as an N-hydroxy succinimide carbonate. In some embodiments, the linking group is monofunctional.

In some embodiments, the homodimer comprises two polypeptide monomers each having an amino acid sequence that is at least 85% identical to SEQ ID NO: 1 (e.g., 85%, 86%, 87%, 88%, 89%, 90%, 91%, 92%, 93%, 94%, 95%, 96%, 97%, 98%, 99%, or 100% identical to SEQ ID NO: 1). Each polypeptide monomer may have one or more amino acid substitutions, relative to SEQ ID NO: 1, selected from the group consisting of L8P, K38E, Y47L, I48F, K50Q, I51M, S60N, K64N, D65G, E66K, N67D, N67P, D67S, A68F, A68T, A68V, F71L, F71M, L72N, K84E, E88N, E89K, E89S, E90Q, D92E, K93N, K93T, A95H, A95Q, K96N, I97H, I97L, I97V, A98G, A99G, A99I, A99R, A99S, A99T, A99V, Y100N, Y100S, Y100T, G101A, H102W, E103F, E103H, E103N, E103Q, E103R, E103V, E103W, V104D, V104E, V104F, V104H, V104K, V104L, V104R, G105A, G105H, G105S, G105T, E106D, K106D, K106E, K106H, K106N, R107P, R107S, P108R, I110A, I110F, I110L, I110M, I110T, T111D, T111H, T111N, T111R, G112A, G112C, G112D, G112K, G112L, G112M, G112Q, G112R, G112S, G112T, G112Y, N127K, I131V, A132V, L133V, A136T, L137T, T138S, N140D, H142Q, Q14R, Y156H, K163T, D168E, H169R, Q175L, I183F, I183L, I183P, I183S, E184A, E184D, E184R, E184T, E184V, E185T, M187L, M189I, K191A, K191G, K191H, K191M, K191N, K191R, K191S, K191T, K191W, E197A, E197D, E197F, E197K, E197M, E197Q, E197S, E197T, E197V, I201C, I201E, I201F, I201H, I201L, I201S, I201T, I201V, H203K, L219M, L219W, F220L, V223I, F225Y, H230F, H230L, H230Y, N232S, Y246F, F249W, D250E, S274A, S274C, S274G, S274N, S274T, L278M, A280G, A280S, A280T, G281S, A282M, A282P, G284N, I285L, V303L, V303S, F306W, F306Y, S311N, K315E, D317E, D317K, I3310, I331L, I331N, I331S, I331T, I331V, N333T, P334N, P335T, L337T, L338A, L338Q, S341I, K373E, K373N, N375A, N375H, Y376C, Y376F, Y376L, K378G, K378P, K378Q, K378R, K380G, K380S, A382G, A382R, A382T, T383S, K384G, K384N, P386K, P386S, V387L, N389E, I405L, F407Y, S408D, S408N, N411R, D413S, D413V, Q416T, E419A, E419L, K420E, R421N, V424I, K427M, N429E, G432A and A436T. In some embodiments, the amino acid sequence is at least 90% identical to SEQ ID NO: 1 (e.g., 90%, 91%, 92%, 93%, 94%, 95%, 96%, 97%, 98%, or 99% identical to SEQ ID NO: 1) or at least 95% identical to SEQ ID NO: 1 (e.g., 95%, 96%, 97%, 98%, or 99% identical to SEQ ID NO: 1).

In some embodiments, each polypeptide monomer comprises a substitution at A282 (e.g., A282M or A282P), F306 (e.g., F306W or F306Y) and/or F249, such as F249W, relative to SEQ ID NO: 1. In some embodiments, each polypeptide monomer comprises a substitution at A99 relative to SEQ ID NO: 1. In some embodiments, each polypeptide monomer comprises a substitution at G112 relative to SEQ ID NO: 1. In some embodiments, each polypeptide monomer comprises a substitution at E103 relative to SEQ ID NO: 1. In some embodiments, each polypeptide monomer comprises a substitution at V104 relative to SEQ ID NO: 1. In some embodiments, each polypeptide monomer comprises a substitution at S408 relative to SEQ ID NO: 1.

In some embodiments, each polypeptide monomer comprises the F306W substitution. In some embodiments, each polypeptide monomer comprises the L72N substitution. In some embodiments, each polypeptide monomer comprises the H102W and N333T substitutions. In some embodiments, each polypeptide monomer comprises the I183P substitution. In some embodiments, each polypeptide monomer comprises the R107P substitution. In some embodiments, each polypeptide monomer comprises the A436T substitution. In some embodiments, each polypeptide monomer comprises at least one substitution selected from L72N, H102W, A282P, F306W, I331S and N333T relative to SEQ ID NO: 1. In some embodiments, each polypeptide monomer comprises at least two, three, four or five substitutions selected from L72N, H102W, A282P, F306W, I331S and N333T. In some embodiments, each polypeptide monomer comprises the substitutions L72N, H102W, A282P, F306W, I331S and N333T. In some embodiments, each polypeptide monomer comprises the substitutions L72N, A99R, H102W, E103R, V104H, R107P, G112Y, I183P, A282P, F306W, I331S, N333T, S408N and A436T relative to SEQ ID NO: 1.

In some embodiments, each polypeptide monomer has an amino acid sequence that is at least 85% identical to SEQ ID NO: 3 (e.g., 85%, 86%, 87%, 88%, 89%, 90%, 91%, 92%, 93%, 94%, 95%, 96%, 97%, 98%, 99%, or 100% identical to SEQ ID NO: 3). In some embodiments, each polypeptide monomer has an amino acid sequence that is at least 90% identical to SEQ ID NO: 3 (e.g., 90%, 91%, 92%, 93%, 94%, 95%, 96%, 97%, 98%, 99%, or 100% identical to SEQ ID NO: 3). In some embodiments, each polypeptide monomer has an amino acid sequence that is at least 95% identical to SEQ ID NO: 3 (e.g., 95%, 96%, 97%, 98%, 99%, or 100% identical to SEQ ID NO: 3). In some embodiments, each polypeptide monomer has the amino acid sequence of SEQ ID NO: 3. In some embodiments, each polypeptide monomer has one or more conservative amino acid substitutions relative to the amino acid sequence of SEQ ID NO: 3. For example, each polypeptide monomer may have up to 50 conservative amino acid substitutions (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 conservative amino acid substitutions) relative to the amino acid sequence of SEQ ID NO: 3. In some embodiments, each polypeptide monomer may have up to 25 conservative amino acid substitutions (e.g., 1, 2, 3, 4, 5, 6, 7, 8, 9, 10, 11, 12, 13, 14, 15, 16, 17, 18, 19, 20, 21, 22, 23, 24, or 25 conservative amino acid substitutions) relative to the amino acid sequence of SEQ ID NO: 3. In some embodiments, each polypeptide monomer may have up to 10 conservative amino acid substitutions (e.g., 1, 2, 3, 4, 5, 6, 7, 8, 9, or 10 conservative amino acid substitutions) relative to the amino acid sequence of SEQ ID NO: 3. In some embodiments, each polypeptide monomer may have an amino acid sequence that differs from that of SEQ ID NO: 3 only by way of conservative amino acid substitutions.

In some embodiments, each polypeptide monomer has an amino acid sequence that is at least 85% identical to SEQ ID NO: 2 (e.g., 85%, 86%, 87%, 88%, 89%, 90%, 91%, 92%, 93%, 94%, 95%, 96%, 97%, 98%, 99%, or 100% identical to SEQ ID NO: 2). In some embodiments, each polypeptide monomer has an amino acid sequence that is at least 90% identical to SEQ ID NO: 2 (e.g., 90%, 91%, 92%, 93%, 94%, 95%, 96%, 97%, 98%, 99%, or 100% identical to SEQ ID NO: 2). In some embodiments, each polypeptide monomer has an amino acid sequence that is at least 95% identical to SEQ ID NO: 2 (e.g., 95%, 96%, 97%, 98%, 99%, or 100% identical to SEQ ID NO: 2). In some embodiments, each polypeptide monomer has the amino acid sequence of SEQ ID NO: 2. Each polypeptide monomer may have one or more conservative amino acid substitutions relative to the amino acid sequence of SEQ ID NO: 2. For example, each polypeptide monomer may have up to 50 conservative amino acid substitutions (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 conservative amino acid substitutions) relative to the amino acid sequence of SEQ ID NO: 2. In some embodiments, each polypeptide monomer may have up to 25 conservative amino acid substitutions (e.g., 1, 2, 3, 4, 5, 6, 7, 8, 9, 10, 11, 12, 13, 14, 15, 16, 17, 18, 19, 20, 21, 22, 23, 24, or 25 conservative amino acid substitutions) relative to the amino acid sequence of SEQ ID NO: 2. In some embodiments, each polypeptide monomer may have up to 10 conservative amino acid substitutions (e.g., 1, 2, 3, 4, 5, 6, 7, 8, 9, or 10 conservative amino acid substitutions) relative to the amino acid sequence of SEQ ID NO: 2. In some embodiments, each polypeptide monomer may have an amino acid sequence that differs from that of SEQ ID NO: 2 only by way of conservative amino acid.

In some embodiments, the homodimer has a catalytic activity ($kcat/K_M$) of at least $8000M^{-1}$ $s^{-1}$. In some embodiments, the homodimer has a catalytic activity ($kcat/K_M$) of between about $8000M^{-1}$ $s^{-1}$ and 40000 $M^{-1}$ $s^{-1}$; $10000M^{-1}$ $s^{-1}$ and 40000 $M^{-1}$ $s^{-1}$; $20000M^{-1}$ $s^{-1}$ and 40000 $M^{-1}$ $s^{-1}$; or $25000M^{-1}$ $s^{-1}$ and 35000 $M^{-1}$ $s^{-1}$.

In some embodiments, the ratio of PEG molecules to homodimer is about 25:1, the PEG molecule has a molecular weight of about 5 kDa and is bound to the homodimer by way of an N-hydroxysuccinimide ester carbonate linking group.

In another aspect, the disclosure provides a method of extending the circulating half-life of a kynureninase polypeptide, the method comprising contacting the kynureninase polypeptide with a PEGylation agent, wherein the kynureninase polypeptide forms a homodimer, and wherein the molar input ratio of PEGylation agent to kynureninase homodimer is from about 10:1 to about 50:1, such as about 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30;1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1 or 50:1.1 In some embodiments, the molar input ratio of PEGylation agent to kynureninase homodimer is from about 11:1 to about 49:1, such as 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30;1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1 or 49: In some embodiments, the molar input ratio of PEGylation agent to kynureninase homodimer is from about 12:1 to about 48:1, such as 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30;1, 31:1, 32:1, 33:1, 34:1, 35:1, 36:1, 37:1, 38:1, 39:1, 40:1, 41:1, 42:1, 43:1, 44:1, 45:1, 46:1, 47:1 or 48:1. In some embodiments, the molar input ratio of PEGylation agent to kynureninase homodimer is from about 13:1 to about 47:1, such as 13:1, 14:1, 15:1, 16:1, 17:1, 18:1, 19:1, 20:1, 21:1, 22:1, 23:1, 24:1, 25:1, 26:1, 27:1, 28:1, 29:1, 30;1, 31:1, 32:1, 33:1, 34:1, 35:1, 36:1, 37:1, 38:1, 39:1, 40:1, 41:1, 42:1, 43:1, 44:1, 45:1, 46:1 or 47:1. In some embodiments, the molar input ratio of PEGylation agent to kynureninase homodimer is from about 14:1 to about 46:1, such as 14:1, 15:1, 16:1, 17:1, 18:1, 19:1, 20:1, 21:1, 22:1, 23:1, 24:1, 25:1, 26:1, 27:1, 28:1, 29:1, 30;1, 31:1, 32:1, 33:1, 34:1, 35:1, 36:1, 37:1, 38:1, 39:1, 40:1, 41:1, 42:1, 43:1, 44:1, 45:1 or 46:1. In some embodiments, the molar input ratio of PEGylation agent to kynureninase homodimer is from about 15:1 to about 45:1, such as 15:1, 16:1, 17:1, 18:1, 19:1, 20:1, 21:1, 22:1, 23:1, 24:1, 25:1, 26:1, 27:1, 28:1, 29:1, 30;1, 31:1, 32:1, 33:1, 34:1, 35:1, 36:1, 37:1, 38:1, 39:1, 40:1, 41:1, 42:1, 43:1, 44:1 or 45:1. In some embodiments, the molar input ratio of PEGylation agent to kynureninase homodimer is from about 16:1 to about 44:1, such as 16:1, 17:1, 18:1, 19:1, 20:1, 21:1, 22:1, 23:1, 24:1, 25:1, 26:1, 27:1, 28:1, 29:1, 30;1, 31:1, 32:1, 33:1, 34:1, 35:1, 36:1, 37:1, 38:1, 39:1, 40:1, 41:1, 42:1, 43:1 or 44:1. In some embodiments, the molar input ratio of PEGylation agent to kynureninase homodimer is from about 17:1 to about 43:1, such as 17:1, 18:1, 19:1, 20:1, 21:1, 22:1, 23:1, 24:1, 25:1, 26:1, 27:1, 28:1, 29:1, 30;1, 31:1, 32:1, 33:1, 34:1, 35:1, 36:1, 37:1, 38:1, 39:1, 40:1, 41:1, 42:1 or 43:1. In some embodiments, the molar input ratio of PEGylation agent to kynureninase homodimer is from about 18:1 to about 42:1, such as 18:1, 19:1, 20:1, 21:1, 22:1, 23:1, 24:1, 25:1, 26:1, 27:1, 28:1, 29:1, 30;1, 31:1, 32:1, 33:1, 34:1, 35:1, 36:1, 37:1, 38:1, 39:1, 40:1, 41:1 or 42:1. In some embodiments the molar input ratio of PEGylation agent to kynureninase homodimer is from about 19:1 to about 41:1, such as 19:1, 20:1, 21:1, 22:1, 23:1, 24:1, 25:1, 26:1, 27:1, 28:1, 29:1, 30;1, 31:1, 32:1, 33:1, 34:1, 35:1, 36:1, 37:1, 38:1, 39:1, 40:1 or 41:1. In some embodiments, the molar input ratio of PEGylation agent to kynureninase homodimer is from about 20:1 to about 40:1, such as 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1 or 40:1. In some embodiments, the molar input ratio of PEGylation agent to kynureninase homodimer is from about 21:1 to about 39:1, such as 21:1, 22:1, 23:1, 24:1, 25:1, 26:1, 27:1, 28:1, 29:1, 30:1, 31:1, 32:1, 33:1, 34:1, 35:1, 36:1, 37:1, 38:1 or 39:1. In some embodiments, the molar input ratio of PEGylation agent to kynureninase homodimer is from about 22:1 to about 38:1, such as 22:1, 23:1, 24:1, 25:1, 26:1, 27:1, 28:1, 29:1, 30:1, 31:1, 32:1, 33:1, 34:1, 35:1, 36:1, 37:1 or 38:1. In some embodiments, the molar input ratio of PEGylation agent to kynureninase homodimer is from about 23:1 to about 37:1, such as 23:1, 24:1, 25:1, 26:1, 27:1, 28:1, 29:1, 30:1, 31:1, 32:1, 33:1, 34:1, 35:1, 36:1 or 37:1. In some embodiments, the molar input ratio of PEGylation agent to kynureninase homodimer is from about 24:1 to about 36:1, such as 24:1, 25:1, 26:1, 27:1, 28:1, 29:1, 30:1, 31:1, 32:1, 33:1, 34:1, 35:1 or 36:1. In some embodiments, the molar input ratio of PEGylation agent to kynureninase homodimer is from about 25:1 to about 35:1, such as 25:1, 26:1, 27:1, 28:1, 29:1, 30:1, 31:1, 32:1, 33:1, 34:1 or 35:1. In some embodiments, the molar input ratio of PEGylation agent to kynureninase homodimer is from about 26:1 to about 34:1, such as 26:1, 27:1, 28:1, 29:1, 30:1, 31:1, 32:1, 33:1 or 34:1. In some embodiments, the molar input ratio of PEGylation agent to kynureninase homodimer is from about 27:1 to about 33:1, such as 27:1, 28:1, 29:1, 30:1, 31:1, 32:1 or 33:1. In some embodiments, the molar input ratio of PEGylation agent to kynureninase homodimer is from about 28:1 to about 32:1, such 28:1, 29:1, 30:1, 31:1, or 32:1. In some embodiments, the molar input ratio of PEGylation agent to kynureninase homodimer is from about 29:1 to about 31:1, such as 29:1, 30:1 or 31:1. In some embodiments, the molar input ratio of PEGylation agent to kynureninase homodimer is about 30:1.

In another aspect, the disclosure comprises a method of producing a PEGylated kynureninase homodimer, wherein the homodimer comprises two polypeptide monomers, the method comprising contacting the homodimer with a PEGylation agent, and wherein the molar input ratio of PEGylation agent to kynureninase homodimer is from about 10:1 to about 50:1, such as about 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30;1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1 or 50:1. In some embodiments, the molar input ratio of PEGylation agent to kynureninase homodimer is from about 11:1 to about 49:1, such as about 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30;1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1 or 49:1. In some embodiments, the molar input ratio of PEGylation agent to kynureninase homodimer is from about 12:1 to about 48:1, such as about 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30;1, 31:1, 32:1, 33:1, 34:1, 35:1, 36:1, 37:1, 38:1, 39:1, 40:1, 41:1, 42:1, 43:1, 44:1, 45:1, 46:1, 47:1 or 48:1. In some embodiments, the molar input ratio of PEGylation agent to kynureninase homodimer is from about 13:1 to about 47:1, such as about 13:1, 14:1, 15:1, 16:1, 17:1, 18:1, 19:1, 20:1, 21:1, 22:1, 23:1, 24:1, 25:1, 26:1, 27:1, 28:1, 29:1, 30;1, 31:1, 32:1, 33:1, 34:1, 35:1, 36:1, 37:1, 38:1, 39:1, 40:1, 41:1, 42:1, 43:1, 44:1, 45:1, 46:1 or 47:1. In some embodiments, the molar input ratio of PEGylation agent to kynureninase homodimer is from about 14:1 to about 46:1, such as about 14:1, 15:1, 16:1, 17:1, 18:1, 19:1, 20:1, 21:1, 22:1, 23:1, 24:1, 25:1, 26:1, 27:1, 28:1, 29:1, 30;1, 31:1, 32:1, 33:1, 34:1, 35:1, 36:1, 37:1, 38:1, 39:1, 40:1, 41:1, 42:1, 43:1, 44:1, 45:1 or 46:1. In some embodiments, the molar input ratio of PEGylation agent to kynureninase homodimer is from about 15:1 to about 45:1, such as about 15:1, 16:1, 17:1, 18:1, 19:1, 20:1, 21:1, 22:1, 23:1, 24:1, 25:1, 26:1, 27:1, 28:1, 29:1, 30;1, 31:1, 32:1, 33:1, 34:1, 35:1, 36:1, 37:1, 38:1, 39:1, 40:1, 41:1, 42:1, 43:1, 44:1 or 45:1. In some embodiments, the molar input ratio of PEGylation agent to kynureninase homodimer is from about 16:1 to about 44:1, such as about 16:1, 17:1, 18:1, 19:1, 20:1, 21:1, 22:1, 23:1, 24:1, 25:1, 26:1, 27:1, 28:1, 29:1, 30;1, 31:1, 32:1, 33:1, 34:1, 35:1, 36:1, 37:1, 38:1, 39:1, 40:1, 41:1, 42:1, 43:1 or 44:1. In some embodiments, the molar input ratio of PEGylation agent to kynureninase homodimer is from about 17:1 to about 43:1, such as about 17:1, 18:1, 19:1, 20:1, 21:1, 22:1, 23:1, 24:1, 25:1, 26:1, 27:1, 28:1, 29:1, 30;1, 31:1, 32:1, 33:1, 34:1, 35:1, 36:1, 37:1, 38:1, 39:1, 40:1, 41:1, 42:1 or 43:1. In some embodiments, the molar input ratio of PEGylation agent to kynureninase homodimer is from about 18:1 to about 42:1, such as about 18:1, 19:1, 20:1, 21:1, 22:1, 23:1, 24:1, 25:1, 26:1, 27:1, 28:1, 29:1, 30;1, 31:1, 32:1, 33:1, 34:1, 35:1, 36:1, 37:1, 38:1, 39:1, 40:1, 41:1 or 42:1. In some embodiments, the molar input ratio of PEGylation agent to kynureninase homodimer is from about 19:1 to about 41:1, such as about 19:1, 20:1, 21:1, 22:1, 23:1, 24:1, 25:1, 26:1, 27:1, 28:1, 29:1, 30;1, 31:1, 32:1, 33:1, 34:1, 35:1, 36:1, 37:1, 38:1, 39:1, 40:1 or 41:1. In some embodiments, the molar input ratio of PEGylation agent to kynureninase homodimer is from about 20:1 to about 40:1, such as about 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1 or 40:1. In some embodiments, the molar input ratio of PEGylation agent to kynureninase homodimer is from about 21:1 to about 39:1, such as about 21:1, 22:1, 23:1, 24:1, 25:1, 26:1, 27:1, 28:1, 29:1, 30:1, 31:1, 32:1, 33:1, 34:1, 35:1, 36:1, 37:1, 38:1 or 39:1. In some embodiments, the molar input ratio of PEGylation agent to kynureninase homodimer is from about 22:1 to about 38:1, such as about 22:1, 23:1, 24:1, 25:1, 26:1, 27:1, 28:1, 29:1, 30:1, 31:1, 32:1, 33:1, 34:1, 35:1, 36:1, 37:1 or 38:1. In some embodiments, the molar input ratio of PEGylation agent to kynureninase homodimer is from about 23:1 to about 37:1, such as about 23:1, 24:1, 25:1, 26:1, 27:1, 28:1, 29:1, 30:1, 31:1, 32:1, 33:1, 34:1, 35:1, 36:1 or 37:1. In some embodiments, the molar input ratio of PEGylation agent to kynureninase homodimer is from about 24:1 to about 36:1, such as about 24:1, 25:1, 26:1, 27:1, 28:1, 29:1, 30:1, 31:1, 32:1, 33:1, 34:1, 35:1 or 36:1. In some embodiments, the molar input ratio of PEGylation agent to kynureninase homodimer is from about 25:1 to about 35:1, such as about 25:1, 26:1, 27:1, 28:1, 29:1, 30:1, 31:1, 32:1, 33:1, 34:1 or 35:1. In some embodiments, the molar input ratio of PEGylation agent to kynureninase homodimer is from about 26:1 to about 34:1, such as about 26:1, 27:1, 28:1, 29:1, 30:1, 31:1, 32:1, 33:1 or 34:1. In some embodiments, the molar input ratio of PEGylation agent to kynureninase homodimer is from about 27:1 to about 33:1, such as about 27:1, 28:1, 29:1, 30:1, 31:1, 32:1 or 33:1. In some embodiments, the molar input ratio of PEGylation agent to kynureninase homodimer is from about 28:1 to about 32:1, such as about 28:1, 29:1, 30:1, 31:1, or 32:1. In some embodiments, the molar input ratio of PEGylation agent to kynureninase homodimer is from about 29:1 to about 31:1, such as about 29:1, 30:1 or 31:1. In some embodiments, the molar input ratio of PEGylation agent to kynureninase homodimer is about 30:1.

In some embodiments, the molar input ratio of PEGylation agent to kynureninase homodimer is from about 20:1 to about 30:1, such as about 20:1, 21:1, 22:1, 23:1, 24:1, 25:1, 26:1, 27:1, 28:1, 29:1, or 30:1.

In some embodiments, the molar input ratio of PEGylation agent to kynureninase homodimer is from about 10:1 to about 30:1, such as about 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, or 30:1.

In some embodiments, the molar input ratio of PEGylation agent to kynureninase homodimer is from about 11:1 to about 29:1, such as about 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, or 29:1.

In some embodiments, the molar input ratio of PEGylation agent to kynureninase homodimer is from about 12:1 to about 28:1, such as about 12:1, 13:1, 14:1, 15:1, 16:1, 17:1, 18:1, 19:1, 20:1, 21:1, 22:1, 23:1, 24:1, 25:1, 26:1, 27:1, or 28:1.

In some embodiments, the molar input ratio of PEGylation agent to kynureninase homodimer is from about 13:1 to about 27:1, such as about 13:1, 14:1, 15:1, 16:1, 17:1, 18:1, 19:1, 20:1, 21:1, 22:1, 23:1, 24:1, 25:1, 26:1, or 27:1.

In some embodiments, the molar input ratio of PEGylation agent to kynureninase homodimer is from about 14:1 to about 26:1, such as about 14:1, 15:1, 16:1, 17:1, 18:1, 19:1, 20:1, 21:1, 22:1, 23:1, 24:1, 25:1, or 26:1.

In some embodiments, the molar input ratio of PEGylation agent to kynureninase homodimer is from about 15:1 to about 25:1, such as about 15:1, 16:1, 17:1, 18:1, 19:1, 20:1, 21:1, 22:1, 23:1, 24:1, or 25:1.

In some embodiments, the molar input ratio of PEGylation agent to kynureninase homodimer is from about 16:1 to about 24:1, such as about 16:1, 17:1, 18:1, 19:1, 20:1, 21:1, 22:1, 23:1, or 24:1.

In some embodiments, the molar input ratio of PEGylation agent to kynureninase homodimer is from about 17:1 to about 23:1, such as about 17:1, 18:1, 19:1, 20:1, 21:1, 22:1, or 23:1.

In some embodiments, the molar input ratio of PEGylation agent to kynureninase homodimer is from about 18:1 to about 22:1, such as about 18:1, 19:1, 20:1, 21:1, or 22:1.

In some embodiments, the molar input ratio of PEGylation agent to kynureninase homodimer is from about 19:1 to about 21:1, such as about 19:1, 20:1, or 21:1.

In some embodiments, the molar input ratio of PEGylation agent to kynureninase homodimer is about 20:1.

In some embodiments of either of the foregoing aspects of the disclosure, the PEG molecule has a molecular weight from about 1 kDa to about 10 kDa, such as about 1, 2, 3, 4, 5, 6, 7, 8, 9 or 10 kDa. In some embodiments, the PEG molecule has a molecular weight from about 2 kDa to about 9 kDa, such as about 2, 3, 4, 5, 6, 7, 8 or 9 kDa. In some embodiments, the PEG molecule has a molecular weight from about 3 kDa to about 8 kDa, such as about 3, 4, 5, 6, 7 or 8 kDa. In some embodiments, the PEG molecule has a molecular weight from about 4 kDa to about 7 kDa, such as about 4, 5, 6 or 7 kDa. In some embodiments, the PEG molecule has a molecular weight from about 5 kDa to about 6 kDa, such as about 5 or 6 kDa. In some embodiments, the PEG molecular has a molecular weight of about 5 kDa.

In some embodiments, the PEGylation agent is a lysine-reactive PEGylation agent, such as a PEGylation agent in which the PEG molecule is bound to a reactive group that contains an N-hydroxysuccinimide (NHS) moiety, among other lysine-reactive moieties described herein or known in the art.

In some embodiments, the PEGylation agent is a cysteine-reactive PEGylation agent, such as a PEGylation agent in which the PEG molecule is bound to a reactive group that contains an iodoacetamide moiety or a maleimide moiety, among other cysteine-reactive moieties described herein or known in the art.

In some embodiments, the homodimer is covalently bound to the PEG molecule by way of one or more lysine or cysteine residues, such as by one or more lysine residues by way of a linking group formed from reaction of a lysine amine with a succinimide group, an aldehyde group, an amide group, a carbamate group, an ester group, an epoxy group, a carboxyl group, a hydroxyl group, and combinations thereof. In some embodiments, the linking group is a succinimide group, such as a succinimidyl succinate, succinimidyl propionate, succinimidyl carboxymethylate, succinimidyl carbonate, succinimidyl succinamide, N-hydroxy succinimide or a combination thereof, such as an N-hydroxy succinimide carbonate. In some embodiments, the linking group is monofunctional.

In some embodiments, each polypeptide monomer has an amino acid sequence that is at least 85%, 86%, 87%, 88%, 89%, 90%, 91%, 92%, 93%, 94%, 95%, 96%, 97%, 98% or 99% identical to SEQ ID NO: 1, and wherein each polypeptide monomer has one or more amino acid substitutions, relative to SEQ ID NO: 1, selected from the group consisting of L8P, K38E, Y47L, I48F, K50Q, I51M, S60N, K64N, D65G, E66K, N67D, N67P, D67S, A68F, A68T, A68V, F71L, F71M, L72N, K84E, E88N, E89K, E89S, E90Q, D92E, K93N, K93T, A95H, A95Q, K96N, I97H, 197L, I97V, A98G, A99G, A99I, A99R, A99S, A99T, A99V, Y100N, Y100S, Y100T, G101A, H102W, E103F, E103H, E103N, E103Q, E103R, E103V, E103W, V104D, V104E, V104F, V104H, V104K, V104L, V104R, G105A, G105H, G105S, G105T, E106D, K106D, K106E, K106H, K106N, R107P, R107S, P108R, I110A, I110F, I110L, I110M, I110T, T111D, T111H, T111N, T111R, G112A, G112C, G112D, G112K, G112L, G112M, G112Q, G112R, G112S, G112T, G112Y, N127K, I131V, A132V, L133V, A136T, L137T, T138S, N140D, H142Q, Q14R, Y156H, K163T, D168E, H169R, Q175L, I183F, I183L, I183P, I183S, E184A, E184D, E184R, E184T, E184V, E185T, M187L, M189I, K191A, K191G, K191H, K191M, K191N, K191R, K191S, K191T, K191W, E197A, E197D, E197F, E197K, E197M, E197Q, E197S, E197T, E197V, I201C, I201E, I201F, I201H, I201L, I201S, I201T, I201V, H203K, L219M, L219W, F220L, V223I, F225Y, H230F, H230L, H230Y, N232S, Y246F, F249W, D250E, S274A, S274C, S274G, S274N, S274T, L278M, A280G, A280S, A280T, G281S, A282M, A282P, G284N, I285L, V303L, V303S, F306W, F306Y, S311N, K315E, D317E, D317K, I331C, I331L, I331N, I331S, I331T, I331V, N333T, P334N, P335T, L337T, L338A, L338Q, S341I, K373E, K373N, N375A, N375H, Y376C, Y376F, Y376L, K378G, K378P, K378Q, K378R, K380G, K380S, A382G, A382R, A382T, T383S, K384G, K384N, P386K, P386S, V387L, N389E, I405L, F407Y, S408D, S408N, N411R, D413S, D413V, Q416T, E419A, E419L, K420E, R421N, V424I, K427M, N429E, G432A, and A436T. In some embodiments, each polypeptide monomer has an amino acid sequence that is at least 90%, 91%, 92%, 93%, 94%, 95%, 96%, 97%, 98% or 99% identical to SEQ ID NO: 1. In some embodiments, each polypeptide monomer has an amino acid sequence that is at least 95%, 96%, 97%, 98% or 99% identical to SEQ ID NO: 1.

In some embodiments, each polypeptide monomer comprises a substitution at A282 (e.g., A282M or A282P), F306 (e.g., F306W or F306Y) or F249, such as F249W, relative to SEQ ID NO: 1. In some embodiments, each polypeptide monomer comprises a substitution at A99 relative to SEQ ID NO: 1. In some embodiments, each polypeptide monomer comprises a substitution at G112 relative to SEQ ID NO: 1. In some embodiments, each polypeptide monomer comprises a substitution at E103 relative to SEQ ID NO: 1. In some embodiments, each polypeptide monomer comprises a substitution at V104 relative to SEQ ID NO: 1. In some embodiments, each polypeptide monomer comprises a substitution at S408 relative to SEQ ID NO: 1. In some embodiments, each polypeptide monomer comprises the F306W substitution. In some embodiments, each polypeptide monomer comprises the L72N substitution. In some embodiments, each polypeptide monomer comprises the H102W and N333T substitutions. In some embodiments, each polypeptide monomer comprises the I183P substitution. In some embodiments, each polypeptide monomer comprises the R107P substitution. In some embodiments, each polypeptide monomer comprises the A436T substitution. In some embodiments, each polypeptide monomer comprises at least one substitution selected from L72N, H102W, A282P, F306W, I331S and N333T relative to SEQ ID NO: 1. In some embodiments, each polypeptide monomer comprises at least two, three, four or five substitutions selected from L72N, H102W, A282P, F306W, I331S and N333T relative to SEQ ID NO: 1. In some embodiments, each polypeptide monomer comprises the substitutions L72N, H102W, A282P, F306W, I331S and N333T relative to SEQ ID NO: 1.

In some embodiments, each polypeptide monomer has an amino acid sequence that is at least 85%, 86%, 87%, 88%, 89%, 88%, 89%, 90%, 91%, 92%, 93%, 94%, 95%, 96%, 97%, 98% or 99% identical to SEQ ID NO: 3. In some embodiments, each polypeptide monomer has an amino acid sequence that is at least 90%, 91%, 92%, 93%, 94%, 95%, 96%, 97%, 98% or 99% identical to SEQ ID NO: 3. In some embodiments, each polypeptide monomer has an amino acid sequence that is at least 95%, 96%, 97%, 98% or 99% identical to SEQ ID NO: 3. In some embodiments, each polypeptide monomer has the amino acid sequence of SEQ ID NO: 3.

In some embodiments, each polypeptide monomer has an amino acid sequence that is at least 85%, 86%, 87%, 88%, 89%, 88%, 89%, 90%, 91%, 92%, 93%, 94%, 95%, 96%, 97%, 98% or 99% identical to SEQ ID NO: 2. In some embodiments, each polypeptide monomer has an amino acid sequence that is at least 90%, 91%, 92%, 93%, 94%, 95%, 96%, 97%, 98% or 99% identical to SEQ ID NO: 2. In some embodiments, each polypeptide monomer has an amino acid sequence that is at least 95%, 96%, 97%, 98% or 99% identical to SEQ ID NO: 2. In some embodiments, each polypeptide monomer has the amino acid sequence of SEQ ID NO: 2.

In some embodiments, the homodimer has a catalytic activity ($k_{cat}/K_M$) of at least 8000 $M^{-1}$ $s^{-1}$. In some embodiments, the homodimer has a catalytic activity ($k_{cat}/K_M$) of between about 8000 $M^{-1}$ $s^{-1}$ and 40000 $M^{-1}$ $s^{-1}$; 10000$M^{-1}$ $s^{-1}$ and 40000 $M^{-1}$ $s^{-1}$; 20000$M^{-1}$ $s^{-1}$ and 40000 $M^{-1}$ $s^{-1}$; or 25000$M^{-1}$ $s^{-1}$ and 35000 $M^{-1}$ $s^{-1}$.

In some embodiments of any of the foregoing aspects of the disclosure, the ratio of PEG molecules to homodimer is about 25:1, the PEG molecule has a molecular weight of about 5 kDa and is bound to the homodimer by way of an N-hydroxysuccinimide ester carbonate linking group.

In some embodiments, the homodimer is contacted with the PEGylation agent in an aqueous buffer, such as sodium diphosphate or sodium acetate. In some embodiments, the aqueous buffer ranges in pH from about 7.5 to about 9.5, such as 7.5, 7.6, 7.8, 7.9, 8.0, 8.1, 8.2, 8.3, 8.4, 8.5, 8.6, 8.7, 8.8, 8.9, 9.0, 9.1, 9.2, 9.3, 9.4 or 9.5. In some embodiments, the aqueous buffer ranges in ionic strength from about 250 mM to about 350 mM. In some embodiments, size exclusion chromatography is used to isolate the homodimer.

In some embodiments of any of the above aspects or embodiments of the disclosure, the kynureninase homodimer may contain one or more of the amino acid substitutions disclosed in WO2015/031771, WO2016/033488 or WO2017/151860, each of which is incorporated herein by reference in its entirety.

A modified polypeptide as discussed above and herein may be characterized as having a certain percentage of identity as compared to an unmodified polypeptide (e.g., a native polypeptide, such as human kynureninase of SEQ ID NO: 1) or to any polypeptide sequence disclosed herein. For example, the unmodified polypeptide may comprise at least, or up to, about 150, 200, 250, 300, 350, 400, 450 or 465 residues (or any range derivable therein) of a native kynureninase. The percentage identity may be about, at most or at least 65%, 70%, 75%, 80%, 85%, 90%, 95%, 96%, 97%, 98%, or 99% (or any range derivable therein) between the modified and unmodified polypeptides, or between any two sequences in comparison. It is also contemplated that percentage of identity discussed above may relate to a particular modified region of a polypeptide as compared to an unmodified region of a polypeptide. For instance, a polypeptide may contain a modified or mutant substrate recognition site of a kynureninase that can be characterized based on the identity of the amino acid sequence of the modified or mutant substrate recognition site of the kynureninase to that of an unmodified or mutant kynureninase from the same species or across the species. A modified or mutant human polypeptide characterized, for example, as having at least 90% identity to an unmodified kynureninase means that at least 90% of the amino acids in that modified or mutant human polypeptide are identical to the amino acids in the unmodified polypeptide.

Such an unmodified polypeptide may be a native kynureninase, particularly a human isoform or other primate isoforms. For example, the native human kynureninase may have the sequence of SEQ ID NO: 1. Non-limiting examples of other native primate kynureninase include *Pongo abelii* kynureninase (Genbank ID: XP_009235962.1, GI: 686708656), *Macaca fascicularis* kynureninase (Genbank ID: EHH54849.1, GI: 355750522), and *Pan troglodytes* kynureninase (Genbank ID: XP_003309314.1, GI: 332814521). Exemplary native polypeptides include a sequence having about, at most or at least 65%, 70%, 75%, 80%, 85%, 90%, 95%, 96%, 97%, 98%, 99% or 100% identity (or any range derivable therein) of SEQ ID NO:1. For example, the native polypeptide may comprise at least or up to about 10, 20, 30, 40, 50, 60, 70, 80, 90, 100, 150, 200, 250, 300, 350, 400, 450 or 465 residues (or any range derivable therein) of the sequence of SEQ ID NO:1.

In another aspect, the disclosure comprises a pharmaceutical formulation comprising the kynureninase homodimer of any one of compositions described above in a pharmaceutically acceptable carrier. In some embodiments, the pharmaceutical formulation comprises the kynureninase homodimer of any one of compositions described above in a pharmaceutically acceptable carrier.

In another aspect, the disclosure features a method of treating a subject (e.g. a mammalian subject, such as a human subject) having a tumor comprising administering to a subject an effective amount of the formulation described herein or the enzyme with any one of the compositions described herein. In some embodiments, the method comprises administering to a subject an effective amount of the formulation described herein or the enzyme with any one of the compositions described herein In some embodiments, the subject has been identified as having an IDO1, IDO2, or TDO expressing tumor, such as a solid tumor or a hematological tumor. In some embodiments, the subject is a human subject.

In some embodiments, the formulation is administered intratumorally, intravenously, intradermally, intraarterially, intraperitoneally, intralesionally, intracranially, intraarticularly, intraprostaticaly, intrapleurally, intratracheally, intraocularly, intranasally, intravitreally, intravaginally, intrarectally, intramuscularly, subcutaneously, subconjunctival, intravesicularlly, mucosally, intrapericardially, intraumbilically, orally, by inhalation, by injection, by infusion, by continuous infusion, by localized perfusion bathing target cells directly, via a catheter, or via a lavage.

In some embodiments, the method also comprises administering a second anticancer therapy to the subject. The second anticancer therapy may be a surgical therapy, chemotherapy, radiation therapy, cryotherapy, hormone therapy, immunotherapy or cytokine therapy. In some embodiments, the second anticancer therapy may be an immune checkpoint inhibitor therapy. For example, a kynureninase homodimer may be admixed, conjugated, administered with, or administered separately from, an immunotherapy agent, for instance, for the treatment of a cancer or infectious disease, such as a cancer or infectious disease described herein. Exemplary immunotherapy agents useful in conjunction with the compositions and methods described herein include, without limitation, an anti-CTLA-4 agent, an anti-PD-1 agent, an anti-PD-L1 agent, an anti-PD-L2 agent, an anti-TNF-α cross-linking agent, an anti-TRAIL cross-linking agent, an anti-CD27 agent, an anti-CD30 agent, an anti-CD40 agent, an anti-4-1 BB agent, an anti-GITR agent, an anti-OX40 agent, an anti-TRAILR1 agent, an anti-TRAILR2 agent, and an anti-TWEAKR agent, as well as, for example, agents directed toward the immunological targets described in Table 1 of Mahoney et al., Cancer Immunotherapy, 14:561-584 (2015), the disclosure of which is incorporated herein by reference in its entirety. For example, the immunotherapy agent may be an anti-CTLA-4 antibody or antigen-binding fragment thereof, such as ipilimumab and tremelimumab. The immunotherapy agent may be an anti-PD-1 antibody or antigen-binding fragment thereof, such as nivolumab, pembrolizumab, avelumab, durvalumab, and atezolizumab. The immunotherapy agent may be an anti-PD-L1 antibody or antigen-binding fragment thereof, such as atezolizumab or avelumab. As other examples, immunological target 4-1 BB ligand may be targeted with an anti-4-1 BB ligand antibody; immunological target OX40L may be targeted with an anti-OX40L antibody; immunological target GITR may be targeted with an anti-GITR antibody; immunological target CD27 may be targeted with an anti-CD27 antibody; immunological target TL1A may be targeted with an anti-TL1A antibody; immunological target CD40L or CD40 may be targeted with an anti-CD40L antibody; immunological target LIGHT may be targeted with an anti-LIGHT antibody; immunological target BTLA may be targeted with an anti-BTLA antibody; immunological target LAG3 may be targeted with an anti-LAG3 antibody; immunological target TIM3 may be targeted with an anti-TIM3 antibody; immunological target Singlecs may be targeted with an anti-Singlecs antibody; immunological target ICOS ligand may be targeted with an anti-ICOS ligand antibody; immunological target B7-H3 may be targeted with an anti-B7-H3 antibody; immunological target B7-H4 may be targeted with an anti-B7-H4 antibody; immunological target VISTA may be targeted with an anti-VISTA antibody; immunological target TMIGD2 may be targeted with an anti-TMIGD2 antibody; immunological target BTNL2 may be targeted with an anti-BTNL2 antibody; immunological target CD48 may be targeted with an anti-CD48 antibody; immunological target KIR may be targeted with an anti-KIR antibody; immunological target LIR may be targeted with an anti-LIR antibody; immunological target ILT may be targeted with an anti-ILT antibody; immunological target NKG2D may be targeted with an anti-NKG2D antibody; immunological target NKG2A may be targeted with an anti-NKG2A antibody; immunological target MICA may be targeted with an anti-MICA antibody; immunological target MICB may be targeted with an anti-MICB antibody; immunological target CD244 may be targeted with an anti-CD244 antibody; immunological target CSF1R may be targeted with an anti-CSF1R antibody; immunological target IDO may be targeted with an anti-IDO antibody; immunological target TGFβ may be targeted with an anti-TGFβ antibody; immunological target CD39 may be targeted with an anti-CD39 antibody; immunological target CD73 may be targeted with an anti-CD73 antibody; immunological target CXCR4 may be targeted with an anti-CXCR4 antibody; immunological target CXCL12 may be targeted with an anti-CXCL12 antibody; immunological target SIRPA may be targeted with an anti-SIRPA antibody; immunological target CD47 may be targeted with an anti-CD47 antibody; immunological target VEGF may be targeted with an anti-VEGF antibody; and immunological target neuropilin may be targeted with an anti-neuropilin antibody (see, e.g., Table 1 of Mahoney et al.).

Immunotherapy agents that may be used in conjunction with the compositions and methods described herein include, for instance, an anti-TWEAK agent, an anti-cell surface lymphocyte protein agent, an anti-BRAF agent, an anti-MEK agent, an anti-CD33 agent, an anti-CD20 agent, an anti-HLA-DR agent, an anti-HLA class I agent, an anti-CD52 agent, an anti-A33 agent, an anti-GD3 agent, an anti-PSMA agent, an anti-Ceacan 1 agent, an anti-Galedin 9 agent, an anti-HVEM agent, an anti-VISTA agent, an anti-B7 H4 agent, an anti-HHLA2 agent, an anti-CD155 agent, an anti-CD80 agent, an anti-BTLA agent, an anti-CD160 agent, an anti-CD28 agent, an anti-CD226 agent, an anti-CEACAM1 agent, an anti-TIM3 agent, an anti-TIGIT agent, an anti-CD96 agent, an anti-CD70 agent, an anti-CD27 agent, an anti-LIGHT agent, an anti-CD137 agent, an anti-DR4 agent, an anti-CR5 agent, an anti-TNFRS agent, an anti-TNFR1 agent, an anti-FAS agent, an anti-CD95 agent, an anti-TRAIL agent, an anti-DR6 agent, an anti-EDAR agent, an anti-NGFR agent, an anti-OPG agent, an anti-RANKL agent, an anti-LTβ receptor agent, an anti-BCMA agent, an anti-TACI agent, an anti-BAFFR agent, an anti-EDAR2 agent, an anti-TROY agent, and an anti-RELT agent. For instance, the immunotherapy agent may be an anti-TWEAK antibody or antigen-binding fragment thereof, an anti-cell surface lymphocyte protein antibody or antigen-binding fragment thereof, an anti-BRAF antibody or antigen-binding fragment thereof, an anti-MEK antibody or antigen-binding fragment thereof, an anti-CD33 antibody or antigen-binding fragment thereof, an anti-CD20 antibody or antigen-binding fragment thereof, an anti-HLA-DR antibody or antigen-binding fragment thereof, an anti-HLA class I antibody or antigen-binding fragment thereof, an anti-CD52 antibody or antigen-binding fragment thereof, an anti-A33 antibody or antigen-binding fragment thereof, an anti-GD3 antibody or antigen-binding fragment thereof, an anti-PSMA antibody or antigen-binding fragment thereof, an anti-Ceacan 1 antibody or antigen-binding fragment thereof, an anti-Galedin 9 antibody or antigen-binding fragment thereof, an anti-HVEM antibody or antigen-binding fragment thereof, an anti-VISTA antibody or antigen-binding fragment thereof, an anti-B7 H4 antibody or antigen-binding fragment thereof, an anti-HHLA2 antibody or antigen-binding fragment thereof, an anti-CD155 antibody or antigen-binding fragment thereof, an anti-CD80 antibody or antigen-binding fragment thereof, an anti-BTLA antibody or antigen-binding fragment thereof, an anti-CD160 antibody or antigen-binding fragment thereof, an anti-CD28 antibody or antigen-binding fragment thereof, an anti-CD226 antibody or antigen-binding fragment thereof, an anti-CEACAM1 antibody or antigen-binding fragment thereof, an anti-TIM3 antibody or antigen-binding fragment thereof, an anti-TIGIT antibody or antigen-binding fragment thereof, an anti-CD96 antibody or antigen-binding fragment thereof, an anti-CD70 antibody or antigen-binding fragment thereof, an anti-CD27 antibody or antigen-binding fragment thereof, an anti-LIGHT antibody or antigen-binding fragment thereof, an anti-CD137 antibody or antigen-binding fragment thereof, an anti-DR4 antibody or antigen-binding fragment thereof, an anti-CR5 antibody or antigen-binding fragment thereof, an anti-TNFRS antibody or antigen-binding fragment thereof, an anti-TNFR1 antibody or antigen-binding fragment thereof, an anti-FAS antibody or antigen-binding fragment thereof, an anti-CD95 antibody or antigen-binding fragment thereof, an anti-TRAIL antibody or antigen-binding fragment thereof, an anti-DR6 antibody or antigen-binding fragment thereof, an anti-EDAR antibody or antigen-binding fragment thereof, an anti-NGFR antibody or antigen-binding fragment thereof, an anti-OPG antibody or antigen-binding fragment thereof, an anti-RANKL antibody or antigen-binding fragment thereof, an anti-LTβ receptor antibody or antigen-binding fragment thereof, an anti-BCMA antibody or antigen-binding fragment thereof, an anti-TACI antibody or antigen-binding fragment thereof, an anti-BAFFR antibody or antigen-binding fragment thereof, an anti-EDAR2 antibody or antigen-binding fragment thereof, an anti-TROY antibody or antigen-binding fragment thereof, or an anti-RELT antibody or antigen-binding fragment thereof.

In some embodiments, the second anticancer therapy is an immunotherapy such as administering immune effector cells or an immunogenic composition. For example, the immunogenic composition can comprise cancer cells antigens and, optionally, an adjuvant. In some embodiments, immune effector cells can comprise NK-cells, T-cells (e.g., CAR T-cells) or NK/T-cells. In some embodiments, a T cell comprising a chimeric antigen receptor (CAR) and a kynureninase homodimer of the embodiments are contemplated for use in treating a subject with cancer. In some embodiments, the cell may be transfected with a DNA encoding the CAR and the kynureninase and, in some cases, a transposase.

In some embodiments, the disclosure provides a method of providing a T-cell response in a human subject having a tumor, the method comprising administering to the subject a kynureninase homodimer in accordance with any one of the embodiments of methods of treatment described above.

Definitions

As used herein, the term "about" refers to a value that is within 10% above or below the value being described. For instance, the phrase "about 5,000 Da" refers to a value between and including 4,500 Da and 5,500 Da.

As used herein, the terms "administering," "administration," and the like refer to directly giving a patient a therapeutic agent (e.g., a formulation), that together express one or more proteins described herein by any effective route. Exemplary routes of administration are described herein and include systemic administration routes, such as intravenous injection, as well as routes of administration directly to the central nervous system of the patient, such as by way of intracerebroventricular injection, intrathecal injection, and stereotactic injection, among others.

As used herein, the term "biologically functional equivalent" is well understood in the art and is further defined in detail herein. Accordingly, sequences that have between about 70% and about 80%, or between about 81% and about 90%, or even between about 91% and about 99% of amino acids that are identical or functionally equivalent to the amino acids of a control polypeptide are included, provided the biological activity of the protein is maintained. A modified protein may be biologically functionally equivalent to its native counterpart in some embodiments.

As used herein in the context of a protein of interest, the term "catalytic activity" refers to the biological functionality that is associated with a wild-type form of the protein. For example, in the context of an enzyme, the term "catalytic activity" refers to the ability of the protein to effectuate substrate turnover in a manner that yields the product of a corresponding chemical reaction. Activity levels of enzymes can be detected and quantitated, for example, using substrate turnover assays known in the art. As another example, in the context of a membrane-bound receptor, the term "activity" may refer to signal transduction initiated by the receptor, e.g., upon binding to its cognate ligand.

The term "chimeric antigen receptors (CARs)," as used herein, may refer to artificial T-cell receptors, chimeric T-cell receptors, or chimeric immunoreceptors, for example, and encompass engineered receptors that graft an artificial specificity onto a particular immune effector cell. CARs may be employed to impart the specificity of a monoclonal antibody onto a T cell, thereby allowing a large number of specific T cells to be generated, for example, for use in adoptive cell therapy. In specific embodiments, CARs direct specificity of the cell to a tumor associated antigen, for example. In some embodiments, CARs comprise an intracellular activation domain, a transmembrane domain, and an extracellular domain comprising a tumor associated antigen binding region. In particular embodiments, CARs comprise fusions of single-chain variable fragments (scFv) derived from monoclonal antibodies (such as those described in U.S. Pat. No. 7,109,304, which is incorporated herein by reference in its entirety), fused to CD3-zeta transmembrane and endodomains. The specificity of other CAR designs may be derived from ligands of receptors (e.g., peptides) or from pattern-recognition receptors, such as Dectins. In particular embodiments, one can target malignant B cells by redirecting the specificity of T cells by using a CAR specific for the B-lineage molecule, CD19. In certain cases, the spacing of the antigen-recognition domain can be modified to reduce activation-induced cell death. In certain cases, CARs comprise domains for additional co-stimulatory signaling, such as CD3-zeta, FcR, CD27, CD28, CD137, DAP10, and/or OX40. In some cases, molecules can be co-expressed with the CAR, including co-stimulatory molecules, reporter genes for imaging (e.g., for positron emission tomography), gene products that conditionally ablate the T cells upon addition of a pro-drug, homing receptors, chemokines, chemokine receptors, cytokines, and cytokine receptors.

As used herein, the term "homodimer" refers to a protein (e.g. kynureninase) comprising two polypeptide chains that are identical to each other with respect to order, number, and kind of amino acid residues. Accordingly, the term "kynureninase homodimer" refers to a kynureninase comprising two monomeric kynureninase polypeptide chains that are identical to each other with respect to order, number, and kind of amino acid residues.

As used herein, the terms "conservative mutation," "conservative substitution," "conservative amino acid substitution," and the like refer to a substitution of one or more amino acids for one or more different amino acids that exhibit similar physicochemical properties, such as polarity, electrostatic charge, and steric volume. These properties are summarized for each of the twenty naturally-occurring amino acids in Table 1 below.

TABLE 1

Properties of Amino Acids and Corresponding Side Chains

| Amino Acid | 3 Letter Code | 1 Letter Code | Side-chain Polarity | Electrostatic character at physiological pH (7.4) | Steric Volume† |
|---|---|---|---|---|---|
| Alanine | Ala | A | nonpolar | neutral | small |
| Arginine | Arg | R | polar | cationic | large |
| Asparagine | Asn | N | polar | neutral | intermediate |
| Aspartic acid | Asp | D | polar | anionic | intermediate |
| Cysteine | Cys | C | nonpolar | neutral | intermediate |
| Glutamic acid | Glu | E | polar | anionic | intermediate |
| Glutamine | Gln | Q | polar | neutral | intermediate |
| Glycine | Gly | G | nonpolar | neutral | small |
| Histidine | His | H | polar | Both neutral and cationic forms in equilibrium at pH 7.4 | large |
| Isoleucine | Ile | I | nonpolar | neutral | large |
| Leucine | Leu | L | nonpolar | neutral | large |
| Lysine | Lys | K | polar | cationic | large |
| Methionine | Met | M | nonpolar | neutral | large |
| Phenylalanine | Phe | F | nonpolar | neutral | large |
| Proline | Pro | P | nonpolar | neutral | intermediate |
| Serine | Ser | S | polar | neutral | small |
| Threonine | Thr | T | polar | neutral | intermediate |
| Tryptophan | Trp | W | nonpolar | neutral | bulky |
| Tyrosine | Tyr | Y | polar | neutral | large |
| Valine | Val | V | nonpolar | neutral | intermediate |

†based on volume in $A^3$: 50-100 is small, 100-150 is intermediate, 150-200 is large, and >200 is bulky As used herein, the terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

As used herein, the terms "effective amount," "therapeutically effective amount," and the like, when used in reference to a therapeutic composition, such as a vector construct, viral vector, or cell described herein, refer to a quantity sufficient to, when administered to the subject, including a mammal, for example a human, effect beneficial or desired results, such as clinical results. For example, in the context of treating cancer, described herein, these terms refer to an amount of the composition sufficient to achieve a treatment response as compared to the response obtained without administration of the composition, vector construct, viral vector or cell. The quantity of a given composition described herein that will correspond to such an amount may vary depending upon various factors, such as the given agent, the pharmaceutical formulation, the route of administration, the type of disease or disorder, the identity of the subject (e.g., age, sex, weight) or host being treated, and the like. An "effective amount," "therapeutically effective amount," or the like, of a composition, such as a vector construct, viral vector, or cell of the present disclosure, also include an amount that results in a beneficial or desired result in a subject as compared to a control.

As used herein, the term "fusion protein" refers to a chimeric protein containing proteins or protein fragments operably linked in a non-native way.

As used herein, the term "half-life" (½-life) refers to the time that would be required for the concentration of a polypeptide thereof to fall by half in vitro or in vivo, for example, after injection in a mammal.

The term "$K_M$" as used herein refers to the Michaelis-Menten constant for an enzyme and is defined as the concentration of the specific substrate at which a given enzyme yields one-half its maximum velocity in an enzyme catalyzed reaction. The term "$k_{cat}$" as used herein refers to the turnover number or the number of substrate molecules each enzyme site converts to product per unit time, and in which the enzyme is working at maximum efficiency. The term "$k_{cat}/K_M$" as used herein is the specificity constant, which is a measure of how efficiently an enzyme converts a substrate into product.

As used herein, the term "kynureninase" refers to an enzyme responsible for the catalytic degradation of kynurenine to anthranilic acid. The terms "kynureninase" also refer to variants of wild-type kynureninase enzymes and nucleic acids encoding the same, such as variant proteins having at least 70% sequence identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.9% identity, or more) to the amino acid sequence of a wild-type kynureninase enzyme (e.g., SEQ ID NO: 1) or polynucleotides having at least 70% sequence identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.9% identity, or more) to the nucleic acid sequence of a wild-type kynurenine gene, provided that the kynureninase analog encoded retains the therapeutic function of wild-type kynureninase. "Kynureninase" may also refer to a kynureninase protein in which the natural signal peptide is present. Alternatively, "kynureninase" may refer to a kynureninase protein in which the natural signal peptide has been removed (e.g., the mature protein). Kynureninase may also refer to the catalytic domain of kynureninase, or a variant having at least 70% sequence identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.9% identity, or more) to such a domain. Additionally, the term "kynureninase" also includes variants in which the polypeptide is operably linked to another agent, such as another polypeptide, half-life-modifying agent, such as a PEGylation agent, or therapeutic agent. As used herein, a "kynureninase" may refer to the enzyme or the gene encoding this protein, depending upon the context, as will be appreciated by one of skill in the art.

A kynureninase may exist as a dimer of individual "kynureninase monomers," such as a homodimer composed of two kynureninase monomers that each have the same amino acid sequence. The term "kynureninase monomer" as used herein refers to an individual polypeptide that, when noncovalently joined with another such polypeptide, forms a dimeric kynureninase enzyme. Kynureninase monomers of the disclosure may have an amino acid sequence that is, for example, at least 85% identical (e.g., 85%, 86%, 87%, 88%, 89%, 90%, 91%, 92%, 93%, 94%, 95%, 96%, 97%, 98%, 99%, or 100% identical) to SEQ ID NO: 1, SEQ ID NO: 2, or SEQ ID NO: 3 herein. In some embodiments, kynureninase monomers of the disclosure have one or more amino acid substitutions relative to SEQ ID NO: 1, such as an amino acid substitution selected from the group consisting of L8P, K38E, Y47L, I48F, K50Q, I51M, S60N, K64N, D65G, E66K, N67D, N67P, D67S, A68F, A68T, A68V, F71L, F71M, L72N, K84E, E88N, E89K, E89S, E90Q, D92E, K93N, K93T, A95H, A95Q, K96N, 197H, 197L, I97V, A98G, A99G, A99I, A99R, A99S, A99T, A99V, Y100N, Y100S, Y100T, G101A, H102W, E103F, E103H, E103N, E103Q, E103R, E103V, E103W, V104D, V104E, V104F, V104H, V104K, V104L, V104R, G105A, G105H, G105S, G105T, E106D, K106D, K106E, K106H, K106N, R107P, R107S, P108R, I110A, I110F, I110L, I110M, I110T, T111D, T111H, T111N, T111R, G112A, G112C, G112D, G112K, G112L, G112M, G112Q, G112R, G112S, G112T, G112Y, N127K, I131V, A132V, L133V, A136T, L137T, T138S, N140D, H142Q, Q14R, Y156H, K163T, D168E, H169R, Q175L, I183F, I183L, I183P, I183S, E184A, E184D, E184R, E184T, E184V, E185T, M187L, M189I, K191A, K191G, K191H, K191M, K191N, K191R, K191S, K191T, K191W, E197A, E197D, E197F, E197K, E197M, E197Q, E197S, E197T, E197V, I201C, I201E, I201F, I201H, I201L, I201S, I201T, I201V, H203K, L219M, L219W, F220L, V223I, F225Y, H230F, H230L, H230Y, N232S, Y246F, F249W, D250E, S274A, S274C, S274G, S274N, S274T, L278M, A280G, A280S, A280T, G281S, A282M, A282P, G284N, I285L, V303L, V303S, F306W, F306Y, S311N, K315E, D317E, D317K, I331C, I331L, I331N, I331S, I331T, I331V, N333T, P334N, P335T, L337T, L338A, L338Q, S341I, K373E, K373N, N375A, N375H, Y376C, Y376F, Y376L, K378G, K378P, K378Q, K378R, K380G, K380S, A382G, A382R, A382T, T383S, K384G, K384N, P386K, P386S, V387L, N389E, I405L, F407Y, S408D, S408N, N411R, D413S, D413V, Q416T, E419A, E419L, K420E, R421N, V424I, K427M, N429E, G432A, and A436T. Kynureninase monomers of the disclosure may have, for example, a substitution at A282 (e.g., A282M or A282P), F306 (e.g., F306W or F306Y) or F249, such as F249W, relative to SEQ ID NO: 1. In some embodiments, kynureninase monomers of the disclosure comprise a substitution at A99 relative to SEQ ID NO: 1. In some embodiments, kynureninase monomers of the disclosure comprise a substitution at G112 relative to SEQ ID NO: 1. In some embodiments, kynureninase monomers of the disclosure comprise a substitution at E103 relative to SEQ ID NO: 1. In some embodiments, kynureninase monomers of the disclosure comprise a substitution at V104 relative to SEQ ID NO: 1. In some embodiments, kynureninase monomers of the disclosure comprise a substitution at S408 relative to SEQ ID NO: 1. In some embodiments, kynureninase monomers of the disclosure comprise the F306W substitution. In some embodiments, kynureninase monomers of the disclosure comprise the L72N substitution. In some embodiments, kynureninase monomers of the disclosure comprise the H102W and N333T substitutions. In some embodiments, kynureninase monomers of the disclosure comprise the I183P substitution. In some embodiments, kynureninase monomers of the disclosure comprise the R107P substitution. In some embodiments, kynureninase monomers of the disclosure comprise the A436T substitution. In some embodiments, kynureninase monomers of the disclosure comprise at least one substitution selected from L72N, H102W, A282P, F306W, I331S and N333T relative to SEQ ID NO: 1. In some embodiments, kynureninase monomers of the disclosure comprise at least two, three, four or five substitutions selected from L72N, H102W, A282P, F306W, I331S and N333T relative to SEQ ID NO: 1. In some embodiments, kynureninase monomers of the disclosure comprise the substitutions L72N, H102W, A282P, F306W, I331S and N333T relative to SEQ ID NO: 1.

As used herein, the term "linking group" refers to a compound or moiety thereof that acts as a molecular bridge to operably link two different molecules, wherein one portion of the linking group is operably linked to a first molecule, and wherein another portion of the linking group is operably linked to a second molecule.

As used herein, the term "modified protein" or a "modified polypeptide," includes, for example, a protein or polypeptide that possesses an additional advantage over the unmodified protein or polypeptide, such as kynurenine degrading activity or thermodynamic stability.

As used herein, the term "monomer" refers to a single polypeptide chain that is the simplest base subunit for the further quaternary structure of a protein.

As used herein, the term "PEGylation agent" refers a polyethylene glycol (PEG). molecule that can be coupled (e.g., covalently linked) to an active agent, for example, through the hydroxy groups at the end of the PEG chain by way of various chemical methods to a protein. In some embodiments, PEG itself is limited to at most two active agents per PEG molecule. In a different approach, copolymers of PEG and amino acids can be used that retain the biocompatibility of PEG, but that have the added advantage of numerous attachment points per molecule, thus providing greater drug loading.

As used herein, "percent (%) sequence identity" with respect to a reference polynucleotide or polypeptide sequence is defined as the percentage of nucleic acids or amino acids in a candidate sequence that are identical to the nucleic acids or amino acids in the reference polynucleotide or polypeptide sequence, after aligning the sequences and introducing gaps, if necessary, to achieve the maximum percent sequence identity. Alignment for purposes of determining percent nucleic acid or amino acid sequence identity can be achieved in various ways that are within the capabilities of one of skill in the art, for example, using publicly available computer software such as BLAST, BLAST-2, or Megalign software. Those skilled in the art can determine appropriate parameters for aligning sequences, including any algorithms needed to achieve maximal alignment over the full length of the sequences being compared. For example, percent sequence identity values may be generated using the sequence comparison computer program BLAST. As an illustration, the percent sequence identity of a given nucleic acid or amino acid sequence, A, to, with, or against a given nucleic acid or amino acid sequence, B, (which can alternatively be phrased as a given nucleic acid or amino acid sequence, A that has a certain percent sequence identity to, with, or against a given nucleic acid or amino acid sequence, B) is calculated as follows:

100 multiplied by (the fraction X/Y)

where X is the number of nucleotides or amino acids scored as identical matches by a sequence alignment program (e.g., BLAST) in that program's alignment of A and B, and where Y is the total number of nucleic acids in B. It will be appreciated that where the length of nucleic acid or amino acid sequence A is not equal to the length of nucleic acid or amino acid sequence B, the percent sequence identity of A to B will not equal the percent sequence identity of B to A.

As used herein, the term "pharmaceutically acceptable" refers to those compounds, materials, compositions and/or dosage forms, which are suitable for contact with the tissues of a subject, such as a mammal (e.g., a human) without excessive toxicity, irritation, allergic response and other problem complications commensurate with a reasonable benefit/risk ratio.

As used herein the terms "protein" and "polypeptide" refer to compounds comprising amino acids joined by way of a peptide bonds and are used interchangeably.

As used herein, "subject" and "patient" refer to either a human or non-human, such as primates, mammals, and vertebrates. In particular embodiments, the subject is a human.

As used herein, "treatment" and "treating" refer to an approach for obtaining beneficial or desired results, e.g., clinical results. Beneficial or desired results can include, but are not limited to, alleviation or amelioration of one or more symptoms or conditions; diminishment of extent of disease or condition; stabilized (i.e., not worsening) state of disease, disorder, or condition; preventing spread of disease or condition; delay or slowing the progress of the disease or condition; amelioration or palliation of the disease or condition; and remission (whether partial or total), whether detectable or undetectable. "Ameliorating" or "palliating" a disease or condition means that the extent and/or undesirable clinical manifestations of the disease, disorder, or condition are lessened and/or time course of the progression is slowed or lengthened, as compared to the extent or time course in the absence of treatment. "Treatment" can also mean prolonging survival as compared to expected survival if not receiving treatment. Those in need of treatment include those already with the condition or disorder, as well as those prone to or at risk of developing the condition or disorder, as well as those in which the condition or disorder is to be prevented.

As used herein, the term "unit dose" when used in reference to a therapeutic composition refers to physically discrete units suitable as unitary dosage for the subject, each unit containing a predetermined quantity of active material calculated to produce the desired therapeutic effect in association with the required diluent, i.e., carrier, or vehicle.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

All molar input ratios shown in FIGS. 1A-1F are input ratios of PEG to kynureninase homodimer.

Figure 2A:
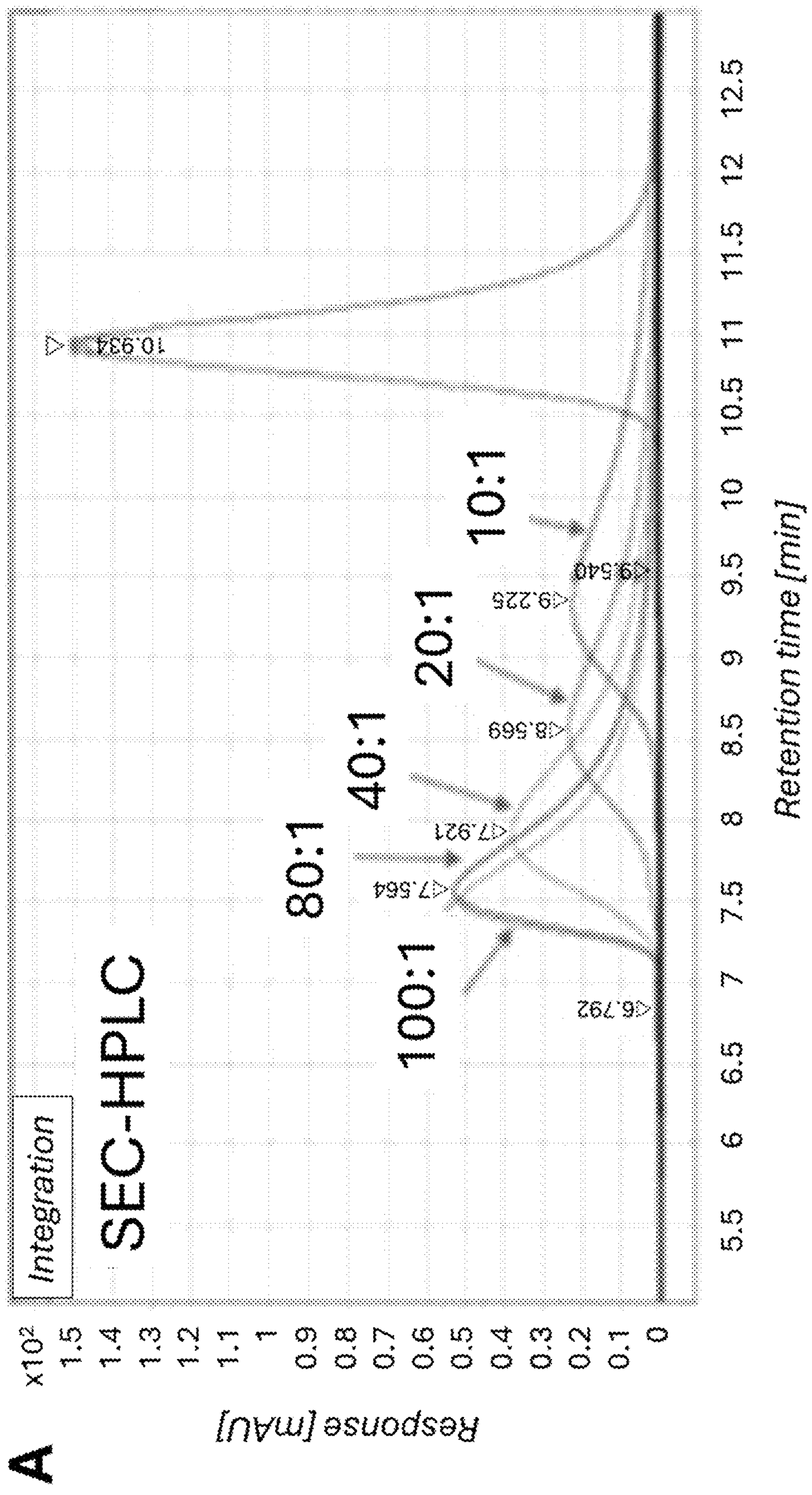
Figure 2B:
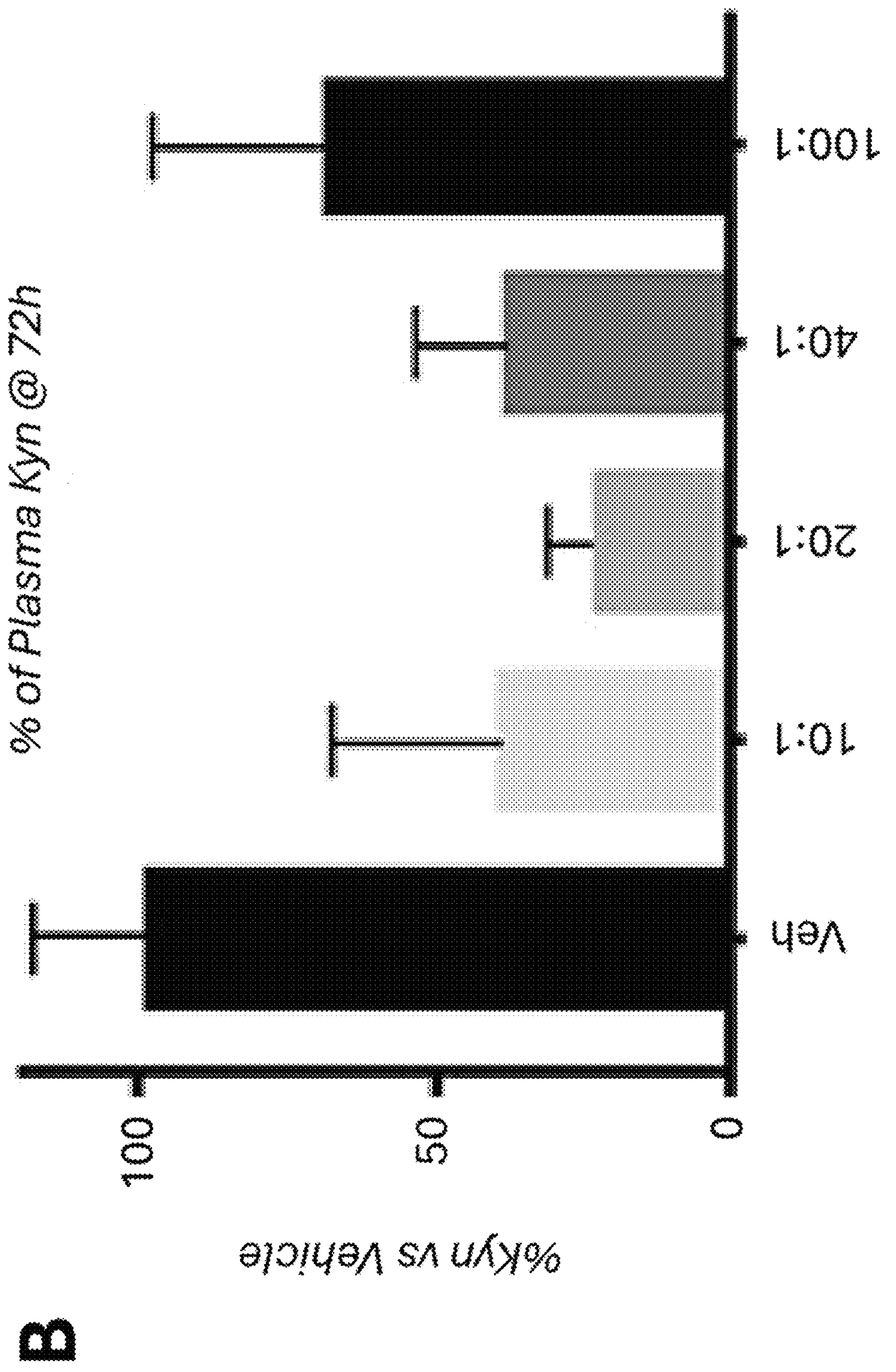
Figure 2C:
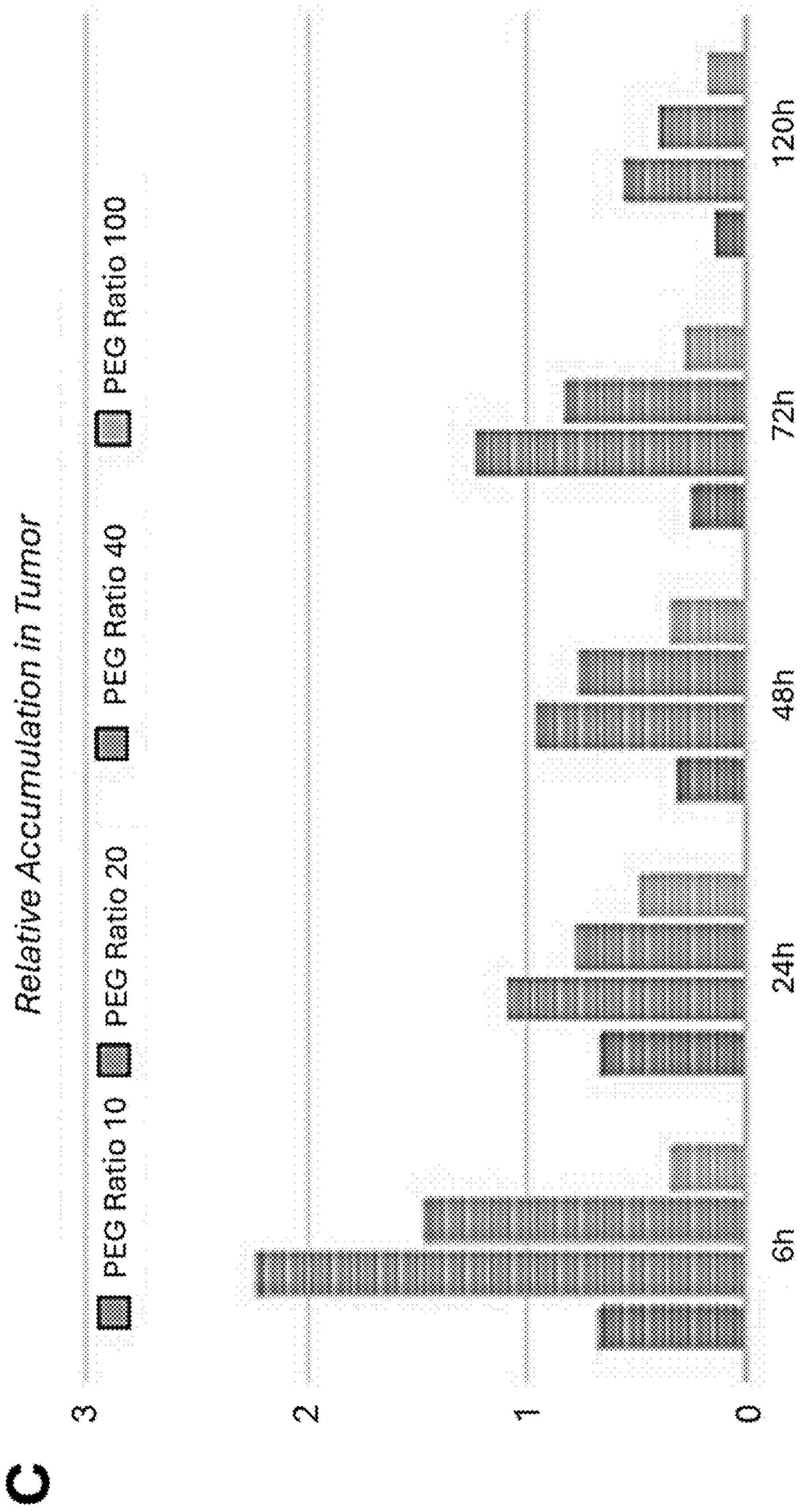

FIGS. 2A-2C: Comparison of biological activities of PEGylated kynureninase enzymes. A) SEC-HPLC profile of kynureninase with different input ratios (shown as PEG: kynureninase homodimer). Peaks, from left to right, correspond to 100:1 molar input ratio of PEG:kynureninase homodimer, 80:1 molar input ratio of PEG:kynureninase homodimer, 40:1 molar input ratio of PEG:kynureninase homodimer, 20:1 molar input ratio of PEG:kynureninase homodimer, 10:1 molar input ratio of PEG:kynureninase homodimer, and un-PEGylated kynureninase homodimer, respectively. B) Mouse plasma PD at 72 hrs after a single iv dose of PEGylated kynureninase. Values along the x-axis correspond to molar input ratios of PEG:kynureninase homodimer. C) CT26 tumor accumulation of PEGylated kynureninase as quantitated by anti-PEG Western Blot. Values along the x-axis represent the timepoint at which tumor accumulation was assessed following administration of the kynureninase to BALB/c mice, as described in Example 3. For each timepoint shown in FIG. 2C, four vertical bars are shown, each of which depicts the relative tumor accumulation for a kynureninase formed from a particular input ratio of PEG to kynureninase homodimer. The vertical bars for each timepoint correspond, from left to right, to kynureninase homodimers formed from molar input ratios of 10:1, 20:1, 40:1, and 100:1, respectively.

All molar input ratios shown in FIGS. 2A-2C are input ratios of PEG to kynureninase homodimer.

DETAILED DESCRIPTION

The present disclosure provides kynureninase proteins that are covalently bound to polyethylene glycol (PEG), as well as methods of synthesizing such proteins and methods of using the same for the treatment of patients having cancer, such as those that have tumors. In particular, the disclosure provides PEGylated kynureninase proteins characterized by ratios of PEG to kynureninase that effectuate enhanced pharmacokinetic and/or pharmacodynamic properties, such as improved tumor accumulation, prolonged half-life, and greater enzymatic active as compared to kynureninase proteins that are not covalently bound to PEG. Without being limited by mechanism, the kynureninase proteins described herein may exhibit increased resistance to deactivation in serum, which allows for the kynureninase to maintain activity for kynurenine degradation for an increased number of hours. Thus, PEGylated kynureninase enzymes characterized by the PEG:kynureninase ratios described herein may exhibit substantially improved therapeutic properties that make them ideal for therapeutic disease intervention, such as the treatment of cancer. In some embodiments, the kynureninase proteins of the disclosure are used to treat cancer patients, such as those with tumors that express indolamine 2,3 dioxygenase (IDO) or tryptophan 2,3 dioxygenase (TDO).

The sections that follow describe the ratios of PEG: kynureninase polypeptide that result in the advantageous therapeutic properties described above, as well as processes that can be used to produce such proteins and to use the same for treating patients.

Kynureninase Proteins

Some embodiments of the PEGylated kynureninase enzymes concern modified proteins and polypeptides. Particular embodiments concern a modified protein or polypeptide that exhibits at least one functional activity that is comparable to the unmodified version, preferably, the kynurenine degrading activity. In further embodiments, the protein or polypeptide may be further modified to increase serum stability.

Determination of activity may be achieved using assays familiar to those of skill in the art, particularly with respect to the protein's activity and may include for comparison purposes, the use of native and/or recombinant versions of either the modified or unmodified protein or polypeptide.

In some embodiments, a modified polypeptide, such as a modified kynureninase, may be identified based on its increase in kynurenine. For example, substrate recognition sites of the unmodified polypeptide may be identified. This identification may be based on structural analysis or homology analysis. A population of mutants involving modifications of such substrate recognition sites may be generated. In a further embodiment, mutants with increased kynurenine degrading activity may be selected from the mutant population. Selection of desired mutants may include methods, such as detection of byproducts or products from kynurenine degradation.

Modified proteins may possess deletions and/or substitutions of amino acids; thus, a protein with a deletion, a protein with a substitution, and a protein with a deletion and a substitution are modified proteins. In some embodiments, these modified proteins may further include insertions or added amino acids, such as with fusion proteins or proteins with linkers. A modified deleted protein lacks one or more residues of the native protein, but may possess the specificity and/or activity of the native protein. A modified deleted protein may also have reduced immunogenicity or antigenicity. An example of a modified deleted protein is one that has an amino acid residue deleted from at least one antigenic region that is, a region of the protein determined to be antigenic in a particular organism, such as the type of organism that may be administered the modified protein.

Substitution or replacement variants typically contain the exchange of one amino acid for another at one or more sites within the protein and may be designed to modulate one or more properties of the polypeptide, particularly its effector functions and/or bioavailability. Substitutions may or may not be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine, or methionine; serine to threonine; threonine to serine; tryptophan to tyrosine; tyrosine to tryptophan or phenylalanine; and valine to isoleucine or leucine.

In addition to a deletion or substitution, a modified protein may possess an insertion of residues, which typically involves the addition of at least one residue in the polypeptide. This may include the insertion of a targeting peptide or polypeptide or simply a single residue. Terminal additions, called fusion proteins, are discussed below.

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

In some embodiments, a kynureninase according to the embodiments comprises and amino acid sequence at least about 80%, 85%, 86%, 87%, 88%, 89%, 90%, 91%, 92%, 93%, 94%, 95%, 96%, 97%, 98% or 99% identical to the kynureninase of SEQ ID NOs: 1, 2 or 3. In still further embodiments, a kynureninase is at least about 80%, 85%, 86%, 87%, 88%, 89%, 90%, 91%, 92%, 93%, 94%, 95%, 96%, 97%, 98% or 99% identical to the kynureninase of SEQ ID NOs: 1, 2 or 3 and comprises 1, 2, 3, 4, 5, 6, 7, 8, 9, 10, 11, 12, 13, 14, 15, 16, 17, 18, 19, 20, 21, 22, 23, 24 or 25 of the amino acid substitutions selected from the group consisting of L8P, K38E, Y47L, I48F, K50Q, I51M, S60N, K64N, D65G, E66K, N67D, N67P, D67S, A68F, A68T, A68V, F71L, F71M, L72N, K84E, E88N, E89K, E89S, E90Q, D92E, K93N, K93T, A95H, A95Q, K96N, I97H, I97L, I97V, A98G, A99G, A99I, A99R, A99S, A99T, A99V, Y100N, Y100S, Y100T, G101A, H102W, E103F, E103H, E103N, E103Q, E103R, E103V, E103W, V104D, V104E, V104F, V104H, V104K, V104L, V104R, G105A, G105H, G105S, G105T, E106D, K106D, K106E, K106H, K106N, R107P, R107S, P108R, I110A, I110F, I110L, I110M, I110T, T111D, T111H, T111N, T111R, G112A, G112C, G112D, G112K, G112L, G112M, G112Q, G112R, G112S, G112T, G112Y, N127K, I131V, A132V, L133V, A136T, L137T, T138S, N140D, H142Q, Q14R, Y156H, K163T, D168E, H169R, Q175L, I183F, I183L, I183P, I183S, E184A, E184D, E184R, E184T, E184V, E185T, M187L, M189I, K191A, K191G, K191H, K191M, K191N, K191R, K191S, K191T, K191W, E197A, E197D, E197F, E197K, E197M, E197Q, E197S, E197T, E197V, I201C, I201E, I201F, I201H, I201L, I201S, I201T, I201V, H203K, L219M, L219W, F220L, V223I, F225Y, H230F, H230L, H230Y, N232S, Y246F, F249W, D250E, S274A, S274C, S274G, S274N, S274T, L278M, A280G, A280S, A280T, G281S, A282M, A282P, G284N, I285L, V303L, V303S, F306W, F306Y, S311N, K315E, D317E, D317K, I331C, I331L, I331N, I331S, I331T, I331V, N333T, P334N, P335T, L337T, L338A, L338Q, S341I, K373E, K373N, N375A, N375H, Y376C, Y376F, Y376L, K378G, K378P, K378Q, K378R, K380G, K380S, A382G, A382R, A382T, T383S, K384G, K384N, P386K, P386S, V387L, N389E, I405L, F407Y, S408D, S408N, N411R, D413S, D413V, Q416T, E419A, E419L, K420E, R421N, V424I, K427M, N429E, G432A and A436T. In some embodiments, a kynureninase is at least about 80%, 85%, 86%, 87%, 88%, 89%, 90%, 91%, 92%, 93%, 94%, 95%, 96%, 97%, 98% or 99% identical to one of the kynureninases provided in Table 2. In some embodiments, the kynureninase is selected from one of those provided in Table 2.

Table 2, below, sets forth various kynureninase enzymes that may be used in conjunction with the compositions and methods of the present disclosure. Although not listed explicitly in Table 2, Protein (1) herein refers to wild-type human kynureninase, the amino acid sequence of which is set forth in SEQ ID NO: 1.

```
Wild-type human kynureninase:
                                              SEQ ID NO: 1
MEPSSLELPADTVQRIAAELKCHPTDERVALHLDEEDKLRHFRECFYIPK

IQDLPPVDLSLVNKDENAIYFLGNSLGLQPKMVKTYLEEELDKWAKIAAY

GHEVGKRPWITGDESIVGLMKDIVGANEKEIALMNALTVNLHLLMLSFFK

PTPKRYKILLEAKAFPSDHYAIESQLQLHGLNIEESMRMIKPREGEETLR

IEDILEVIEKEGDSIAVILFSGVHFYTGQHFNIPAITKAGQAKGCYVGFD

LAHAVGNVELYLHDWGVDFACWCSYKYLNAGAGGIAGAFIHEKHAHTIKP

ALVGWFGHELSTRFKMDNKLQLIPGVCGFRISNPPILLVCSLHASLEIFK

QATMKALRKKSVLLTGYLEYLIKHNYGKDKAATKKPVVNIITPSHVEERG

CQLTITFSVPNKDVFQELEKRGVVCDKRNPNGIRVAPVPLYNSFHDVYKF

TNLLTSILDSAETKN
```

TABLE 2

| Exemplary kynureninase enzymes of the disclosure | |
|---|---|
| Protein | List of Mutations |
| 2 | N67D/L72N/E103Q/M189I/F225Y/S274G/I331V/I405L/S408N |
| 3 | A99I/G112A/F306Y/I331N/I405L/S408N/A436T |
| 4 | Q14R/A99I/G112A/M189I/H230Y/F306Y/I331N/I405L/S408N/A436T |
| 5 | N67D/L72N/E103Q/A99I/G112A/M189I/F225Y/S274G/I331V/F306Y/K380S/A382R/K384N/P386K/I405L/S408N/A436T |
| 6 | N67D/L72N/A99I/H102W/E103F/V104E/K106E/R107S/I110M/A136T/M189I/F225Y/S274G/I331C/N333T/S341I/I405L/S408N |
| 7 | N67D/L72N/A99I/H102W/E103F/V104E/K106E/R107S/I110M/I131V/L133V/A136T/T138S/M189I/F225Y/G274T/L278M/**G281S**/**A282P**/F306W/K315E/D317E/I331C/N333T/S341I/I405L/S408N |
| 8 | N67D/L72N/A99I/H102W/E103F/V104E/E106D/R107S/M110I/T111H/G112Y/A132V/A136T/M189I/V223I/F225Y/S274G/A280S/G281S/A282P/I331C/N333T/S341I/I405L/S408N |
| 9 | A99I/G112A/G284N/I285L/F306Y/I331N/I405L/S408N/A436T |
| 10 | A99I/G112A/K191N/F306Y/I331N/I405L/S408N/A436T |

TABLE 2-continued

| Exemplary kynureninase enzymes of the disclosure | |
|---|---|
| Protein | List of Mutations |
| 11 | L8P/A99I/G112A/Q175L/F306Y/I331N/K373E/K378R/I405L/S408N/A436T |
| 12 | A99I/G112A/F306Y/I331N/K380S/A382R/K384N/P386K/I405L/S408N/A436T |
| 13 | A99I/G112A/F306Y/I331N/N375H/Y376L/K378P/I405L/S408N/A436T |
| 14 | N67D/A68T/L72N/A99I/H102W/E103F/V104E/E106D/R107S/M110L/T111H/G112Y/A136T/M189I/F225Y/S274G/F306W/I331C/N333T/S341I/I405L/S408N |
| 15 | N67D/L72N/A99I/H102W/E103F/V104E/K106E/R107S/I110M/A132V/A136T/M189I/F225Y/G274S/A280S/G281S/A282P/F306W/I331C/N333T/S341I/I405L/S408N |
| 16 | N67D/F71L/L72N/A99I/H102W/E103FN104E/E106D/R107S/M110I/G112Y/A136T/M189I/F225Y/S274G/A280S/G281S/A282P/I331C/N333T/S341I/I405L/S408N |
| 17 | D67N/A68V/L72N/A99I/H102W/E103F/V104E/K106E/R107S/M110I/T111H/G112Y/A136T/M189I/F225Y/G274T/A280S/G281S/A282P/F306W/K315E/I331C/N333T/S341I/I405L/S408N |
| 18 | D67N/L72N/A99I/H102W/E103F/V104E/K106E/R107S/I110M/T111H/G112Y/A136T/M189I/F225Y/G274S/A280S/G281S/A282P/F306W/K315E/I331C/N333T/S341I/I405L/S408N |
| 19 | N67D/L72N/A99I/H102W/E103F/V104E/E106D/R107S/M110I/T111H/G112Y/A132V/A136T/M189I/V223I/F225Y/S274G/A280S/G281S/A282P/V303L/F306W/S311N/K315E/I331C/N333T/S341I/I405L/S408N |
| 20 | D67S/L72N/A99I/H102W/E103F/V104E/K106E/R107S/I110M/A132V/L133V/A136T/M189I/F225Y/G274A/A280S/A282P/F306W/I331C/N333T/S341I/I405L/S408N |
| 21 | D67N/L72N/A99I/H102W/E103F/V104E/K106E/R107S/I110M/T111H/G112Y/A136T/M189I/F225Y/G274N/L278M/A282P/F306W/K315E/I331C/N333T/S341I/I405L/S408N |
| 22 | D67N/A68V/L72N/A99I/H102W/E103F/V104E/K106E/R107S/M110I/A136T/M189I/F225Y/G274T/G281S/A282P/F306W/I331C/N333T/S341I/I405L/S408N |
| 23 | N67D/F71L/L72N/A99I/H102W/E103F/V104E/E106D/R107S/M110I/T111H/G112Y/A136T/M189I/V223I/F225Y/G274S/A280S/G281S/A282P/F306W/K315E/I331C/N333T/S341I/I405L/S408N |
| 24 | D67N/L72N/A99I/H102W/E103F/V104E/K106E/R107S/I110M/T111H/G112Y/A136T/M189I/F225Y/G274S/A280S/G281S/A282P/F306W/D317E/I331C/N333T/S341I/I405L/S408N |
| 25 | N67D/L72N/A99I/H102W/E103F/V104E/E106D/R107S/M110I/T111H/G112Y/A132V/A136T/V223I/M189I/F225Y/S274G/A280S/G281S/A282P/V303S/F306W/K315E/D317K/I331C/N333T/S341I/I405L/S408N |
| 26 | N67D/A68T/L72N/A99I/H102W/E103F/V104E/E106D/R107S/M110I/T111H/G112Y/A136T/M189I/F225Y/G274N/A280S/A282P/F306W/I331C/N333T/S341I/I405L/S408N |
| 27 | L72N/A99V/Y100N/H102W/E103F/V104E/K106D/R107S/T111H/G112Y/L133V/A136T/F225Y/S274N/A280S/G281S/A282P/F306W/I331C/N333T |
| 28 | L72N/A99V/Y100N/H102W/E103F/V104E/K106D/R107S/T111N/G112Y/I131V/L133V/A136T/F225Y/S274T/A280S/G281S/A282P/F306W/I331C/N333T |
| 29 | L72N/A99V/Y100N/H102W/E103F/V104E/K106D/R107S/I110M/T111N/G112Y/I131V/L133V/A136T/F225Y/S274N/A280S/G281S/A282P/F306W/I331C/N333T |
| 30 | N67D/F71L/L72N/A99V/Y100N/H102W/E103F/V104E/K106D/R107S/I110M/T111H/G112Y/A136T/F225Y/S274G/A280S/G281S/A282P/F306W/I331C/N333T |
| 31 | L72N/E90Q/A99V/Y100N/H102W/E103F/V104E/K106D/R107S/I110M/T111D/G112Y/A136T/F225Y/S274N/A280S/G281S/A282M/F306W/I331C/N333T |
| 32 | Y100T/H102W/E103F/V104E/K106D/R107S/T111H/G112Y/A136T/M189I/F225Y/A280G/A282P/F306W/I331C/N333T |
| 33 | A99S/Y100S/G101A/H102W/E103F/V104E/K106D/R107S/I110M/T111H/G112Y/A136T/F225Y/A280T/A282P/F306W/I331C/N333T/K373N |
| 34 | K191S-E197T-I201H |
| 35 | K191R-E197S-I201T |

TABLE 2-continued

| Exemplary kynureninase enzymes of the disclosure | |
|---|---|
| Protein | List of Mutations |
| 36 | K191S-E197T-I201T |
| 37 | I183P-E184A |
| 38 | K191R-E197F-I201T |
| 39 | K191R-I201E |
| 40 | K191W-E197V-I201E |
| 41 | K191H-E197V-I201E |
| 42 | E197M-I201L |
| 43 | K191G-E197V-I201H |
| 44 | K191T-E1970-I201E |
| 45 | K191H-E197V-I201E |
| 46 | N67D/A68T/L72N/A99I/H102W/E103F/V104E/E106D/R107S/M110I/T111H/G112Y/A136T/M189I/F225Y/G274N/A280S/A282P/F306W/I331C/N333T/S341I/K373N/I405L/S408N |
| 47 | L72N/E90Q/A99V/Y100N/H102W/E103F/V104E/K106D/R107S/I110M/T111D/G112Y/A136T/F225Y/S274N/A280S/G281S/A282M/F306W/I331C/N333T/K373N |
| 48 | N67D/A68T/L72N/E88N/E89K/D92E/K93T/A95Q/K96N/I97H/A98G/A99I/H102W/E103F/V104E/E106D/R107S/M110L/T111H/G112Y/A136T/M189I/F225Y/A280S/A282P/F306W/I331L/N333T/P335T/L338A/S341I/I405L/S408N/E419A/K420E/R421N/V424I |
| 49 | Y47L/I48F/K50Q/del51-62/K64N/D65G/E66K/N67P/A68F/L72N/E88N/E89S/E90Q/K93N/K96N/I97L/A99I/H102W/E103F/V104E/E106D/R107S/M110L/T111H/G112Y/A136T/M189I/F225Y/A280G/A282P/F306W/I331C/N333T/S341I/I405L/S408N |
| 50 | Q14R/K38E/I51M/N67D/A68T/L72N/A99I/H102W/E103F/V104E/E106D/R107S/M110L/T111H/G112Y/N127K/A136T/M189I/K191N/E197T/F225Y/H230F/S274G/F306W/I331C/N333T/S341I/I405L/S408N |
| 51 | S60N/N67D/L72N/K84E/A99I/H102W/E103F/V104E/E106D/R107S/M110I/T111H/G112Y/A132V/A136T/Y156H/K163T/M1891/V223I/F225Y/S274G/A280S/G281S/A282P/I331C/N333T/S341I/I405L/S408N |
| 52 | N67D/L72N/A99I/H102W/E103F/V104E/E106D/R107S/M110I/T111H/G112Y/A132V/A136T/M189I/V223I/F225Y/S274G/A280S/G281S/A282P/I331C/N333T/L338Q/S341I/I405L/S408N |
| 53 | N67D/L72N/A99I/Y100N/H102W/E103F/V104E/E106D/R107S/M110I/T111H/G112Y/A132V/A136T/M189I/V223I/F225Y/S274G/A280S/G281S/A282P/I331C/N333T/S341I/I405L/S408N |
| 54 | N67D/L72N/I97V/A99I/H102W/E103F/V104E/E106D/R107S/M110I/T111H/G112Y/A132V/A136T/N140D/M189I/V223I/F225Y/S274G/A280S/G281S/A282P/I331C/N333T/S341I/I405L/S408N |
| 55 | N67D/A68T/L72N/E90Q/K93N/A95H/K96N/I97L/A99I/H102W/E103F/V104E/E106D/R107S/M110L/T111H/G112Y/A136T/M189I/F225Y/A280S/A282P/F306W/I331C/N333T/S341I/I405L/S408N |
| 56 | N67D/L72N/A99I/H102W/E103F/V104E/E106D/R107S/M110I/T111H/G112Y/A132V/A136T/M189I/V223I/F225Y/S274G/A280S/G281S/A282P/I331C/N333T/S341I/I405L/S408N |
| 57 | N67D/L72N/A99I/H102W/E103F/V104E/E106D/R107S/M110I/T111H/G112Y/A132V/A136T/D168E/M189I/V223I/F225Y/S274G/A280S/G281S/A282P/I331C/N333T/S341I/I405L/S408N |
| 58 | N67D/L72N/A99I/H102W/E103F/V104E/E106D/R107S/M110I/T111H/G112Y/A132V/A136T/M189I/V223I/F225Y/D250E/S274G/A280S/G281S/A282P/I331C/N333T/S341I/I405L/S408N |
| 59 | N67D/A68T/L72N/A99I/H102W/E103F/V104E/E106D/R107S/M110I/T111H/G112Y/A136T/D168E/M189I/F225Y/G274N/A280S/A282P/F306W/I331C/N333T/S341I/I405L/S408N |

TABLE 2-continued

| Exemplary kynureninase enzymes of the disclosure | |
|---|---|
| Protein | List of Mutations |
| 60 | N67D/A68T/L72N/A99I/H102W/E103F/V104E/E106D/R107S/M110I/T111H/G112Y/A136T/M189I/F225Y/D250E/G274N/A280S/A282P/F306W/I331C/N333T/S341I/I405L/S408N |
| 61 | L72N/A99I/H102W/G112Y/A282P/F306W/I331S/N333T |
| 62 | L72N/A99I/H102W/G112Y/A282P/F306W/I331S/N333T/P334N |
| 63 | L72N/A99I/H102W/E103F/E106D/M110I/T111H/G112Y/A132V/A136T/M189I/A282P/I331C/N333T/S341I/S408N |
| 64 | N67D/L72N/A99I/H102W/E103F/V104E/E106D/R107S/T111H/G112Y/A136T/M189I/A280S/A282P/F306W/I331C/N333T/I405L/S408N |
| 65 | N67D/L72N/A99I/H102W/E103F/V104E/E106D/R107S/M110I/T111H/G112Y/A132V/A136T/M189I/**K191S**/**E197T**/**I201H**/V223I/F225Y/S274G/A280S/G281S/A282P/I331C/N333T/S341I/I405L/S408N |
| 66 | N67D/L72N/A99I/H102W/E103F/V104E/E106D/R107S/M110I/T111H/G112Y/A132V/A136T/M189I/**K191R**/**E197F**/**I201T**/V223I/F225Y/S274G/A280S/G281S/A282P/I331C/N333T/S341I/I405L/S408N |
| 67 | N67D/L72N/A99I/H102W/E103F/V104E/E106D/R107S/M110I/T111H/G112Y/A132V/A136T/M189I/**K191SW**/**E197V**/**I201E**/V223I/F225Y/S274G/A280S/G281S/A282P/I331C/N333T/S341I/I405L/S408N |
| 68 | N67D/L72N/A99I/H102W/E103F/V104E/E106D/R107S/M110I/T111H/G112Y/A132V/A136T/M189I/**E197M**/**I201L**/V223I/F225Y/S274G/A280S/G281S/A282P/I331C/N333T/S341I/I405L/S408N |
| 69 | N67D/L72N/A99I/H102W/E103F/V104E/E106D/R107S/M110I/T111H/G112Y/A132V/A136T/M189I/**K191H**/E197V/**I201E**/V223I/F225Y/S274G/A280S/G281S/A282P/I331C/N333T/S341I/I405L/S408N |
| 70 | N67D/L72N/A99I/H102W/E103F/V104E/E106D/R107S/M110I/T111H/G112Y/A132V/A136T/M189I/**K191R**/**E197S**/**I201T**/V223I/F225Y/S274G/A280S/G281S/A282P/I331C/N333T/S341I/I405L/S408N |
| 71 | N67D/L72N/A99I/H102W/E103F/V104E/E106D/R107S/M110I/T111H/G112Y/A132V/A136T/M189I/**K191G**/**E197V**/**I201H**/V223I/F225Y/S274G/A280S/G281S/A282P/I331C/N333T/S341I/I405L/S408N |
| 72 | N67D/L72N/A99I/H102W/E103F/V104E/E106D/R107S/M110I/T111H/G112Y/A132V/A136T/M189I/**K191S**/**E197T**/**I201T**/V223I/F225Y/S274G/A280S/G281S/A282P/I331C/N333T/S341I/I405L/S408N |
| 73 | N67D/L72N/A99I/H102W/E103F/V104E/E106D/R107S/M110I/T111H/G112Y/A132V/A136T/M189I/**K191G**/**E197A**/**I201E**/V223I/F225Y/S274G/A280S/G281S/A282P/I331C/N333T/S341I/I405L/S408N |
| 74 | L72N/A99S/H102W/E103F/V104K/K106H/R107S/G112Y/A282P/F306W/I331C/N333T |
| 75 | N67D/L72N/A99I/H102W/K106D/S274G/A280S/G281S/A282P/F306W/I331S/N333T |
| 76 | N67D/A68T/L72N/A99I/H102W/E103F/V104E/K106D/R107S/I110L/T111H/G112Y/A136T/M189I/F225Y/S274N/A280S/A282P/F306W/I331C/N333T/S341I/I405L/S408N |
| 77 | L72N/A99I/H102W/E103V/V104E/K106D/R107S/T111H/G112Y/A282P/F306W/I331S/N333T |
| 78 | L72N/A99V/H102W/E103F/V104E/K106N/T111N/A280S/A282P/F306W/I331S/N333T |
| 79 | L72N/A99I/H102W/G112Y/A282P/F306W/I331S/N333T/T383S/D413V |
| 80 | L72N/A99I/Y100N/H102W/G112Y/H169R/M187L/Y246F/A282P/F306W/I331S/N333T/A382T |
| 81 | L72N/A99I/H102W/V104R/G105H/R107P/G112Y/A282P/F306W/I331S/N333T |
| 82 | L72N/H102W/E103N/K106D/R107P/T111R/G112Y/A282P/F306W/I331T/N333T |
| 83 | L72N/A99I/H102W/G112Y/A282P/F306W/I331S/N333T/Y376F/K3780 |
| 84 | L72N/A99I/H102W/G112Y/K191S/E197D/I201E/A282P/F306W/I331S/N333T |
| 85 | L72N/A99I/H102W/G112Y/K191A/I201V/A282P/F306W/I331S/N333T |

TABLE 2-continued

| Exemplary kynureninase enzymes of the disclosure | |
|---|---|
| Protein | List of Mutations |
| 86 | L72N/A99I/H102W/G112Y/I183P/E184A/M187L/M189I/K191N/E197T/I201T/A282P/F306W/I331S/N333T |
| 87 | F71M/L72N/E103F/V104H/G105T/I183P/E184A/M187L/M189I/K191N/E197T/I201T/A2805/A282P/F306Y |
| 88 | L72N/H102W/G112Y/A282P/F306W/I331S/N333T |
| 89 | L72N/G101A/H102W/G112Y/E184A/A282P/F306W/I331S/N333T |
| 90 | L72N/A99I/H102W/G112Y/I183P/E184A/A282P/F306W/I331S/N333T |
| 91 | L72N/A99I/H102W/G112Y/I183L/M189I/K191S/I201T/A282P/F306W/I331S/N333T |
| 92 | L72N/A99I/H102W/G112Y/M187L/M189I/K191R/I201T/A282P/F306W/I331S/N333T |
| 93 | L72N/A99V/E103Q/H102W/G112Y/I183P/E184A/E197A/I201T/A282P/F306W/I331S/N333T |
| 94 | L72N/A99I/H102W/E103Q/V104D/G105S/G112Y/I183P/E184A/A282P/F306W/I331S/N333T |
| 95 | L72N/A99I/H102W/G112Y/I183P/A282P/F306W/I331S/N333T |
| 96 | L72N/A99V/H102W/E103Q/V104H/G112Y/I183P/M189I/K191S/A282P/F306W/I331S/N333T |
| 97 | L72N/H102W/R107P/G112Y/I183P/E184A/E197A/A282P/F306W/I331S/N333T |
| 98 | L72N/A99T/H102W/G112Y/I183P/E184A/I201T/A282P/F306W/I331S/N333T |
| 99 | L72N/A99I/H102W/G112Y/A136T/L137T/F225Y/A282P/F306W/I331S/N333T/F407Y |
| 100 | L72N/A99I/H102W/G112Y/A282P/F306W/I331S/N333T/I405L/S408D/A436T |
| 101 | L72N/A99I/H102W/G112Y/I183P/E184A/M187L/M189I/K191N/A282P/F306W/I331S/N333T |
| 102 | L72N/A99V/H102W/E103Q/G112Y/I183P/E184A/E197A/I201T/A282P/F306W/I331S/N333T |
| 103 | L72N/A99V/H102W/E103Q/V104H/G105A/R107P/G112Y/M187L/K191S/I201T/A282P/F306W/I331S/N333T |
| 104 | L72N/H102W/V104D/G105A/G112Y/I183F/E184T/M189I/K191S/I201T/A282P/F306W/I331S/N333T |
| 105 | L72N/A99V/H102W/V104H/G105A/G112Y/M187L/M189I/K191S/I201T/A282P/F306W/I331S/N333T |
| 106 | L72N/A99I/H102W/V104D/G105S/G112Y/I183P/M187L/M189I/I201T/A282P/F306W/I331S/N333T |
| 107 | L72N/A99V/H102W/E103Q/V104D/G112Y/I183P/E184A/M189I/K191R/I201T/A280S/A282P/F306W/I331S/N333T |
| 108 | L72N/A99I/H102W/E103Q/V104H/G112Y/I183L/M189I/A282P/F306W/I331S/N333T |
| 109 | L72N/A99I/H102W/G112Y/I183S/E183A/M189I/K191N/I201T/A282P/F306W/I331S/N333T |
| 110 | L72N/A99I/H102W/G112Y/A136T/L137T/A282P/F306W/I331S/N333T |
| 111 | L72N/A99I/H102W/G112Y/A136T/L137T/F220L/F225Y/H230L/A282P/F306W/I331S/N333T |
| 112 | L72N/A99I/H102W/G112Y/L137T/F220L/H203K/A282P/F306W/I331S/N333T |
| 113 | L72N/A99I/H102W/G112Y/A136T/L137T/F225Y/A282P/F306W/I331S/N333T/F407Y |
| 114 | L72N/A99I/H102W/R107P/G112Y/I183L/E184A/A282P/F306W/I331S/N333T |
| 115 | L72N/A99V/H102W/E103Q/V104H/G105S/R107P/G112Y/M187L/K191R/I201T/A282P/F306W/I331S/N333T |

TABLE 2-continued

| Exemplary kynureninase enzymes of the disclosure | |
|---|---|
| Protein | List of Mutations |
| 116 | L72N/A99I/H102W/G112Y/I183L/E184R/M187L/M189I/K191N/E197K/I201T/A282P/F306W/I331S/N333T |
| 117 | L72N/A99I/H102W/G112Y/E184D/M187L/M189I/K191R/E197A/I201T/A282P/F306W/I331S/N333T |
| 118 | L72N/A99I/H102W/G112Y/I183S/E184V/M187L/M189I/K191R/A282P/F306W/I331S/N333T |
| 119 | L72N/A99V/H102W/V104D/G112Y/E184A/M187L/M189I/K191R/E197A/A282P/F306W/I331S/N333T |
| 120 | L72N/A99V/H102W/V104H/G105A/G112Y/M189I/K191S/I201T/A282P/F306W/I331S/N333T |
| 121 | L72N/A99I/H102W/E103Q/V104D/G105S/G112Y/I183P/M189I/K191S/I201T/A280S/A282P/F306W/I331S/N333T |
| 122 | L72N/A99V/H102W/E103Q/R107P/G112Y/I183P/E184A/I201T/A282P/F306W/I331S/N333T |
| 123 | L72N/A99T/H102W/E103F/R107P/G112Y/I183P/E184N1201T/A282P/S724Q/F306W/I331S/N333T |
| 124 | L72N/A99V/H102W/R107P/G112Y/A282P/F306W/I331S/N333T |
| 125 | L72N/A99V/H102W/E103Q/V104H/G105A/R107P/G112Y/M187L/K191S/I201T/A282P/F306W/I331S/N333T/**I405L/S408D** |
| 126 | L72N/A99V/H102W/E103Q/V104D/G112Q/I183P/E184A/M189I/K191R/I201T/A280S/A282P/F306W/I331S/N333T |
| 127 | L72N/A99V/H102W/E103Q/V104H/R107P/G112Y/I183P/A282P/F306W/I331S/N333T/S408N/A436T |
| 128 | L72N/A99V/H102W/E103Q/V104H/G105A/R107P/G112L/M187L/K191S/I201T/F220L/F225Y/A282P/F306W/I331S/N333T |
| 129 | L72N/A99V/H102W/E103Q/V104H/G105A/R107P/G112L/A136T/M187L/K191S/I201T/H230L/A282P/F306W/I331S/N333T |
| 130 | L72N/A99V/H102W/E103Q/V104H/G105A/R107P/G112Q/M187L/K191S/I201T/F220L/F225Y/A282P/F306W/I331S/N333T |
| 131 | L72N/A99V/H102W/E103Q/V104D/G112R/I183P/E184A/M189I/K191R/I201T/A280S/A282P/F306W/I331S/N333T |
| 132 | L72N/A99V/H102W/V104H/G105A/M189I/K191S/I201T/A282P/F306W/I331S/N333T |
| 133 | L72N/A99V/H102W/E103Q/V104D/R107P/G112Q/I201E/A282P/F306W/I331S/N333T |
| 134 | L72N/A99V/H102W/E103Q/V104D/G112L/M187L/I201T/A282P/F306W/I331S/N333T |
| 135 | L72N/A99V/H102W/E103Q/V104L/G112D/K191S/A282P/F306W/I331S/N333T/S408N |
| 136 | L72N/A99I/H102W/E103Q/V104L/G112Y/A136T/K191S/A282P/F306W/I331S/N333T/S408N/A436T |
| 137 | L72N/A99V/H102W/E103Q/V104L/R107P/G112Y/A136T/I183P/K191S/I201T/A282P/F306W/I331S/N333T |
| 138 | L72N/A99V/H102W/E103Q/V104H/R107P/G112Y/H142Q/K191S/I201T/A282P/F306W/I331S/N333T |
| 139 | L72N/A99I/H102W/E103Q/V104H/G112D/K191S/I201T/F225Y/A282P/F306W/I331S/N333T/S408N |
| 140 | L72N/A99V/H102W/E103Q/V104H/G105A/R107P/G112Y/M187L/K191S/I201T/A282P/F306W/I331S/N333T/S408D |
| 141 | L72N/A99G/H102W/E103H/V104H/R107P/G112Y/I183P/A282P/F306W/I331S/N333T/S408N/A436T |
| 142 (SEQ ID NO: 3) | L72N/A99R/H102W/E103R/V104H/R107P/G112Y/I183P/A282P/F306W/I331S/N333T/S408N/A436T |

TABLE 2-continued

Exemplary kynureninase enzymes of the disclosure

| Protein | List of Mutations |
|---|---|
| 143 | L72N/A99G/H102W/E103W/V04H/R107P/G112Y/I183P/A282P/F306W/I331S/N333T/5408N/A436T |
| 144 | L72N/A99V/H102W/E103Q/V104H/R107P/I183P/A282P/F306W/I331S/N333T/S408N/A436T |
| 145 | L72N/A99V/H102W/E103Q/V104H/R107P/G112Y/N140D/I183P/A282P/F306W/I331S/N333T/S408N/A436T |
| 146 | L72N/A99V/H102W/E103Q/V104H/R107P/I110F/G112Y/I183P/A282P/F306W/I331S/N333T/S408N/A436T |
| 147 | L72N/A99V/H102W/E103Q/V104H/R107P/G112L/I183P/A282P/F306W/I331S/N333T/S408N/A436T |
| 148 | L72N/A99V/H102W/E103Q/V104H/R107P/G112K/I183P/A282P/F306W/I331S/N333T/S408N/A436T |
| 149 | L72N/A99V/H102W/E103Q/V104H/R107P/T111R/G112R/I183P/A282P/F306W/I331S/N333T/S408N/A436T |
| 150 | L72N/A99V/H102W/E103Q/V104H/R107P/G112Y/I183P/L219M/A282P/F306W/I331S/N333T/S408N/A436T |
| 151 | L72N/A99V/H102W/E103Q/V104H/G105A/R107P/T111N/Y112A/I183P/A282P/F306W/I331S/N333T/S408N/A436T |
| 152 | L72N/A99V/H102W/E103Q/V104H/R107P/G112Y/I183P/E184A/M189I/K191R/I201T/L219W/A282P/F306W/I331S/N333T/S408N/A436T |
| 153 | L72N/A99V/H102W/E103Q/V104H/R107P/G112Y/D168E/I183P/A282P/F306W/I331S/N333T/S408N/A436T |
| 154 | L72N/A99V/H102W/E103Q/V104H/R107P/G112Y/I183P/E184A/M189I/K191R/I201T/F249W/A282P/F306W/I331S/N333T/S408N/A436T |
| 155 | L72N/A99V/H102W/E103Q/V104H/R107P/G112Y/I183P/F249W/A282P/F306W/I331S/N333T/S408N/A436T |
| 156 | Identical AA sequence to (126) |
| 157 (SEQ ID NO: 2) | L72N/A99R/H102W/E103R/V104H/R107P/G112Y/I183P/F249W/A282P/F306W/I331S/N333T/5408N/A436T |
| 158 | L72N/A99G/H102W/E103/VN104H/R107P/G112Y/I183P/F249W/A282P/F306W/I331S/N333T/S408N/A436T |
| 159 | L72N/A99G/H102W/E103W/V104H/R107P/Y112K/I183P/F249W/A282P/F306W/I331S/N333T/S408N/A436T |
| 160 | L72N/A99G/H102W/E103W/V104F/R107P/G112Y/I183P/A282P/F306W/I331S/N333T/S408N/A436T |
| 161 | L72N/A99G/H102W/E103/V104H/R107P/G112Y/I183P/A282P/F306W/I331S/N333T/S408N/A436T AND Arginine Insertion between P107 and P108 |
| 162 | L72N/A99G/H102W/E103W/V104H/R107P/P108R/G112Y/I183P/A282P/F306W/I331S/N333T/S408N/A436T-AND Leucine insertion between P107 and R108 |
| 163 | L72N/A99G/H102W/E103W/V104H/R107P/Y112K/I183P/A282P/F306W/I331S/N333T/S408N/A436T |
| 164 | L72N/A99G/H102W/E103W/V104H/R107P/G112Y/I183P/K191M/A282P/F306W/I331S/N333T/S408N/A436T |
| 165 | L72N/A99G/H102W/E103W/V104H/R107P/G112Y/I183P/M189I/I201S/N232S/A282P/F306W/I331S/N333T/S408N/A436T |
| 166 | L72N/A99G/H102W/E103W/V104H/R107P/G112Y/I183P/E184A/M189I/K191R/I201F/A282P/F306W/I331S/N333T/S408N/A436T |
| 167 | F71M/L72N/E103F/V104H/G105T/I110T/G112T/I183P/E184A/M187L/M189I/K191N/E197T/I201T/A280S/A282P/F306Y |
| 168 | I183P/E184A/M187L/M189I/K191S/E197T/I201T/N375A/Y376Q/K378G/K380G/A382G/K384G/P3865/N411R/D413S/Q416T/E419L/K427M/N429E/G432A/A436T |

TABLE 2-continued

Exemplary kynureninase enzymes of the disclosure

| Protein | List of Mutations |
|---|---|
| 169 | A99I/G1125/F306Y/I405L/5408N/A436T/I183P/E185T/M189I/K191N/N375H/Y376L/K378P/K3805/A382R/K384N/P386KN387L/N389E |
| 170 | L72N/A99R/H102W/E103R/V104D/G112M/I183P/A282P/F306W/I331S/N333T/5408N/A436T |
| 171 | L72N/A99G/H102W/E103W/V104H/R107P/G112M/I183P/I201F/F249W/A282P/F306W/I331S/N333T/5408N/A436T |
| 172 | L72N/A99G/H102W/E103W/V104H/R107P/G112Y/I183P/M189I/I201C/F249W/A282P/F306W/I331S/N333T/S408N/A436T |
| 173 | L72N/A99R/H102W/E103R/V104H/R107P/G112Y/I183P/A282P/F306W/I331S/N333T/L337T/S408N/A436T |
| 174 | L72N/A99R/H102W/E103R/V104H/R107P/I110A/G112Y/I183P/A280G/A282P/F306W/I331S/N333T/L337T/S408N/A436T |

Conjugates

Compositions and methods of the present disclosure involve modified kynureninases, such as by forming conjugates with heterologous peptide segments or polymers, such as polyethylene glycol (PEG). The kynureninase is linked to PEG to increase the hydrodynamic radius of the enzyme and hence increase the serum persistence. In some embodiments, the disclosed polypeptide may be conjugated to any targeting agent, such as a ligand having the ability to specifically and stably bind to an external receptor or binding site on a tumor cell (U.S. Patent Publ. 2009/0304666).

PEGylation

In some embodiments of the disclosure, methods and compositions related to PEGylation of kynureninase are disclosed. For example, the kynureninase is PEGylated in accordance with the methods disclosed herein.

PEGylation is the process of covalent attachment of poly(ethylene glycol) polymer chains to another molecule, normally a drug or therapeutic protein. PEGylation is routinely achieved by incubation of a reactive derivative of PEG with the target macromolecule. The covalent attachment of PEG to a drug or therapeutic protein can mask the agent from the host's immune system (reduced immunogenicity and antigenicity) or increase the hydrodynamic size (size in solution) of the agent, which prolongs its circulatory time by reducing renal clearance. PEGylation can also provide water solubility to hydrophobic drugs and proteins. The first step of the PEGylation is the suitable functionalization of the PEG polymer at one or both terminals. PEGs that are activated at each terminus with the same reactive moiety are known as "homobifunctional," whereas if the functional groups present are different, then the PEG derivative is referred as "heterobifunctional" or "heterofunctional." The chemically active or activated derivatives of the PEG polymer are prepared to attach the PEG to the desired molecule.

The choice of the suitable functional group for the PEG derivative is based on the type of available reactive group on the molecule that will be coupled to the PEG. For proteins, typical reactive amino acids include lysine, cysteine, histidine, arginine, aspartic acid, glutamic acid, serine, threonine, and tyrosine. The N-terminal amino group and the C-terminal carboxylic acid can also be used. The techniques used to form first generation PEG derivatives are generally reacting the PEG polymer with a group that is reactive with hydroxyl groups, typically anhydrides, acid chlorides, chloroformates, and carbonates. In the second generation PEGylation chemistry more efficient functional groups, such as aldehyde, esters, amides, etc., are made available for conjugation.

As applications of PEGylation have become more and more advanced and sophisticated, there has been an increase in need for heterobifunctional PEGs for conjugation. These heterobifunctional PEGs are very useful in linking two entities, where a hydrophilic, flexible, and biocompatible spacer is needed. Preferred end groups for heterobifunctional PEGs are maleimide, vinyl sulfones, pyridyl disulfide, amine, carboxylic acids, and NHS esters.

The most common modification agents, or linkers, are based on methoxy PEG (mPEG) molecules. Their activity depends on adding a protein-modifying group to the alcohol end. In some instances, polyethylene glycol (PEG diol) is used as the precursor molecule. The diol is subsequently modified at both ends in order to make a hetero- or homo-dimeric PEG-linked molecule.

Proteins are generally PEGylated at nucleophilic sites, such as unprotonated thiols (cysteinyl residues) or amino groups. Examples of cysteinyl-specific (i.e., cystine-reactive) modification reagents include PEG maleimide, PEG iodoacetate, PEG thiols, and PEG vinylsulfone. All four are strongly cysteinyl-specific under mild conditions and neutral to slightly alkaline pH.

Amine-specific (i.e., lysine-reactive) modification agents include PEG NHS ester, PEG tresylate, PEG aldehyde, PEG isothiocyanate, and several others. All react under mild conditions and are very specific for amino groups. The PEG NHS ester is probably one of the more reactive agents; however, its high reactivity can make the PEGylation reaction difficult to control on a large scale. PEG aldehyde forms an imine with the amino group, which is then reduced to a secondary amine with sodium cyanoborohydride. Unlike sodium borohydride, sodium cyanoborohydride will not reduce disulfide bonds. However, this chemical is highly toxic and must be handled cautiously, particularly at lower pH where it becomes volatile.

Due to the multiple lysine residues on most proteins, site-specific PEGylation can be a challenge. Because these reagents react with unprotonated amino groups, it is possible to direct the PEGylation to lower-pK amino groups by performing the reaction at a lower pH. Generally, the pK of the alpha-amino group is 1-2 pH units lower than the epsilon-amino group of lysine residues. By PEGylating the molecule at pH 7 or below, high selectivity for the N-terminus frequently can be attained. However, this is only feasible if the N-terminal portion of the protein is not required for biological activity. Still, the pharmacokinetic benefits from PEGylation frequently outweigh a significant loss of in vitro bioactivity, resulting in a product with much greater in vivo bioactivity regardless of PEGylation chemistry.

There are several parameters to consider when developing a PEGylation procedure. For thiol-specific PEGylation reactions, parameters to consider include: protein concentration, PEG-to-protein ratio (on a molar basis), temperature, pH, reaction time, and in some instances, the exclusion of oxygen. (Oxygen can contribute to intermolecular disulfide formation by the protein, which will reduce the yield of the PEGylated product.) The same factors should be considered (with the exception of oxygen) for amine-specific modification except that pH may be even more critical, particularly when targeting the N-terminal amino group.

For both amine- and thiol-specific modifications, the reaction conditions may affect the stability of the protein. This may limit the temperature, protein concentration, and pH. In addition, the reactivity of the PEG linker should be known before starting the PEGylation reaction. For example, if the PEGylation agent is only 70 percent active, the amount of PEG used should ensure that only active PEG molecules are counted in the protein-to-PEG reaction stoichiometry.

Linkers for Chemical Conjugation

A variety of linkers can be used to covalently couple reactive residues within a kynureninase homodimer and a PEG molecule to one another, for instance, so as to form a conjugate as described herein. Exemplary linkers include those that may be cleaved, for instance, by enzymatic hydrolysis, photolysis, hydrolysis under acidic conditions, hydrolysis under basic conditions, oxidation, disulfide reduction, nucleophilic cleavage, or organometallic cleavage (see, for example, Leriche et al., Bioorg. Med. Chem., 20:571-582, 2012, the disclosure of which is incorporated herein by reference as it pertains to linkers suitable for chemical coupling). Examples of linkers useful for the synthesis of conjugates described herein include those that contain electrophiles, such as Michael acceptors (e.g., maleimides), activated esters, electron-deficient carbonyl compounds, and aldehydes, among others, suitable for reaction with nucleophilic substituents present within antibodies, antigen-binding fragments, proteins, peptides, and small molecules, such as amine and thiol moieties. For instance, linkers suitable for the synthesis of therapeutic conjugates include, without limitation, alkyl, cycloalkyl, and heterocycloalkyl linkers, such as open-chain ethyl, propyl, butyl, hexyl, heptyl, octyl, nonyl, or decyl chains, cyclohexyl groups, cyclopentyl groups, cyclobutyl groups, cyclopropyl groups, piperidinyl groups, morpholino groups, or others containing two reactive moieties (e.g., halogen atoms, aldehyde groups, ester groups, acyl chloride groups, acyl anhydride groups, tosyl groups, mesyl groups, or brosyl groups, among others, that can be displaced by reactive nucleophilic atoms present within a kynureninase), aryl or heteroaryl linkers, such as benzyl, napthyl, or pyridyl groups containing two halomethyl groups that can be displaced by reactive nucleophilic atoms present within a kynureninase. Exemplary linkers include succinimidyl 4-(N-maleimidomethyl)-cyclohexane-L-carboxylate (SMCC), N-succinimidyl iodoacetate (SIA), sulfo-SMCC, m-maleimidobenzoyl-N-hydroxysuccinimidyl ester (MBS), sulfo-MBS, and succinimidyl iodoacetate, among others described, for instance, Liu et al., 18:690-697, 1979, the disclosure of which is incorporated herein by reference as it pertains to linkers for chemical conjugation. Additional linkers include the non-cleavable maleimidocaproyl linkers, which are described by Doronina et al., Bioconjugate Chem. 17:14-24, 2006, the disclosure of which is incorporated herein by reference as it pertains to linkers for chemical conjugation.

Additional linkers through which one component of a conjugate may be bound to another as described herein include linkers that are covalently bound to one component of the conjugate (e.g., a kynureninase) on one end of the linker and, on the other end of the linker, contain a chemical moiety formed from a coupling reaction between a reactive substituent present on the linker and a reactive substituent present within the other component of the conjugate (e.g., a PEG molecule described herein). Exemplary reactive substituents that may be present within a component of the conjugate include, without limitation, hydroxyl moieties of serine, threonine, and tyrosine residues; amino moieties of lysine residues; carboxyl moieties of aspartic acid and glutamic acid residues; and thiol moieties of cysteine residues, as well as propargyl, azido, haloaryl (e.g., fluoroaryl), haloheteroaryl (e.g., fluoroheteroaryl), haloalkyl, and haloheteroalkyl moieties of non-naturally occurring amino acids. Linkers useful in conjunction with the conjugates described herein include, without limitation, linkers containing chemical moieties formed by coupling reactions as depicted in Table 3 below. Curved lines designate points of attachment to each component of the conjugate Linkers that can be used to conjugate a PEG molecule to an enzyme include those that are covalently bound to the enzyme on one end of the linker and, on the other end of the linker, contain a chemical moiety formed from a coupling reaction between a reactive substituent present on the linker and a reactive substituent present within one of the side chains of the amino acid residues present as part of the enzyme. Reactive substituents that may be present within the kynureninase enzyme include, without limitation, hydroxyl moieties of serine, threonine, and tyrosine residues; amino moieties of lysine residues; carboxyl moieties of aspartic acid and glutamic acid residues; and thiol moieties of cysteine residues, as well as propargyl, azido, haloaryl (e.g., fluoroaryl), haloheteroaryl (e.g., fluoroheteroaryl), haloalkyl, and haloheteroalkyl moieties of non-naturally occurring amino acids.

TABLE 3

| Exemplary chemical moieties formed by coupling reactions in the formation of kynureninase homodimer conjugates | |
|---|---|
| Exemplary Coupling Reactions | Chemical Moiety Formed by Coupling Reactions |
| [3 + 2] Cycloaddition | 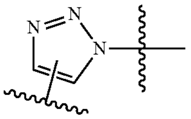 |
| [3 + 2] Cycloaddition | 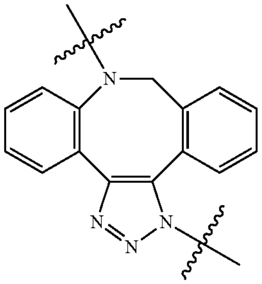 [SMILES: *N1Cc2ccccc2-c2c(nnn2*)-c2ccccc21] |
| [3 + 2] Cycloaddition, Esterification | 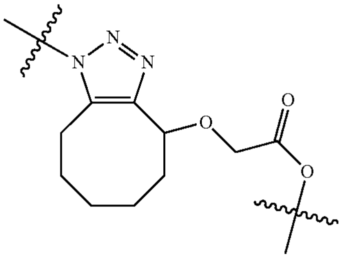 [SMILES: *OC(=O)COC1CCCCCc2c1nnn2*] |
| [3 + 2] Cycloaddition, Esterification | 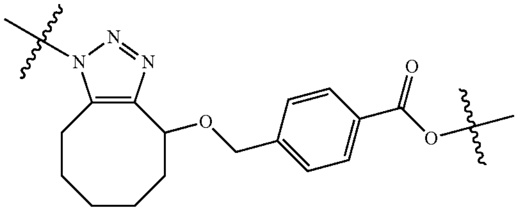 [SMILES: *OC(=O)c1ccc(COC2CCCCCc3c2nnn3*)cc1] |
| [3 + 2] Cycloaddition, Esterification | 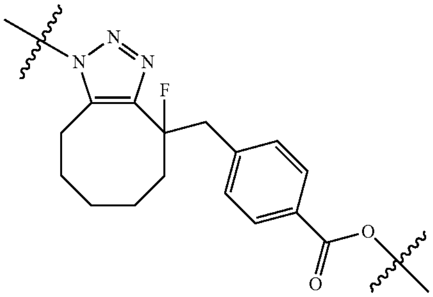 [SMILES: *OC(=O)c1ccc(CC2(F)CCCCCc3c2nnn3*)cc1] |
| [3 + 2] Cycloaddition, Esterification | 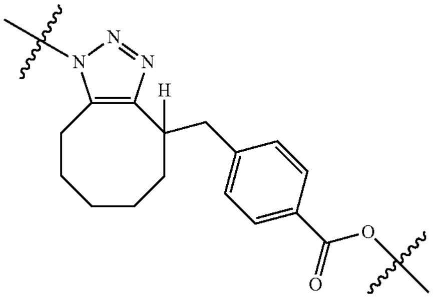 |

TABLE 3-continued
| Exemplary chemical moieties formed by coupling reactions in the formation of kynureninase homodimer conjugates | |
|---|---|
| Exemplary Coupling Reactions | Chemical Moiety Formed by Coupling Reactions |
| [3 + 2] Cycloaddition, Esterification | 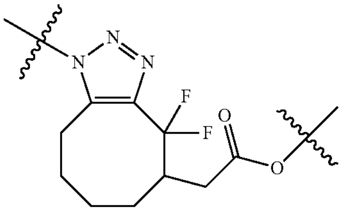 [SMILES: *OC(=O)CC1CCCCc2c(nnn2*)C1(F)F] |
| [3 + 2] Cycloaddition, Esterification | 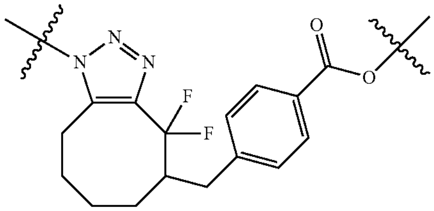 [SMILES: *OC(=O)c1ccc(CC2CCCCc3c(nnn3*)C2(F)F)cc1] |
| [3 + 2] Cycloaddition, Esterification | 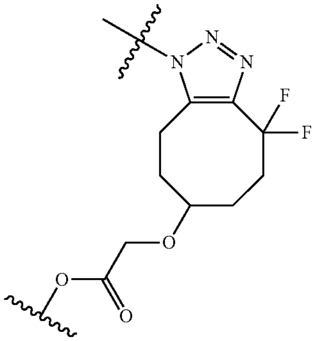 [SMILES: *OC(=O)COC1CCc2c(nnn2*)C(F)(F)CC1] |
| [3 + 2] Cycloaddition, Esterification | 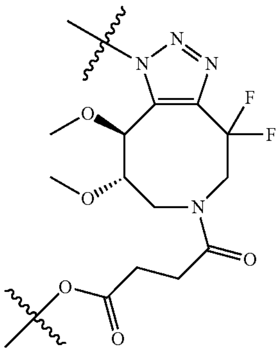 [SMILES: *OC(=O)CCC(=O)N1C[C@H](OC)[C@@H](OC)c2c(nnn2*)C(F)(F)C1] |

TABLE 3-continued
| Exemplary chemical moieties formed by coupling reactions in the formation of kynureninase homodimer conjugates | |
|---|---|
| Exemplary Coupling Reactions | Chemical Moiety Formed by Coupling Reactions |
| [3 + 2] Cycloaddition, Esterification | 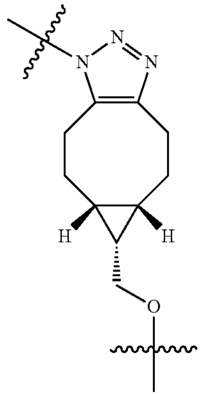 [SMILES: *OC[C@@H]1[C@@H]2CCc3c(nnn3*)CC[C@@H]21] |
| [3 + 2] Cycloaddition, Esterification | 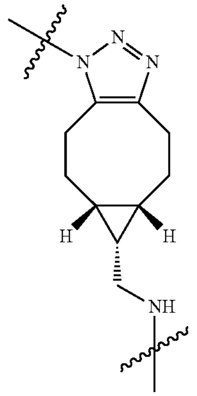 [SMILES: *NC[C@@H]1[C@@H]2CCc3c(nnn3*)CC[C@@H]21] |
| [3 + 2] Cycloaddition, Esterification | 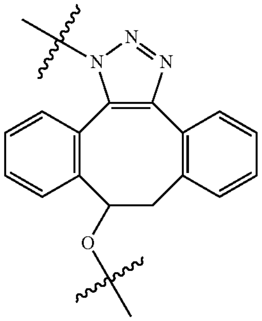 [SMILES: *OC1Cc2ccccc2-c2nnn(*)c2-c2ccccc21] |
| [3 + 2] Cycloaddition, Etherification | 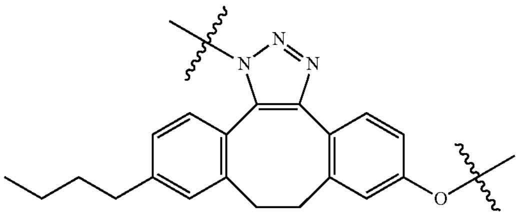 [SMILES: *Oc1ccc2c(c1)CCc1cc(CCCC)ccc1-c1c-2nnn1*] |

TABLE 3-continued

Exemplary chemical moieties formed by coupling reactions in the formation of kynureninase homodimer conjugates

| Exemplary Coupling Reactions | Chemical Moiety Formed by Coupling Reactions |
|---|---|
| [3 + 2] Cycloaddition | 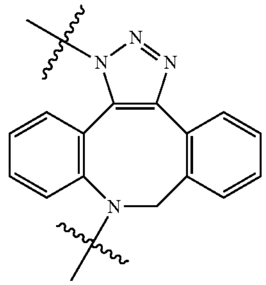 [SMILES: *N1Cc2ccccc2-c2nnn(*)c2-c2ccccc21] |
| Michael addition | 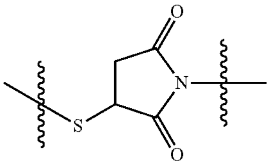 [SMILES: *SC1CC(=O)N(*)C1=O] |
| Michael addition | 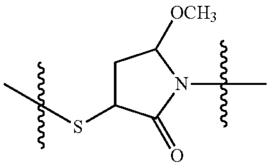 [SMILES: *SC1CC(OC)N(*)C1=O] |
| Imine condensation, Amidation | 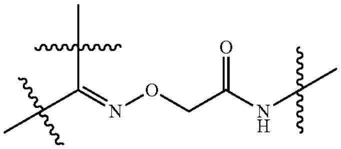 [SMILES: *NC(=O)CON=C(*)*] |
| Imine condensation | 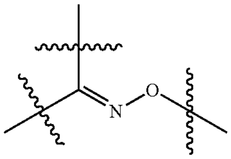 [SMILES: *ON=C(*)*] |
| Disulfide formation | 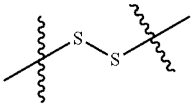 [SMILES: *SS*] |
| Thiol alkylation | 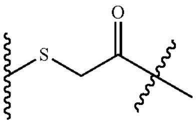 [SMILES: *SCC(*)=O] |
| Condensation, Michael addition | 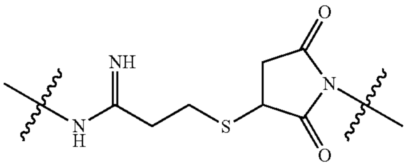 [SMILES: *NC(=N)CCSC1CC(=O)N(*)C1=O] |

Recombinant Expression of Kynureninases in Host Cells

The present disclosure includes compositions and methods for expressing kynureninase proteins recombinantly from a host cell, such as a prokaryotic or eukaryotic producer cell. Exemplary methods that can be used for effectuating the expressing a kynureninase protein in a host cell are described in further detail in the sections that follow.

Polynucleotides Encoding Kynureninases

One platform that can be used to express a kynureninase protein from a host cell, such as a mammalian cell, is by way of the stable incorporation of one or more genes encoding the kynureninase into the host cell genome (e.g., by integration into the nuclear genome of a mammalian cell). These genes are polynucleotides that encode the primary amino acid sequence of the corresponding protein. In order to introduce such exogenous genes into a mammalian cell, these genes can be incorporated into a vector. Vectors can be introduced into a cell by a variety of methods, including transformation, transfection, direct uptake, projectile bombardment, and by encapsulation of the vector in a liposome. Examples of suitable methods of transfecting or transforming cells are calcium phosphate precipitation, electroporation, microinjection, infection, lipofection, and direct uptake. Such methods are described in more detail, for example, in Green et al., Molecular Cloning: A Laboratory Manual, Fourth Edition (Cold Spring Harbor University Press, New York (2014)); and Ausubel et al., Current Protocols in Molecular Biology (John Wiley & Sons, New York (2015)), the disclosures of each of which are incorporated herein by reference.

Genes encoding therapeutic proteins of the disclosure can also be introduced into mammalian cells by targeting a vector containing a gene encoding such an agent to cell membrane phospholipids. For example, vectors can be targeted to the phospholipids on the extracellular surface of the cell membrane by linking the vector molecule to a VSV-G protein, a viral protein with affinity for all cell membrane phospholipids. Such, a construct can be produced using methods well known to those of skill in the field.

Recognition and binding of the polynucleotide encoding one or more therapeutic proteins of the disclosure by mammalian RNA polymerase is important for gene expression. As such, one may include sequence elements within the polynucleotide that exhibit a high affinity for transcription factors that recruit RNA polymerase and promote the assembly of the transcription complex at the transcription initiation site. Such sequence elements include, e.g., a mammalian promoter, the sequence of which can be recognized and bound by specific transcription initiation factors and ultimately RNA polymerase. Examples of mammalian promoters have been described in Smith et al., Mol. Sys. Biol., 3:73, online publication, the disclosure of which is incorporated herein by reference.

Once a polynucleotide encoding one or more therapeutic proteins has been incorporated into the nuclear DNA of a mammalian cell, the transcription of this polynucleotide can be induced by methods known in the art. For example, expression can be induced by exposing the mammalian cell to an external chemical reagent, such as an agent that modulates the binding of a transcription factor and/or RNA polymerase to the mammalian promoter and thus regulates gene expression. The chemical reagent can serve to facilitate the binding of RNA polymerase and/or transcription factors to the mammalian promoter, e.g., by removing a repressor protein that has bound the promoter. Alternatively, the chemical reagent can serve to enhance the affinity of the mammalian promoter for RNA polymerase and/or transcription factors such that the rate of transcription of the gene located downstream of the promoter is increased in the presence of the chemical reagent. Examples of chemical reagents that potentiate polynucleotide transcription by the above mechanisms are tetracycline and doxycycline. These reagents are commercially available (Life Technologies, Carlsbad, Calif.) and can be administered to a mammalian cell in order to promote gene expression according to established protocols.

Other DNA sequence elements that may be included in polynucleotides for use in the compositions and methods described herein are enhancer sequences. Enhancers represent another class of regulatory elements that induce a conformational change in the polynucleotide containing the gene of interest such that the DNA adopts a three-dimensional orientation that is favorable for binding of transcription factors and RNA polymerase at the transcription initiation site. Thus, polynucleotides for use in the compositions and methods described herein include those that encode one or more therapeutic proteins and additionally include a mammalian enhancer sequence. Many enhancer sequences are now known from mammalian genes, and examples are enhancers from the genes that encode mammalian globin, elastase, albumin, α-fetoprotein, and insulin. Enhancers for use in the compositions and methods described herein also include those that are derived from the genetic material of a virus capable of infecting a eukaryotic cell. Examples are the SV40 enhancer on the late side of the replication origin (bp 100-270), the cytomegalovirus early promoter enhancer, the polyoma enhancer on the late side of the replication origin, and adenovirus enhancers. Additional enhancer sequences that induce activation of eukaryotic gene transcription are disclosed in Yaniv et al., Nature 297:17 (1982).

Fusion Proteins

Some embodiments of the present disclosure concern fusion proteins. These molecules may have a native or modified kynureninase linked at the N- or C-terminus to a heterologous domain. For example, fusions may also employ leader sequences from other species to permit the recombinant expression of a protein in a heterologous host. Another useful fusion includes the addition of a protein affinity tag, such as a serum albumin affinity tag or six histidine residues, or an immunologically active domain, such as an antibody epitope, preferably cleavable, to facilitate purification of the fusion protein. Non-limiting affinity tags include polyhistidine, chitin binding protein (CBP), maltose binding protein (MBP), and glutathione-S-transferase (GST).

In a particular embodiment, the kynureninase may be linked to a peptide that increases the in vivo half-life, such as an XTEN polypeptide (Schellenberger et al., 2009), IgG Fc domain, albumin, or albumin binding peptide.

Methods of generating fusion proteins are well known to those of skill in the art. Such proteins can be produced, for example, by de novo synthesis of the complete fusion protein, or by attachment of the DNA sequence encoding the heterologous domain, followed by expression of the intact fusion protein. Production of fusion proteins that recover the functional activities of the parent proteins may be facilitated by connecting genes with a bridging DNA segment encoding a peptide linker that is spliced between the polypeptides connected in tandem. The linker would be of sufficient length to allow proper folding of the resulting fusion protein.

Enzymatic Kynurenine Degradation for Therapy

In some embodiments, the kynureninases of the disclosure may be used for the treatment of diseases, including cancers that are sensitive to kynurenine depletion, with enzymes that deplete kynurenine, to prevent tumor-mediated tolerogenic effects and instead mediate tumor-ablating pro-inflammatory responses. In some embodiments, kynureninases are contemplated for use in treating tumors expressing IDO1, IDO2, and/or TDO.

Some embodiments of the present disclosure provide a modified kynureninase for treating diseases, such as tumors. Particularly, the modified kynureninases may have human polypeptide sequences and thus may prevent allergic reactions in human patients, allow repeated dosing, and increase the therapeutic efficacy.

Tumors for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, carcinoma, lymphoma, blastoma, sarcoma, leukemia, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer and gastrointestinal stromal cancer), pancreatic cancer, glioblastoma, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, melanoma, superficial spreading melanoma, lentigo malignant melanoma, acral lentiginous melanomas, nodular melanomas, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's macroglobulinemia), chronic lymphocytic leukemia (CLL), acute lymphoblastic leukemia (ALL), Hairy cell leukemia, multiple myeloma, acute myeloid leukemia (AML) and chronic myeloblastic leukemia.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

The kynureninase may be used herein as an antitumor agent in a variety of modalities for depleting kynurenine and/or kynurenine-derived metabolites from tumor tissue, or the circulation of a mammal with cancer, or for depletion of kynurenine where its depletion is considered desirable. Depletion can be conducted in vivo in the circulation of a mammal, in vitro in cases where kynurenine and/or kynurenine-derived metabolites depletion in tissue culture or other biological mediums is desired, and in ex vivo procedures where biological fluids, cells, or tissues are manipulated outside the body and subsequently returned to the body of the patient mammal. Depletion of kynurenine from circulation, culture media, biological fluids, or cells is conducted to reduce the amount of kynurenine accessible to the material being treated, and therefore comprises contacting the material to be depleted with a kynurenine-depleting amount of the kynureninase under kynurenine-depleting conditions as to degrade the ambient kynurenine in the material being contacted.

The depletion may be directed to the nutrient source for the cells, and not necessarily the cells themselves. Therefore, in an in vivo application, treating a tumor cell includes contacting the nutrient medium for a population of tumor cells with the kynureninase. In this embodiment, the medium may be blood, lymphatic fluid, spinal fluid and the like bodily fluid where kynurenine depletion is desired.

Kynurenine- and/or kynurenine-derived metabolites depletion efficiency can vary widely depending upon the application, and typically depends upon the amount of kynurenine present in the material, the desired rate of depletion, and the tolerance of the material for exposure to kynureninase. Kynurenine and kynurenine metabolite levels in a material, and therefore rates of kynurenine and kynurenine metabolite depletion from the material, can readily be monitored by a variety of chemical and biochemical methods well known in the art. Exemplary kynurenine-depleting amounts are described further herein, and can range, for example, from 0.001 to 1,000 units (U) of kynureninase, depending, for example, on the subject being treated and the severity of the disease.

Kynurenine-depleting conditions are buffer and temperature conditions compatible with the biological activity of a kynureninase, and include moderate temperature, salt, and pH conditions compatible with the enzyme, for example, physiological conditions. Exemplary conditions include about 4-40° C., ionic strength equivalent to about 0.05 to 0.2 M NaCl, and a pH of about 5 to 9, while physiological conditions are included.

In some embodiments, the disclosure contemplates methods of using a kynureninase as an antitumor agent, and therefore comprises contacting a population of tumor cells with a therapeutically effective amount of kynureninase for a time period sufficient to inhibit tumor cell growth.

A therapeutically effective amount of a kynureninase is a predetermined amount calculated to achieve the desired effect, i.e., to deplete kynurenine in the tumor tissue or in a patients circulation, and thereby mediate a tumor-ablating pro-inflammatory response. Thus, the dosage ranges for the administration of kynureninase of the disclosure are those large enough to produce the desired effect in which the symptoms of tumor cell division and cell cycling are reduced. The dosage should not be so large as to cause adverse side effects, such as hyperviscosity syndromes, pulmonary edema, congestive heart failure, neurological effects, and the like. Generally, the dosage will vary with age of, condition of, sex of, and extent of the disease in the patient and can be determined by one of skill in the art. The dosage can be adjusted by the individual physician in the event of any complication.

The kynureninase can be administered parenterally by injection or by gradual infusion over time. The kynureninase can be administered intravenously, intraperitoneally, orally, intramuscularly, subcutaneously, intracavity, transdermally, dermally, can be delivered by peristaltic means, can be injected directly into the tissue containing the tumor cells, or can be administered by a pump connected to a catheter that may contain a potential biosensor for kynurenine.

The therapeutic compositions containing kynureninase are conventionally administered intravenously, as by injection of a unit dose, for example.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for initial administration and booster shots are also contemplated and are typified by an initial administration followed by repeated doses at one or more hour intervals by a subsequent injection or other administration. Exemplary multiple administrations are described herein and are particularly preferred to maintain continuously high serum and tissue levels of kynureninase and conversely low serum and tissue levels of kynurenine. Alternatively, continuous intravenous infusion sufficient to maintain concentrations in the blood in the ranges specified for in vivo therapies are contemplated.

Proteins and Peptides

In some embodiments, the present disclosure concerns novel compositions comprising at least one protein or peptide, such as a kynureninase. These peptides may be comprised in a fusion protein or conjugated to an agent as described supra.

As used herein, a protein or peptide generally refers, but is not limited to, a protein of greater than about 200 amino acids, up to a full-length sequence translated from a gene; a polypeptide of greater than about 100 amino acids; and/or a peptide of from about 3 to about 100 amino acids. For convenience, the terms "protein," "polypeptide," and "peptide" are used interchangeably herein.

As used herein, an "amino acid residue" refers to any naturally occurring amino acid, any amino acid derivative, or any amino acid mimic known in the art. In some embodiments, the residues of the protein or peptide are sequential, without any non-amino acids interrupting the sequence of amino acid residues. In some embodiments, the sequence may comprise one or more non-amino acid moieties. In particular embodiments, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid.

Proteins or peptides may be made by any technique known to those of skill in the art, including the expression of proteins, polypeptides, or peptides through standard molecular biological techniques, the isolation of proteins or peptides from natural sources, or the chemical synthesis of proteins or peptides. The nucleotide and protein, polypeptide, and peptide sequences corresponding to various genes have been previously disclosed, and may be found at computerized databases known to those of ordinary skill in the art. One such database is the National Center for Biotechnology Information's Genbank and GenPept databases (available on the world wide web at ncbi.nlm.nih.gov/). The coding regions for known genes may be amplified and/or expressed using the techniques disclosed herein or as would be known to those of ordinary skill in the art. Alternatively, various commercial preparations of proteins, polypeptides, and peptides are known to those of skill in the art.

Pharmaceutical Compositions

It is contemplated that the novel kynureninase can be administered systemically or locally to inhibit tumor cell growth and, most preferably, to kill cancer cells in cancer patients with locally advanced or metastatic cancers. They can be administered intravenously, intrathecally, and/or intraperitoneally. They can be administered alone or in combination with anti-proliferative drugs. In one embodiment, they are administered to reduce the cancer load in the patient prior to surgery or other procedures. Alternatively, they can be administered after surgery to ensure that any remaining cancer (e.g., cancer that the surgery failed to eliminate) does not survive.

It is not intended that the present disclosure be limited by the particular nature of the therapeutic preparation. For example, such compositions can be provided in formulations together with physiologically tolerable liquid, gel, or solid carriers, diluents, and excipients. These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual subjects.

Such compositions are typically prepared as liquid solutions or suspensions, as injectables. Suitable diluents and excipients are, for example, water, saline, dextrose, glycerol, or the like, and combinations thereof. In addition, if desired, the compositions may contain minor amounts of auxiliary substances, such as wetting or emulsifying agents, stabilizing agents, or pH buffering agents.

Where clinical applications are contemplated, it may be necessary to prepare pharmaceutical compositions comprising proteins, antibodies, and drugs in a form appropriate for the intended application. Generally, pharmaceutical compositions may comprise an effective amount of one or more kynureninase or additional agents dissolved or dispersed in a pharmaceutically acceptable carrier. The phrases "pharmaceutical or pharmacologically acceptable" refers to molecular entities and compositions that do not produce an adverse, allergic, or other untoward reaction when administered to an animal, such as, for example, a human, as appropriate. The preparation of a pharmaceutical composition that contains at least one kynureninase isolated by the method disclosed herein, or additional active ingredient will be known to those of skill in the art in light of the present disclosure, as exemplified by Remington's Pharmaceutical Sciences, 18th Ed., 1990, incorporated herein by reference. Moreover, for animal (e.g., human) administration, it will be understood that preparations should meet sterility, pyrogenicity, general safety, and purity standards as required by the FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed., 1990, incorporated herein by reference). Except insofar as any conventional carrier is incompatible with the active ingredient, its use in the pharmaceutical compositions is contemplated.

Some embodiments of the present disclosure may comprise different types of carriers depending on whether it is to be administered in solid, liquid, or aerosol form, and whether it needs to be sterile for the route of administration, such as injection. The compositions can be administered intravenously, intradermally, transdermally, intrathecally, intraarterially, intraperitoneally, intranasally, intravaginally, intrarectally, intramuscularly, subcutaneously, mucosally, orally, topically, locally, by inhalation (e.g., aerosol inhalation), by injection, by infusion, by continuous infusion, by localized perfusion bathing target cells directly, via a catheter, via a lavage, in lipid compositions (e.g., liposomes), or by other methods or any combination of the forgoing as would be known to one of ordinary skill in the art (see, for example, Remington's Pharmaceutical Sciences, 18th Ed., 1990, incorporated herein by reference).

The modified polypeptides may be formulated into a composition in a free base, neutral, or salt form. Pharmaceutically acceptable salts include the acid addition salts, e.g., those formed with the free amino groups of a proteinaceous composition, or which are formed with inorganic acids, such as, for example, hydrochloric or phosphoric acids, or such organic acids as acetic, oxalic, tartaric, or mandelic acid. Salts formed with the free carboxyl groups can also be derived from inorganic bases, such as, for example, sodium, potassium, ammonium, calcium, or ferric hydroxides; or such organic bases as isopropylamine, trimethylamine, histidine, or procaine. Upon formulation, solutions will be administered in a manner compatible with the dosage formulation and in such amount as is therapeutically effective. The formulations are easily administered in a variety of dosage forms, such as formulated for parenteral administrations, such as injectable solutions, or aerosols for delivery to the lungs, or formulated for alimentary administrations, such as drug release capsules and the like.

Further in accordance with some embodiments of the present disclosure, the composition suitable for administration may be provided in a pharmaceutically acceptable carrier with or without an inert diluent. The carrier should be assimilable and includes liquid, semi-solid, i.e., pastes, or solid carriers. Except insofar as any conventional media, agent, diluent, or carrier is detrimental to the recipient or to the therapeutic effectiveness of the composition contained therein, its use in administrable composition for use in practicing the methods is appropriate. Examples of carriers or diluents include fats, oils, water, saline solutions, lipids, liposomes, resins, binders, fillers, and the like, or combinations thereof. The composition may also comprise various antioxidants to retard oxidation of one or more component. Additionally, the prevention of the action of microorganisms can be brought about by preservatives, such as various antibacterial and antifungal agents, including but not limited to parabens (e.g., methylparabens, propylparabens), chlorobutanol, phenol, sorbic acid, thimerosal or combinations thereof.

In accordance with some embodiments of the present disclosure, the composition is combined with the carrier in any convenient and practical manner, i.e., by solution, suspension, emulsification, admixture, encapsulation, absorption, and the like. Such procedures are routine for those skilled in the art.

In a specific embodiment of the present disclosure, the composition is combined or mixed thoroughly with a semi-solid or solid carrier. The mixing can be carried out in any convenient manner, such as grinding. Stabilizing agents can be also added in the mixing process in order to protect the composition from loss of therapeutic activity, i.e., denaturation in the stomach. Examples of stabilizers for use in a composition include buffers, amino acids, such as glycine and lysine, carbohydrates, such as dextrose, mannose, galactose, fructose, lactose, sucrose, maltose, sorbitol, mannitol, etc.

In further embodiments, the present disclosure may concern the use of a pharmaceutical lipid vehicle composition that includes kynureninases, one or more lipids, and an aqueous solvent. As used herein, the term "lipid" will be defined to include any of a broad range of substances that is characteristically insoluble in water and extractable with an organic solvent. This broad class of compounds is well known to those of skill in the art, and as the term "lipid" is used herein, it is not limited to any particular structure. Examples include compounds that contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether- and ester-linked fatty acids, polymerizable lipids, and combinations thereof. Of course, compounds other than those specifically described herein that are understood by one of skill in the art as lipids are also encompassed by the compositions and methods.

One of ordinary skill in the art would be familiar with the range of techniques that can be employed for dispersing a composition in a lipid vehicle. For example, the kynureninase or a fusion protein thereof may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition administered to an animal patient can be determined by physical and physiological factors, such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In some embodiments, pharmaceutical compositions may comprise, for example, at least about 0.1% of an active compound. In some embodiments, an active compound may comprise between about 2% to about 75% of the weight of the unit, or between about 25% to about 60%, for example, and any range derivable therein. Naturally, the amount of active compound(s) in each therapeutically useful composition may be prepared in such a way that a suitable dosage will be obtained in any given unit dose of the compound. Factors, such as solubility, bioavailability, biological half-life, route of administration, product shelf life, as well as other pharmacological considerations, will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 milligram/kg/body weight or more per administration, and any range derivable therein. In non-limiting examples of a derivable range from the numbers listed herein, a range of about 5 milligram/kg/body weight to about 100 milligram/kg/body weight, about 5 microgram/kg/body weight to about 500 milligram/kg/body weight, etc., can be administered, based on the numbers described above.

Combination Treatments

In some embodiments, the compositions and methods of the present embodiments involve administration of a kynureninase in combination with a second or additional therapy. Such therapy can be applied in the treatment of any disease that is associated with kynurenine dependency. For example, the disease may be cancer.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve administering a kynureninase and a second therapy. The second therapy may or may not have a direct cytotoxic effect. For example, the second therapy may be an agent that upregulates the immune system without having a direct cytotoxic effect. A tissue, tumor, or cell can be exposed to one or more compositions or pharmacological formulation(s) comprising one or more of the agents (e.g., a kynureninase or an anti-cancer agent), or by exposing the tissue, tumor, and/or cell with two or more distinct compositions or formulations, wherein one composition provides 1) a kynureninase, 2) an anti-cancer agent, or 3) both a kynureninase and an anti-cancer agent. Also, it is contemplated that such a combination therapy can be used in conjunction with chemotherapy, radiotherapy, surgical therapy, or immunotherapy.

A kynureninase may be administered before, during, after, or in various combinations relative to an anti-cancer treatment. The administrations may be in intervals ranging from concurrently to minutes to days to weeks. In embodiments where the kynureninase is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the kynureninase and the anti-cancer therapy within about 12 to 24 or 72 h of each other and, more particularly, within about 6-12 h of each other. In some situations, it may be desirable to extend the time period for treatment significantly where several days (2, 3, 4, 5, 6, or 7) to several weeks (1, 2, 3, 4, 5, 6, 7, or 8) lapse between respective administrations.

In some embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below a kynureninase is "A" and an anti-cancer therapy is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A B/A/B/A B/A/A/B A/A/A/B B/A/A/A A/B/A/A A/A/B/A

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

EXAMPLES

The following examples are put forth so as to provide those of ordinary skill in the art with a description of how the compositions and methods described herein may be used, made, and evaluated, and are intended to be purely exemplary of the disclosure and are not intended to limit the scope of what the inventors regard as their disclosure.

Example 1. Generation of PEGylated Kynureninase Homodimer

An exemplary method of generating PEGylated kynureninase homodimer for use in the compositions and methods described herein is by way of chemical conjugation. Kynureninase can be dissolved in an aqueous buffer with a pH of 8.5, comprising 100 mM disodium phosphate, to which the solid PEGylation agent, such as Methoxy-PEG-$CH_2COO$—N-hydroxysuccinimide (NHS) with a molecular weight of 5 kDa, can be added with an input ratio of, for example, 20:1, 30:1, 40:1, 50:1 or 60:1 PEG molecules to kynureninase homodimer. This reaction mixture can be left at about 22° C. for about 30 minutes.

Additional exemplary methods for generating PEGylated kynureninase homodimer can involve a kynureninase homodimer in an aqueous buffer, comprising 50 mM sodium acetate, 230 mM NaCl, 0.1 mM pyridoxal phosphate, adjusted to pH 8.6 using 0.6 M sodium borate, pH 9. A PEGylation agent, such as Methoxy-PEG-$CH_2COO$—NHS with a molecular weight of 5 kDa, can be dissolved in 3 mM HCl such that a final concentration of about 0.2 g PEG per milliliter of HCl is achieved. This PEG solution can be added to the kynureninase solution in a controlled manner such that a final ratio of 30:1 PEG to kynureninase homodimer is achieved in the reaction mixture. The reaction can occur at about 22° C. for 30 minutes.

Figure 1A:
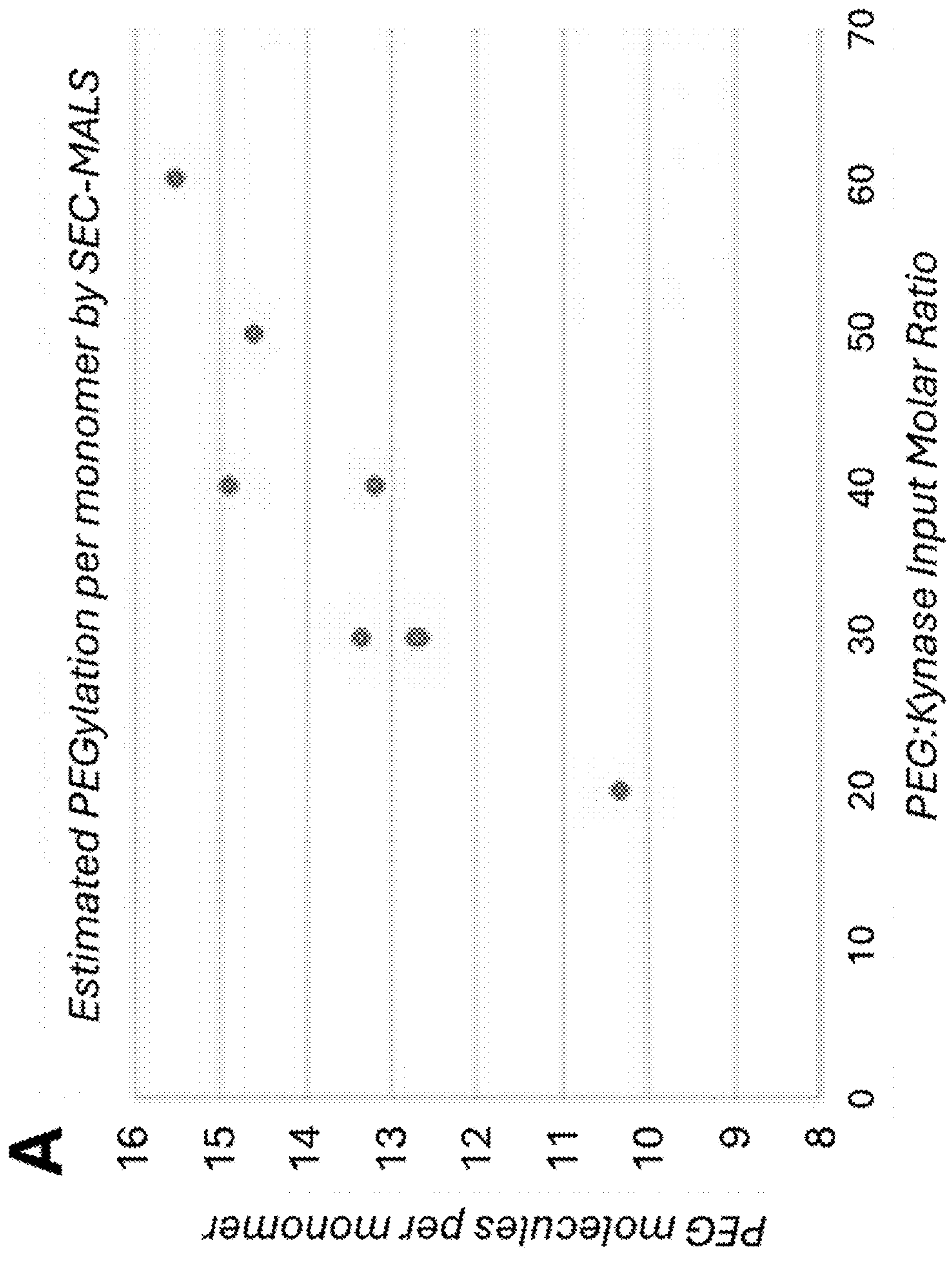
FIGS. 1A-1F: Generation of PEGylated kynureninase conjugates. A) Resulting number of conjugated PEG molecules per kynureninase monomers for input ratio ranging from 20:1-60:1 of PEG:kynureninase homodimer. B) Resulting number of conjugated PEG molecules per kynureninase homodimer for input ratios ranging from 20:1-60:1 of PEG:kynureninase homodimer. C) Efficiency of conjugation reaction between PEG molecules and kynureninase with input ratios of 20:1-60:1 of PEG:kynureninase homodimer. D) SEC-MALS HPLC of PEGylated kynureninase homodimer product resulting from an input ratio of 20:1 PEG to kynureninase homodimer. E) SEC-MALS HPLC of PEGylated kynureninase homodimer product resulting from an input ratio of 30:1 PEG to kynureninase homodimer. F) SEC-MALS HPLC of PEGylated kynureninase homodimer product resulting from an input ratio of 60:1 PEG to kynureninase homodimer.
Figure 1B:
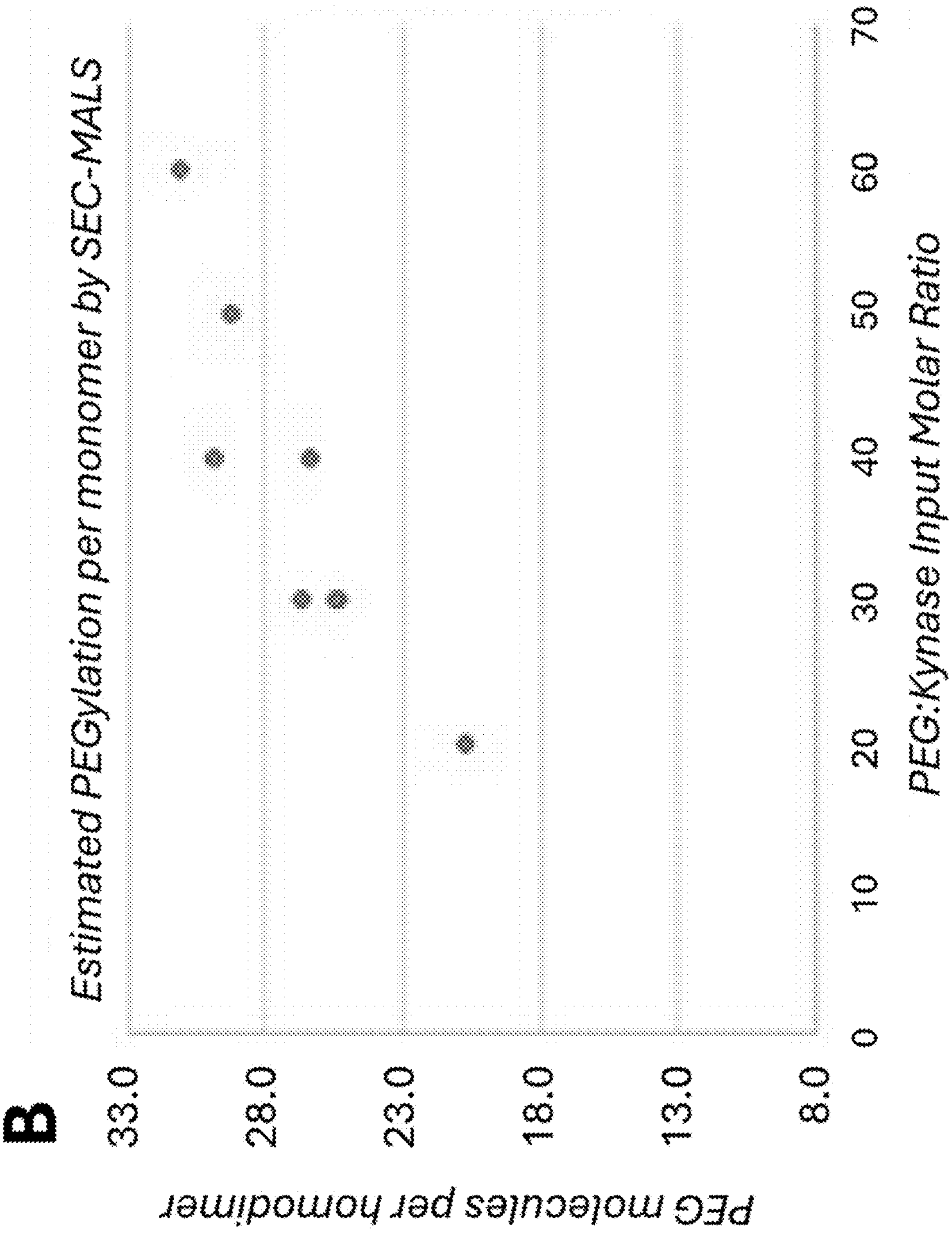
Figure 1C:
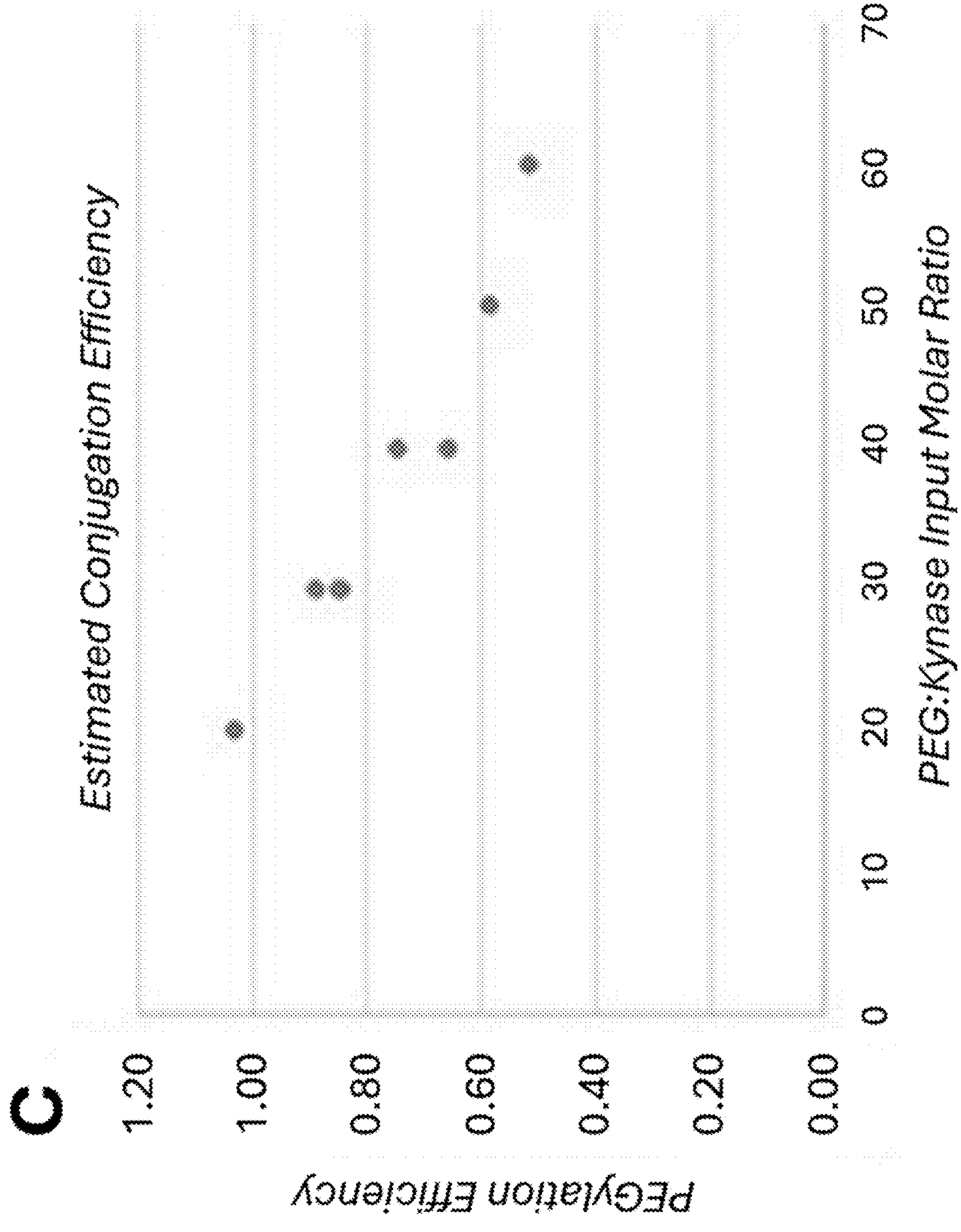
Figure 1D:
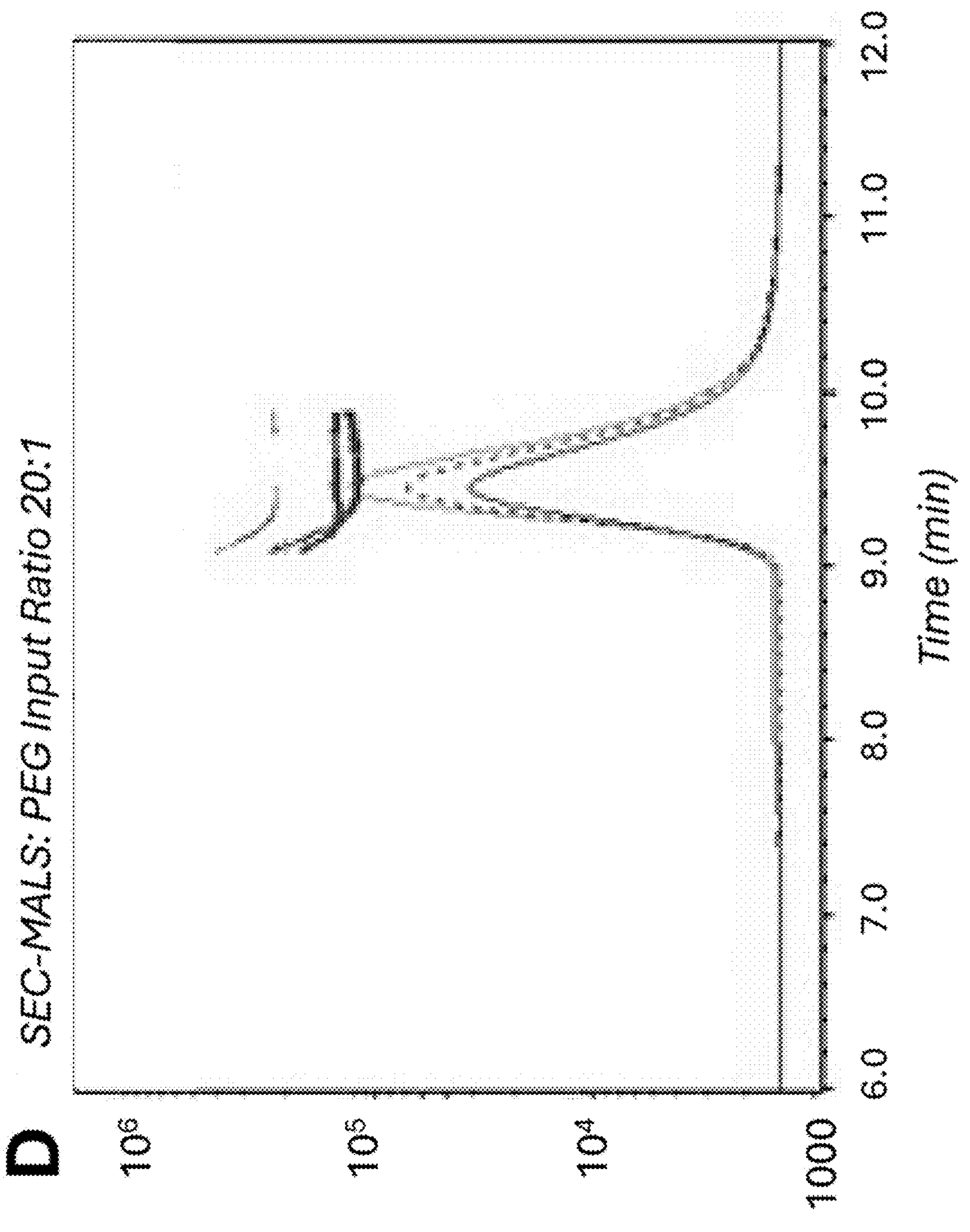
Figure 1E:
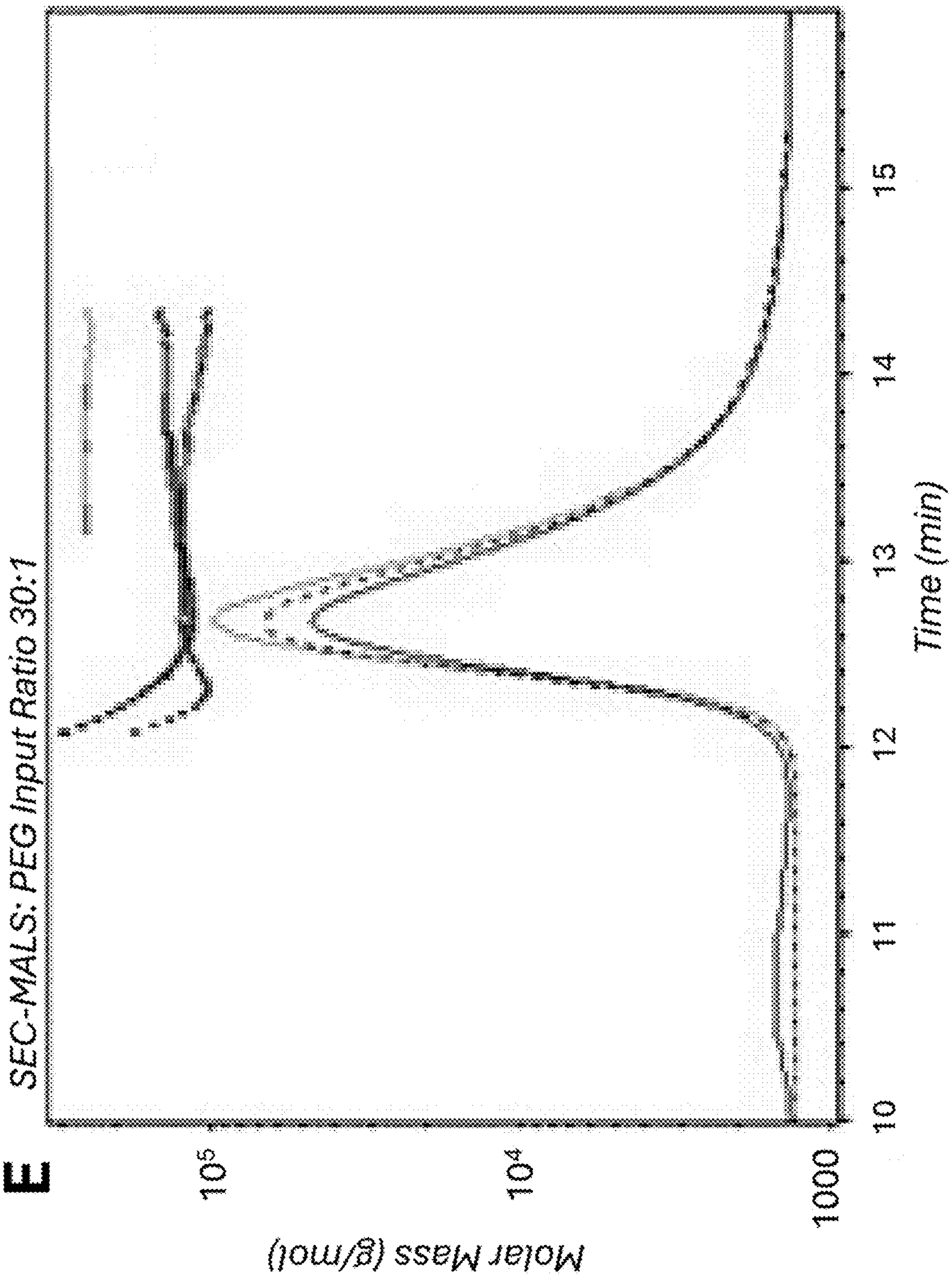
Figure 1F:
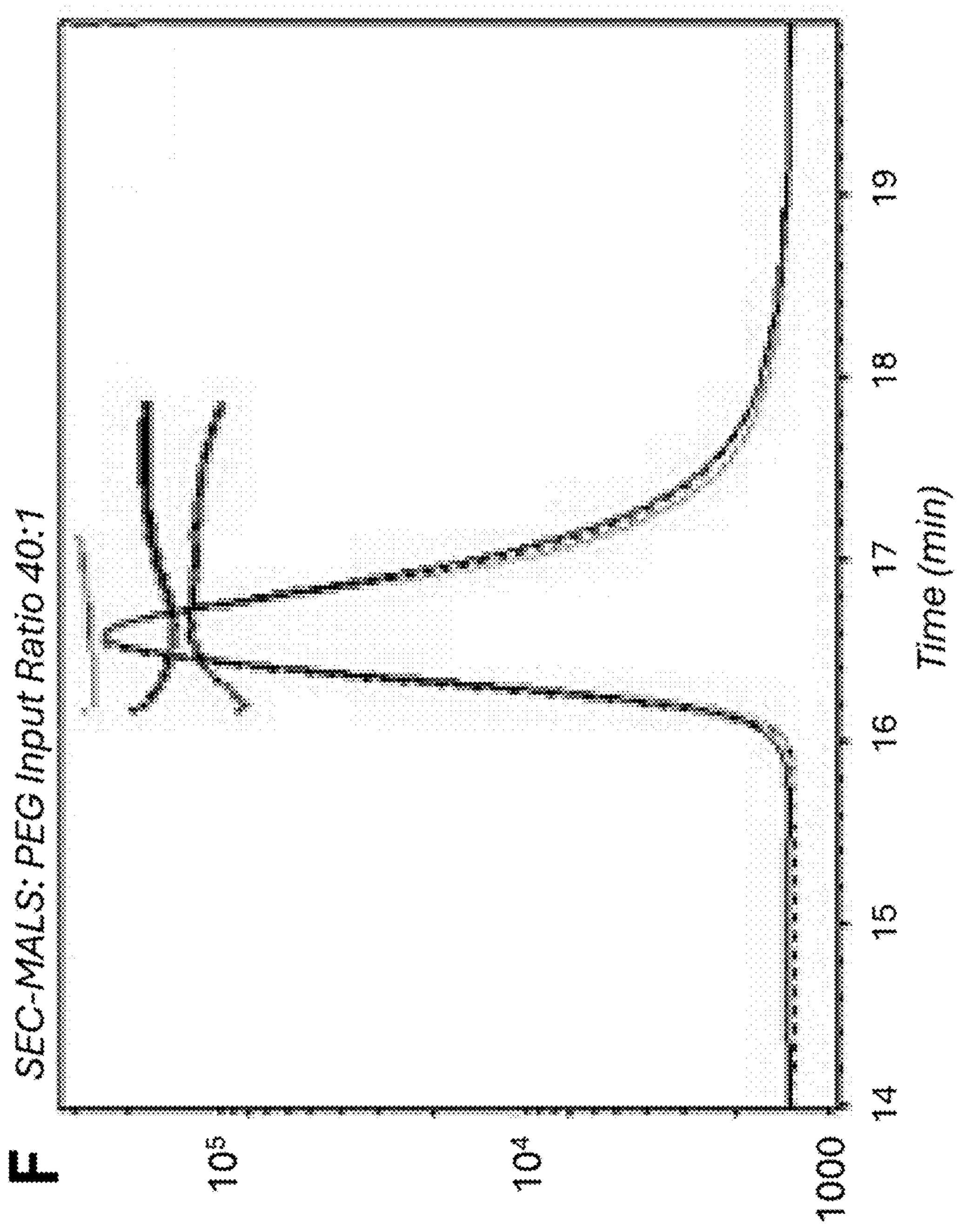

The PEGylated homodimer can then be analyzed using size exclusion chromatography with multi-angle light-scatter using a TSKgel G3000 SWxl column with a flow rate of 0.6 mL/min over 25 min in a 25 mM $NaH_2PO_4$, 150 mM NaCl buffer at 25° C. resulting in chromatograms for each respective input PEG:kynureninase ratio (FIGS. 1D-1F).

The resulting number of PEG molecules per kynureninase monomer and homodimer were calculated from the measured molecular weight of PEGylated kynureninase for various input ratios of PEG:kynureninase homodimer (FIGS. 1A-1B) along with the efficiency of the PEGylation reaction for each input ratio of PEG:kynureninase homodimer (FIG. 1C).

Example 2. Administration of a PEGylated Kynureninase Homodimer to a Patient Suffering from a Malignant Tumor According to the methods disclosed herein, a physician of skill in the art can treat a patient, such as a human patient, so as to reduce or alleviate symptoms of an IDO1, IDO2, or TDO expressing tumor. To this end, a physician of skill in the art can administer to the human patient the PEGylated kynureninase homodimer. The homodimer may be administered to the patient, for example, systemically (e.g., intravenously), by localized perfusion bathing target cells directly, via a catheter, via a lavage, in lipid compositions (e.g., liposomes), or by other methods or any combination of the forgoing as would be known to one of ordinary skill in the art to treat the tumor. The homodimer can also be administered to the patient by multiple routes of administration, for example, intravenously and intracerebroventricularly. Exemplary kynurenine-depleting amounts can range from 0.001 to 1,000 units (U) of kynureninase.

In combination with the PEGylated kynureninase homodimer, one or more anti-cancer therapies may be administered to the patient (e.g. radiation therapy, surgical therapy, an immunotherapy) to ablate the patient's tumor cells. Methods of cell ablation well known in the art, such as irradiation, may be used alone or in combination with one or more anti-cancer or anti-hyperproliferative therapies to ablate the patients tumor cells. These agents and/or treatments may ablate tumor cells by at least 5% (e.g., at least 5%, 10%, 15%, 20%, 25%, 30%, 35%, 40%, 45%, 50%, 60%, 70%, 80%, 90%, 99%, or more), as assessed by PET imaging techniques known in the art. The homodimer can be administered to the patient from, for example, 12 hours to 1 month (e.g., 12 hours, 24 hours, 72 hours, 1 week, 2 weeks, 3 weeks, 4, weeks) or more before or after treatment with a second or more anti-cancer therapy.

The homodimer can be administered to the patient in an amount sufficient to treat a tumor expressing IDO1, IDO2 or TDO2. A standard examination can also be performed by the physician before and after treatment to evaluate changes in tumor size. The patient may be evaluated, for example, 1 month, 2 months, 3 months, 4 months, 5 months, 6 months or more following administration of the homodimer depending on the route of administration used for treatment. A finding of reduced tumor size or reduced local kynureninase concentrations at the site of the tumor following administration of the PEGylated kynureninase homodimer provides an indication that the treatment has successfully treated the tumor expressing IDO1, IDO2 or TDO2.

Example 3. Optimization of Kynureninase Homodimer PEGylation Density for In Vivo Delivery In this example, purified kynureninase having the amino acid sequence of SEQ ID NO: 2 was conjugated with 5,000-dalton PEG using α-[3-(3-maleimido-1-oxopropyl) amino]propyl-w-methoxy PEG reagent (CAS #883993-35-9) at pH 8.5 for 30 minutes at room temperature. The conjugation reaction was performed with kynureninase concentrations of 5.5-8 mg/ml and direct addition of various molar equivalents of the 5 kDa PEG reagent (100:1, 80:1, 40:1, 20:1, and 10:1 PEGylation agent to kynureninase homodimer). Following conjugation, the final products were diafiltered into 1× phosphate buffered saline, pH 7.4, with 30 kDa molecular weight cutoff spin filters to remove any residual free PEG. Samples were analyzed by an isocratic size exclusion chromatography (SEC) method using a Superdex 200 10/300 column (FIG. 2A)

For testing PEGylated kynureninase homodimers, each female BALB/c mouse (6-8 weeks) was inoculated subcutaneously at the right flank with CT-26 tumor cells (1×105) in 0.1 ml of PBS for tumor development. The animals were randomized and dosed iv with vehicle (PBS pH7.4), or 10 mg/kg differentially pegylated kynureninase having the amino acid sequence of SEQ ID NO: 2 was started when the average tumor volume reached approximately 200 $mm^3$. At 6, 24, 48, 72 & 120 hours after dosing, mice were terminally bled (n=4 mice/time point) and the plasma samples were immediately quenched with acid containing Internal Standard (IS) solution and processed for LC/MS analysis of Kynurenine (FIG. 2B). Tumor samples were collected from all groups, lysed with RIPA buffer, and 20 μg of tumor lysates were loaded onto SDS-PAGE gel for western blot analysis with anti-PEG antibody (Abcam #abS 1257; 1:2000 dilution) and anti-β-Actin antibody (Cell Signaling Technology #CST-4967). Chemiluminescence signals were detected and the intensity of individual bands was quantified using Alphaview SA densitometry software (FIG. 2C).

Other Embodiments

Various modifications and variations of the described disclosure will be apparent to those skilled in the art without departing from the scope and spirit of the disclosure. Although the disclosure has been described in connection with specific embodiments, it should be understood that the disclosure as claimed should not be unduly limited to such specific embodiments. Indeed, various modifications of the described modes for carrying out the disclosure that are obvious to those skilled in the art are intended to be within the scope of the disclosure.

Other embodiments are in the claims.

The invention claimed is:

1. A kynureninase homodimer covalently bound to one or more polyethylene glycol (PEG) molecules, wherein the ratio of PEG molecules to homodimer is from 15:1 to 30:1, wherein the homodimer comprises two polypeptide monomers each having an amino acid sequence that is at least 85% identical to the amino acid sequence of SEQ ID NO: 1, wherein each polypeptide monomer comprises the substitutions L72N, H102W, A282P, F306W, S408N, A436T, and N333T relative to SEQ ID NO: 1.

2. The homodimer of claim 1, wherein the ratio of PEG molecules to homodimer is from 20:1 to 30:1.

3. The homodimer of claim 1, wherein one or more of the PEG molecules each independently has a molecular weight of from about 1 kDa to about 10 kDa.

4. The homodimer of claim 3, wherein one or more of the PEG molecules each independently has a molecular weight of about 5 kDa.

5. The homodimer of claim 1, wherein the homodimer is covalently bound to the PEG molecule by way of one or more lysine or cysteine residues.

6. The homodimer of claim 1, wherein the homodimer comprises two polypeptide monomers each having an amino acid sequence that is at least 85% identical to SEQ ID NO: 3.

7. The homodimer of claim 1, wherein the homodimer has a catalytic activity (kcat/KM) of at least $8000M^{-1}\ s^{-1}$.

8. The homodimer of claim 1, wherein the ratio of PEG molecules to homodimer is about 25:1, one or more of the PEG molecules each independently has a molecular weight of about 5 kDa and is bound to the homodimer by way of an N-hydroxysuccinimide ester carbonate linking group.

9. A kynureninase homodimer produced by a method comprising contacting the homodimer with a PEGylation agent, wherein the molar input of PEGylation agent to homodimer is from about 15:1 to 30:1, wherein the homodimer comprises two polypeptide monomers each having an amino acid sequence that is at least 85% identical to the amino acid sequence of SEQ ID NO: 1, wherein each polypeptide monomer comprises the substitutions L72N, H102W, A282P, F306W, S408N, A436T, and N333T relative to SEQ ID NO: 1.

10. A pharmaceutical formulation comprising the kynureninase homodimer of claim 1 in a pharmaceutically acceptable carrier.

* * * * *

SEQUENCE LISTING

```
<160> NUMBER OF SEQ ID NOS: 3

<210> SEQ ID NO 1
<211> LENGTH: 465
<212> TYPE: PRT
<213> ORGANISM: Homo sapiens

<400> SEQUENCE: 1

Met Glu Pro Ser Ser Leu Glu Leu Pro Ala Asp Thr Val Gln Arg Ile
1               5                   10                  15

Ala Ala Glu Leu Lys Cys His Pro Thr Asp Glu Arg Val Ala Leu His
            20                  25                  30

Leu Asp Glu Glu Asp Lys Leu Arg His Phe Arg Glu Cys Phe Tyr Ile
        35                  40                  45

Pro Lys Ile Gln Asp Leu Pro Pro Val Asp Leu Ser Leu Val Asn Lys
    50                  55                  60

Asp Glu Asn Ala Ile Tyr Phe Leu Gly Asn Ser Leu Gly Leu Gln Pro
65                  70                  75                  80

Lys Met Val Lys Thr Tyr Leu Glu Glu Glu Leu Asp Lys Trp Ala Lys
                85                  90                  95

Ile Ala Ala Tyr Gly His Glu Val Gly Lys Arg Pro Trp Ile Thr Gly
            100                 105                 110

Asp Glu Ser Ile Val Gly Leu Met Lys Asp Ile Val Gly Ala Asn Glu
        115                 120                 125

Lys Glu Ile Ala Leu Met Asn Ala Leu Thr Val Asn Leu His Leu Leu
    130                 135                 140

Met Leu Ser Phe Phe Lys Pro Thr Pro Lys Arg Tyr Lys Ile Leu Leu
145                 150                 155                 160

Glu Ala Lys Ala Phe Pro Ser Asp His Tyr Ala Ile Glu Ser Gln Leu
                165                 170                 175

Gln Leu His Gly Leu Asn Ile Glu Glu Ser Met Arg Met Ile Lys Pro
            180                 185                 190

Arg Glu Gly Glu Glu Thr Leu Arg Ile Glu Asp Ile Leu Glu Val Ile
        195                 200                 205

Glu Lys Glu Gly Asp Ser Ile Ala Val Ile Leu Phe Ser Gly Val His
    210                 215                 220
```

-continued

Phe Tyr Thr Gly Gln His Phe Asn Ile Pro Ala Ile Thr Lys Ala Gly
225 230 235 240

Gln Ala Lys Gly Cys Tyr Val Gly Phe Asp Leu Ala His Ala Val Gly
245 250 255

Asn Val Glu Leu Tyr Leu His Asp Trp Gly Val Asp Phe Ala Cys Trp
260 265 270

Cys Ser Tyr Lys Tyr Leu Asn Ala Gly Ala Gly Gly Ile Ala Gly Ala
275 280 285

Phe Ile His Glu Lys His Ala His Thr Ile Lys Pro Ala Leu Val Gly
290 295 300

Trp Phe Gly His Glu Leu Ser Thr Arg Phe Lys Met Asp Asn Lys Leu
305 310 315 320

Gln Leu Ile Pro Gly Val Cys Gly Phe Arg Ile Ser Asn Pro Pro Ile
325 330 335

Leu Leu Val Cys Ser Leu His Ala Ser Leu Glu Ile Phe Lys Gln Ala
340 345 350

Thr Met Lys Ala Leu Arg Lys Lys Ser Val Leu Leu Thr Gly Tyr Leu
355 360 365

Glu Tyr Leu Ile Lys His Asn Tyr Gly Lys Asp Lys Ala Ala Thr Lys
370 375 380

Lys Pro Val Val Asn Ile Ile Thr Pro Ser His Val Glu Glu Arg Gly
385 390 395 400

Cys Gln Leu Thr Ile Thr Phe Ser Val Pro Asn Lys Asp Val Phe Gln
405 410 415

Glu Leu Glu Lys Arg Gly Val Val Cys Asp Lys Arg Asn Pro Asn Gly
420 425 430

Ile Arg Val Ala Pro Val Pro Leu Tyr Asn Ser Phe His Asp Val Tyr
435 440 445

Lys Phe Thr Asn Leu Leu Thr Ser Ile Leu Asp Ser Ala Glu Thr Lys
450 455 460

Asn
465

<210> SEQ ID NO 2
<211> LENGTH: 465
<212> TYPE: PRT
<213> ORGANISM: Artificial Sequence
<220> FEATURE:
<223> OTHER INFORMATION: Synthetic Construct

<400> SEQUENCE: 2

Met Glu Pro Ser Ser Leu Glu Leu Pro Ala Asp Thr Val Gln Arg Ile
1 5 10 15

Ala Ala Glu Leu Lys Cys His Pro Thr Asp Glu Arg Val Ala Leu His
20 25 30

Leu Asp Glu Glu Asp Lys Leu Arg His Phe Arg Glu Cys Phe Tyr Ile
35 40 45

Pro Lys Ile Gln Asp Leu Pro Pro Val Asp Leu Ser Leu Val Asn Lys
50 55 60

Asp Glu Asn Ala Ile Tyr Phe Asn Gly Asn Ser Leu Gly Leu Gln Pro
65 70 75 80

Lys Met Val Lys Thr Tyr Leu Glu Glu Glu Leu Asp Lys Trp Ala Lys
85 90 95

Ile Ala Arg Tyr Gly Trp Arg His Gly Lys Pro Pro Trp Ile Thr Tyr
100 105 110

Asp Glu Ser Ile Val Gly Leu Met Lys Asp Ile Val Gly Ala Asn Glu
115 120 125

Lys Glu Ile Ala Leu Met Asn Ala Leu Thr Val Asn Leu His Leu Leu
130 135 140

Met Leu Ser Phe Phe Lys Pro Thr Pro Lys Arg Tyr Lys Ile Leu Leu
145 150 155 160

Glu Ala Lys Ala Phe Pro Ser Asp His Tyr Ala Ile Glu Ser Gln Leu
165 170 175

Gln Leu His Gly Leu Asn Pro Glu Glu Ser Met Arg Met Ile Lys Pro
180 185 190

Arg Glu Gly Glu Glu Thr Leu Arg Ile Glu Asp Ile Leu Glu Val Ile
195 200 205

Glu Lys Glu Gly Asp Ser Ile Ala Val Ile Leu Phe Ser Gly Val His
210 215 220

Phe Tyr Thr Gly Gln His Phe Asn Ile Pro Ala Ile Thr Lys Ala Gly
225 230 235 240

Gln Ala Lys Gly Cys Tyr Val Gly Trp Asp Leu Ala His Ala Val Gly
245 250 255

Asn Val Glu Leu Tyr Leu His Asp Trp Gly Val Asp Phe Ala Cys Trp
260 265 270

Cys Ser Tyr Lys Tyr Leu Asn Ala Gly Pro Gly Gly Ile Ala Gly Ala
275 280 285

Phe Ile His Glu Lys His Ala His Thr Ile Lys Pro Ala Leu Val Gly
290 295 300

Trp Trp Gly His Glu Leu Ser Thr Arg Phe Lys Met Asp Asn Lys Leu
305 310 315 320

Gln Leu Ile Pro Gly Val Cys Gly Phe Arg Ser Ser Thr Pro Pro Ile
325 330 335

Leu Leu Val Cys Ser Leu His Ala Ser Leu Glu Ile Phe Lys Gln Ala
340 345 350

Thr Met Lys Ala Leu Arg Lys Lys Ser Val Leu Leu Thr Gly Tyr Leu
355 360 365

Glu Tyr Leu Ile Lys His Asn Tyr Gly Lys Asp Lys Ala Ala Thr Lys
370 375 380

Lys Pro Val Val Asn Ile Ile Thr Pro Ser His Val Glu Glu Arg Gly
385 390 395 400

Cys Gln Leu Thr Ile Thr Phe Asn Val Pro Asn Lys Asp Val Phe Gln
405 410 415

Glu Leu Glu Lys Arg Gly Val Val Cys Asp Lys Arg Asn Pro Asn Gly
420 425 430

Ile Arg Val Thr Pro Val Pro Leu Tyr Asn Ser Phe His Asp Val Tyr
435 440 445

Lys Phe Thr Asn Leu Leu Thr Ser Ile Leu Asp Ser Ala Glu Thr Lys
450 455 460

Asn
465

<210> SEQ ID NO 3
<211> LENGTH: 465
<212> TYPE: PRT
<213> ORGANISM: Artificial Sequence
<220> FEATURE:
<223> OTHER INFORMATION: Synthetic Construct

<400> SEQUENCE: 3

-continued

```
Met Glu Pro Ser Ser Leu Glu Leu Pro Ala Asp Thr Val Gln Arg Ile
1               5                   10                  15

Ala Ala Glu Leu Lys Cys His Pro Thr Asp Glu Arg Val Ala Leu His
            20                  25                  30

Leu Asp Glu Glu Asp Lys Leu Arg His Phe Arg Glu Cys Phe Tyr Ile
        35                  40                  45

Pro Lys Ile Gln Asp Leu Pro Pro Val Asp Leu Ser Leu Val Asn Lys
    50                  55                  60

Asp Glu Asn Ala Ile Tyr Phe Asn Gly Asn Ser Leu Gly Leu Gln Pro
65                  70                  75                  80

Lys Met Val Lys Thr Tyr Leu Glu Glu Glu Leu Asp Lys Trp Ala Lys
                85                  90                  95

Ile Ala Arg Tyr Gly Trp Arg His Gly Lys Pro Pro Trp Ile Thr Tyr
            100                 105                 110

Asp Glu Ser Ile Val Gly Leu Met Lys Asp Ile Val Gly Ala Asn Glu
        115                 120                 125

Lys Glu Ile Ala Leu Met Asn Ala Leu Thr Val Asn Leu His Leu Leu
    130                 135                 140

Met Leu Ser Phe Phe Lys Pro Thr Pro Lys Arg Tyr Lys Ile Leu Leu
145                 150                 155                 160

Glu Ala Lys Ala Phe Pro Ser Asp His Tyr Ala Ile Glu Ser Gln Leu
                165                 170                 175

Gln Leu His Gly Leu Asn Pro Glu Glu Ser Met Arg Met Ile Lys Pro
            180                 185                 190

Arg Glu Gly Glu Glu Thr Leu Arg Ile Glu Asp Ile Leu Glu Val Ile
        195                 200                 205

Glu Lys Glu Gly Asp Ser Ile Ala Val Ile Leu Phe Ser Gly Val His
    210                 215                 220

Phe Tyr Thr Gly Gln His Phe Asn Ile Pro Ala Ile Thr Lys Ala Gly
225                 230                 235                 240

Gln Ala Lys Gly Cys Tyr Val Gly Phe Asp Leu Ala His Ala Val Gly
                245                 250                 255

Asn Val Glu Leu Tyr Leu His Asp Trp Gly Val Asp Phe Ala Cys Trp
            260                 265                 270

Cys Ser Tyr Lys Tyr Leu Asn Ala Gly Pro Gly Gly Ile Ala Gly Ala
        275                 280                 285

Phe Ile His Glu Lys His Ala His Thr Ile Lys Pro Ala Leu Val Gly
    290                 295                 300

Trp Trp Gly His Glu Leu Ser Thr Arg Phe Lys Met Asp Asn Lys Leu
305                 310                 315                 320

Gln Leu Ile Pro Gly Val Cys Gly Phe Arg Ser Ser Thr Pro Pro Ile
                325                 330                 335

Leu Leu Val Cys Ser Leu His Ala Ser Leu Glu Ile Phe Lys Gln Ala
            340                 345                 350

Thr Met Lys Ala Leu Arg Lys Lys Ser Val Leu Leu Thr Gly Tyr Leu
        355                 360                 365

Glu Tyr Leu Ile Lys His Asn Tyr Gly Lys Asp Lys Ala Ala Thr Lys
    370                 375                 380

Lys Pro Val Val Asn Ile Ile Thr Pro Ser His Val Glu Glu Arg Gly
385                 390                 395                 400

Cys Gln Leu Thr Ile Thr Phe Asn Val Pro Asn Lys Asp Val Phe Gln
                405                 410                 415
```

-continued

```
Glu Leu Glu Lys Arg Gly Val Val Cys Asp Lys Arg Asn Pro Asn Gly
            420                 425                 430

Ile Arg Val Thr Pro Val Pro Leu Tyr Asn Ser Phe His Asp Val Tyr
        435                 440                 445

Lys Phe Thr Asn Leu Leu Thr Ser Ile Leu Asp Ser Ala Glu Thr Lys
    450                 455                 460

Asn
465
```